(12) United States Patent
Obika et al.

(10) Patent No.: US 10,377,789 B2
(45) Date of Patent: Aug. 13, 2019

(54) OLIGONUCLEOTIDE AND ARTIFICIAL NUCLEOSIDE HAVING GUANIDINE BRIDGE

(71) Applicant: OSAKA UNIVERSITY, Osaka (JP)

(72) Inventors: Satoshi Obika, Osaka (JP); Yutaro Kotobuki, Osaka (JP); Reiko Waki, Osaka (JP)

(73) Assignee: Osaka University, Osaka (JP)

( * ) Notice: Subject to any disclaimer, the term of this patent is extended or adjusted under 35 U.S.C. 154(b) by 131 days.

(21) Appl. No.: 14/428,646

(22) PCT Filed: Sep. 19, 2013

(86) PCT No.: PCT/JP2013/075370
§ 371 (c)(1),
(2) Date: Mar. 17, 2015

(87) PCT Pub. No.: WO2014/046212
PCT Pub. Date: Mar. 27, 2014

(65) Prior Publication Data
US 2015/0266917 A1 Sep. 24, 2015

(30) Foreign Application Priority Data

Sep. 21, 2012 (JP) .................. 2012-208906
Feb. 7, 2013 (JP) .................. 2013-022360

(51) Int. Cl.
| C07H 19/06 | (2006.01) |
| C07H 19/10 | (2006.01) |
| C07H 21/00 | (2006.01) |
| C07H 21/02 | (2006.01) |
| C07H 21/04 | (2006.01) |
| C07H 23/00 | (2006.01) |

(52) U.S. Cl.
CPC .............. *C07H 19/10* (2013.01); *C07H 19/06* (2013.01); *C07H 21/00* (2013.01); *C07H 21/02* (2013.01); *C07H 21/04* (2013.01); *C07H 23/00* (2013.01)

(58) Field of Classification Search
CPC ........ C07H 19/06; C07H 19/10; C07H 21/02; C07H 21/04; C07H 21/00; C07H 23/00
See application file for complete search history.

(56) References Cited

U.S. PATENT DOCUMENTS

| 4,458,066 A * | 7/1984 | Caruthers | ............ B01J 19/0046 |
| | | | 536/25.34 |
| 4,500,707 A * | 2/1985 | Caruthers | ............ B01J 19/0046 |
| | | | 536/25.34 |
| 4,668,777 A * | 5/1987 | Caruthers | ............ C07H 21/00 |
| | | | 536/26.5 |

(Continued)

FOREIGN PATENT DOCUMENTS

| EP | 1481983 | 12/2004 |
| EP | 2495248 | 9/2012 |
| WO | 2007026824 | 3/2007 |

OTHER PUBLICATIONS ( R ) Ikeda et al., "Doubly Thiazole Orange-Labeled Cytidine for Functional Expansion for a Hybridization-Sensitive Probe," Tetrahedron Letters, 50(51), 7191-7195 (2009).*

(Continued)

*Primary Examiner* — Lawrence E Crane
(74) *Attorney, Agent, or Firm* — Renner, Otto, Boisselle & Sklar, LLP

(57) ABSTRACT

A compound represented by formula I or II below or a salt thereof:

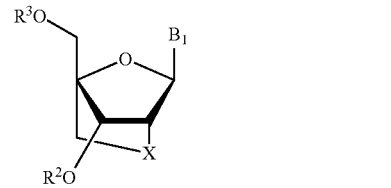

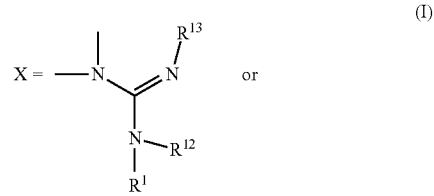

wherein $B_1$ represents a purin-9-yl group or a 2-oxo-1,2-dihydropyrimidin-1-yl group that has any one or more substituents selected from the group consisting of a hydroxyl group, a hydroxyl group protected by a protecting group in nucleic acid synthesis, a $C_1$ to $C_6$ linear alkyl group, a $C_1$ to $C_6$ linear alkoxy group, a mercapto group, a mercapto group protected by a protecting group in nucleic acid synthesis, a $C_1$ to $C_6$ linear alkylthio group, an amino group, a $C_1$ to $C_6$ linear alkylamino group, an amino group protected by a protecting group in nucleic acid synthesis, and a halogen atom.

7 Claims, 4 Drawing Sheets
Specification includes a Sequence Listing.

(56) References Cited

U.S. PATENT DOCUMENTS

| | | | |
|---|---|---|---|
| 4,973,679 A * | 11/1990 | Caruthers | C07H 21/00 536/25.3 |
| 5,132,418 A * | 7/1992 | Caruthers | B01J 19/0046 536/25.3 |
| 6,268,490 B1 | 7/2001 | Imanishi et al. | |
| 7,427,672 B2 * | 9/2008 | Imanishi | C07H 19/04 536/22.1 |
| 7,615,619 B2 * | 11/2009 | Imanishi | C07H 19/06 536/23.1 |
| 8,536,323 B2 * | 9/2013 | Opperman | C07H 19/10 536/26.3 |
| 8,541,562 B2 * | 9/2013 | Obika | C07H 19/06 536/23.1 |
| 9,206,216 B2 * | 12/2015 | Etienne | C07H 19/10 |
| 2006/0166908 A1 | 7/2006 | Imanishi et al. | |
| 2007/0167387 A1 | 7/2007 | Imanishi et al. | |
| 2012/0208991 A1 | 8/2012 | Obika et al. | |

OTHER PUBLICATIONS (S) Caruthers (I), "Gene Synthesis Machines: DNA Chemistry and Its Uses," Science, 230, 281-285 (Oct. 18, 1985).*

(T) Caruthers (II), "A Brief Review of DNA and RNA Chemical Synthesis," Biochem. Soc. Trans., 39, 575-580 (2011).*

M. Park et al.; Development of potential anticancer agents that target the telomere sequence; Bioorganic & Medicinal Chemistry Letters 20 (2010); pp. 3982-3986.

Masaru Nishida et al., Chemical Communications, Aug. 7, 2010, vol. 46, No. 29, p. 5283-5285.

Kazuyuki Miyashita et al., Chemical Communications, Sep. 28, 2007, No. 36, p. 3765-3767.

Takeshi Imanishi et al., J. Synth. Org. Chern., Jpn., Nov. 1999, vol. 57, No. II, p. 969-980.

Yutaro Kotobiki et al., Antisense DNA/RNA Kenkyukai Idenshi Delivery Kenkyukai Antisense Idenshi Delivery Symposium 2012 Yoshishu, Sep. 24, 2012, p. 25.

Masayasu Kuwahara et al., Kagaku Kogyo, Jan. 1, 2012, vol. 63, No. 1, p. 42-48.

PCT/JP2013/075370; PCT International Search Report dated Dec. 3, 2013.

C. Wahlestedt et al., Proc. Natl. Acad. Sci. USA, 2000, vol. 97, No. 10, pp. 5633-5638.

Y. Hari et al., Bioorg. Med. Chem., 2006, vol. 14, pp. 1029-1038.

S.M.A. Rahman et al, J. Am. Chem. Soc., 2008, vol. 130, No. 14, pp. 4886-4896.

M. Kuwahara et al., Nucleic Acids Res., 2008, vol. 36, No. 13, pp. 4257-4265.

S. Obika et al., Bioorg. Med. Chem., 2001, vol. 9, pp. 1001-1011.

A.R. Shrestha et al., J. Org. Chem., 2011, vol. 76, p. 9891-9899.

Partial English translation of Yutaro Kotobiki et al., Antisense DNA/RNA Kenkyukai Idenshi Delivery Kenkyukai Antisense Idenshi Delivery Symposium 2012 Yoshishu, Sep. 24, 2012, p. 25. (Japanese version previously submitted).

Partial English translation of Masayasu Kuwahara et al., Kagaku Kogyo, Jan. 1, 2012, vol. 63, No. 1, p. 42-48. (Japanese version previously submitted).

* cited by examiner

[Figure 1]
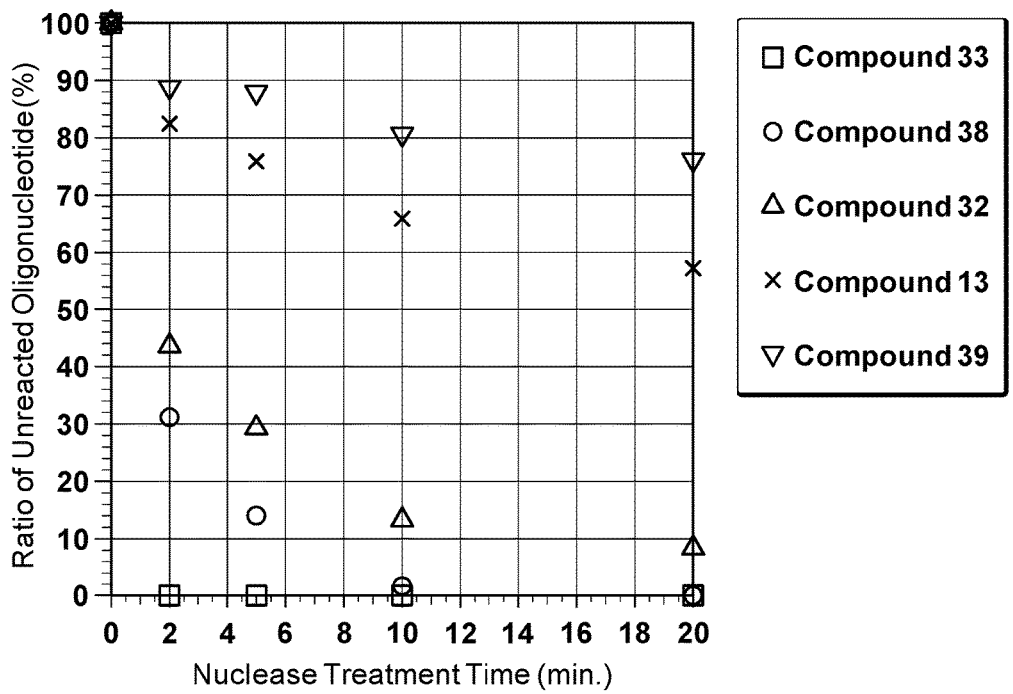
[Figure 2]
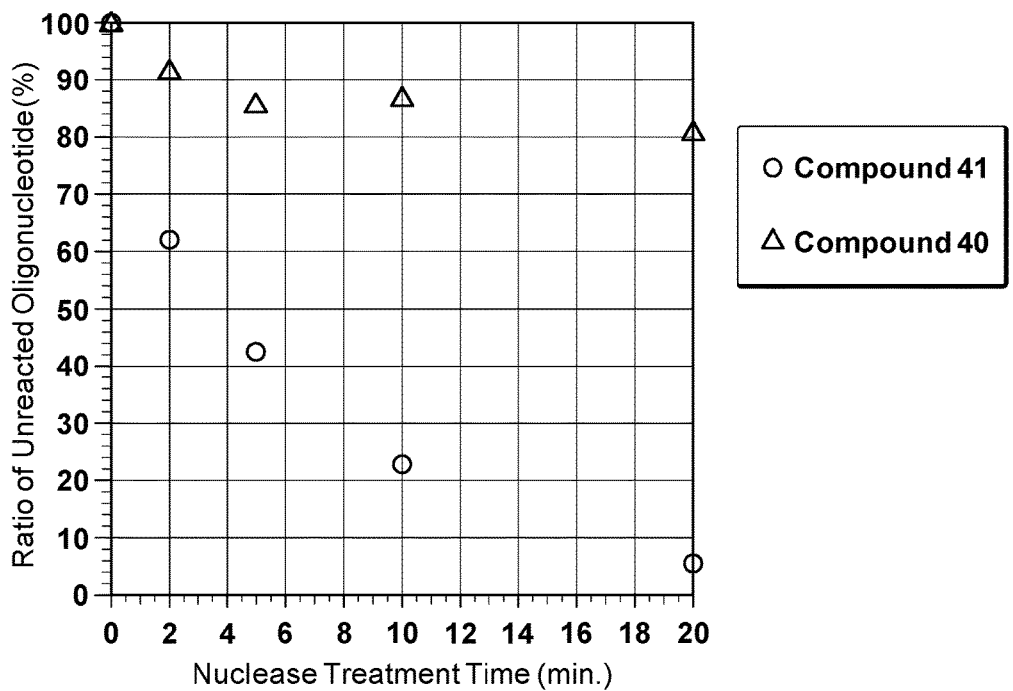

[Figure 3]
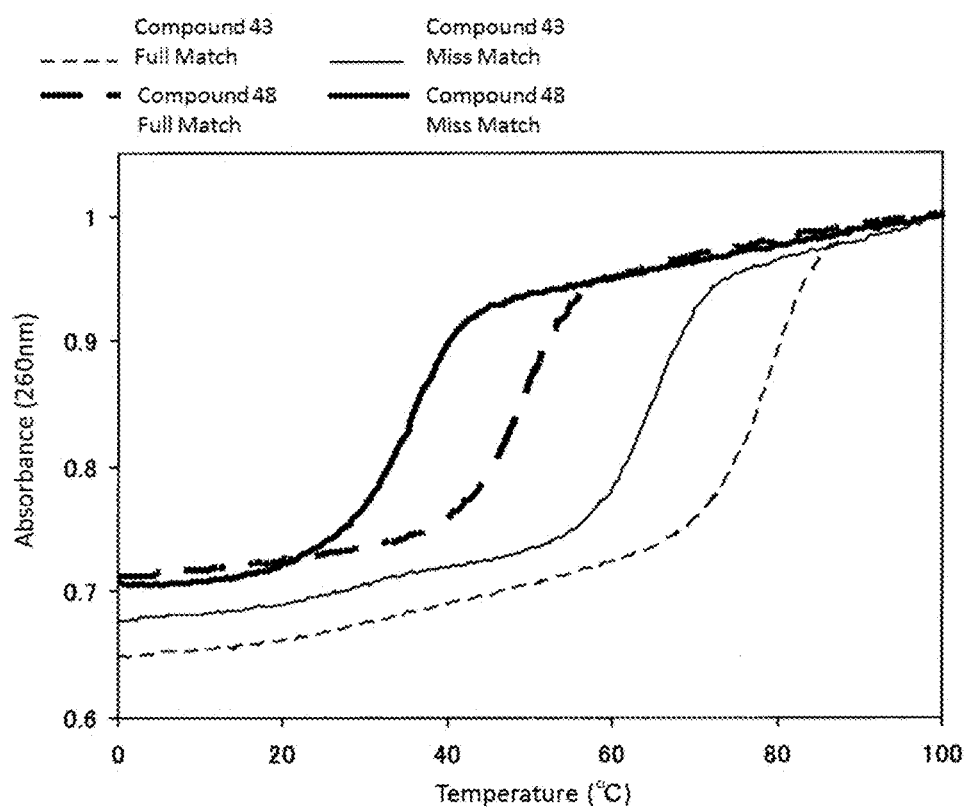

[Figure 4]
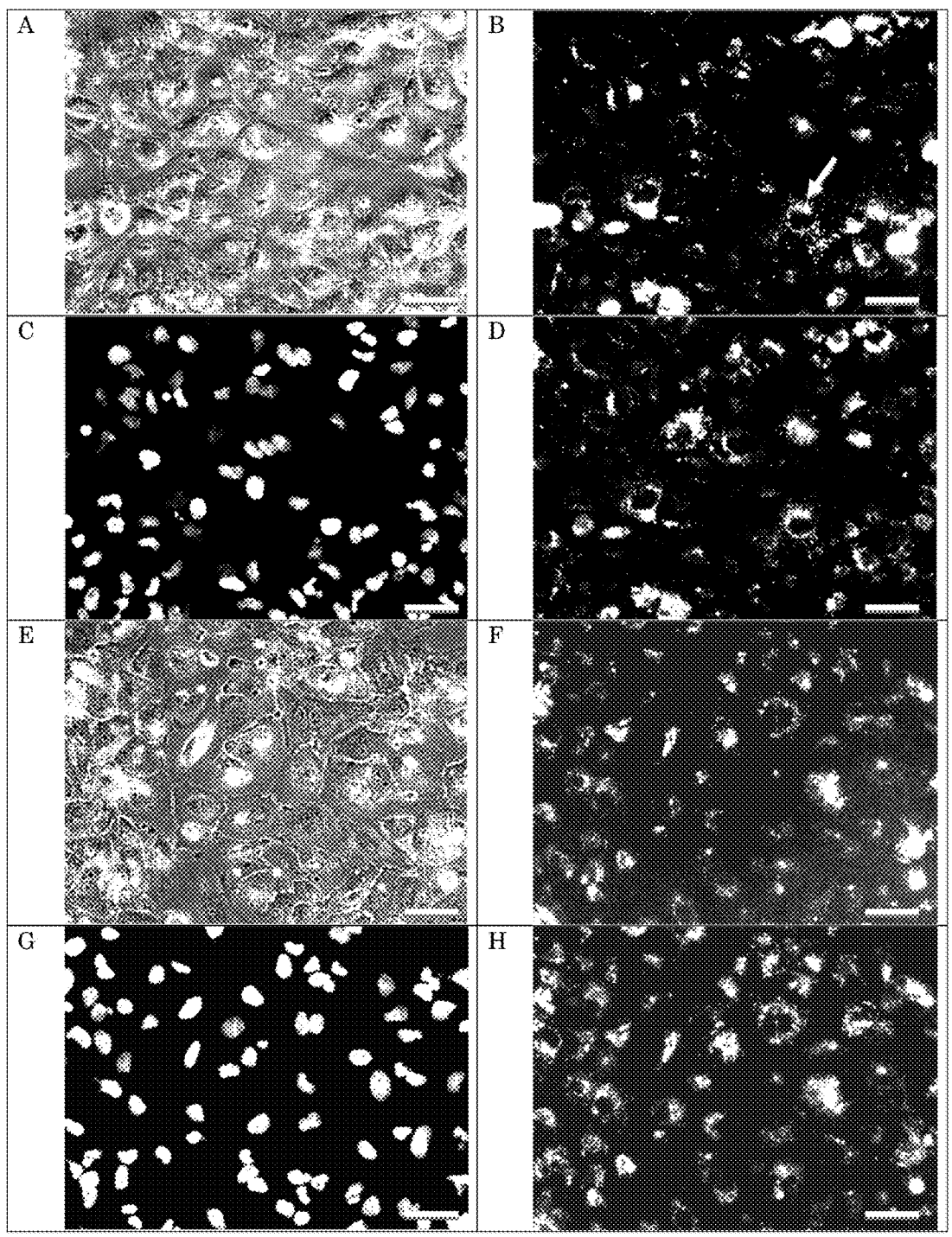

[Figure 5]
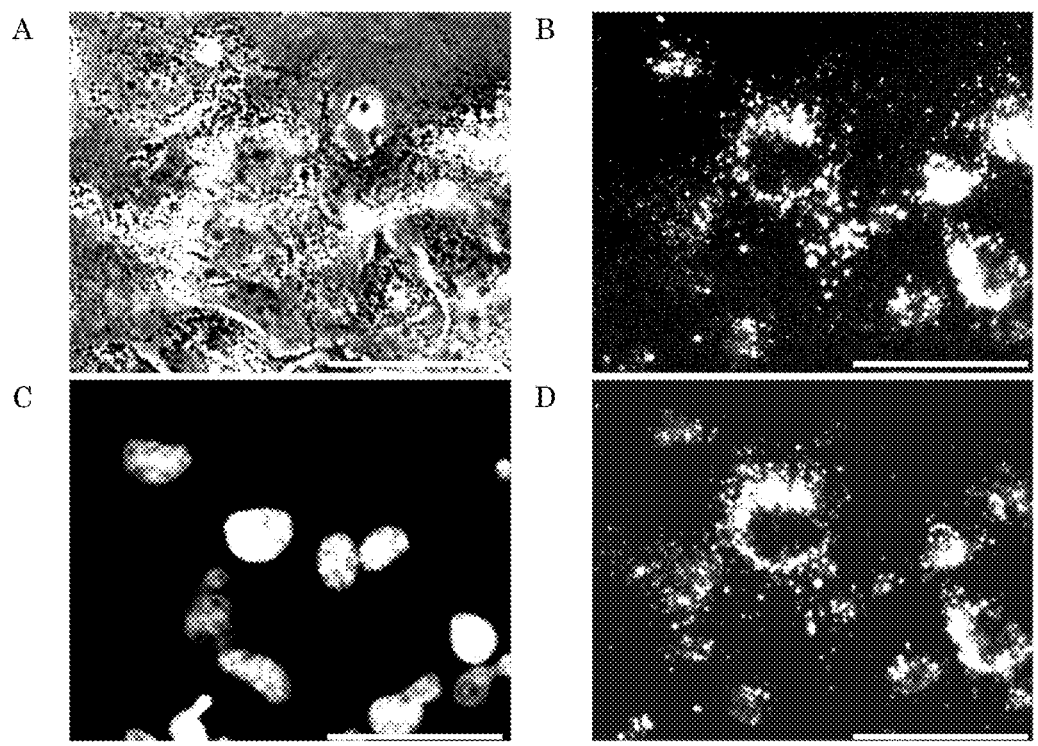

SEQUENCE LISTING

```
<160> NUMBER OF SEQ ID NOS: 46

<210> SEQ ID NO 1
<211> LENGTH: 12
<212> TYPE: DNA
<213> ORGANISM: Artificial
<220> FEATURE:
<223> OTHER INFORMATION: Compound 9
<220> FEATURE:
<221> NAME/KEY: misc_feature
<222> LOCATION: 6..6
<223> OTHER INFORMATION: Guanidine-Bridged Nucleic Acid

<400> SEQUENCE: 1
gcgttntttg ct                                                         12

<210> SEQ ID NO 2
<211> LENGTH: 12
<212> TYPE: DNA
```

```
<213> ORGANISM: Artificial
<220> FEATURE:
<223> OTHER INFORMATION: Compound 10
<220> FEATURE:
<221> NAME/KEY: misc_feature
<222> LOCATION: 6..6
<223> OTHER INFORMATION: Guanidine-Bridged Nucleic Acid
<220> FEATURE:
<221> NAME/KEY: misc_feature
<222> LOCATION: 8..8
<223> OTHER INFORMATION: Guanidine-Bridged Nucleic Acid

<400> SEQUENCE: 2
gcgttntntg ct                                                            12

<210> SEQ ID NO 3
<211> LENGTH: 12
<212> TYPE: DNA
<213> ORGANISM: Artificial
<220> FEATURE:
<223> OTHER INFORMATION: Compound 11
<220> FEATURE:
<221> NAME/KEY: misc_feature
<222> LOCATION: 4..4
<223> OTHER INFORMATION: Guanidine-Bridged Nucleic Acid
<220> FEATURE:
<221> NAME/KEY: misc_feature
<222> LOCATION: 6..6
<223> OTHER INFORMATION: Guanidine-Bridged Nucleic Acid
<220> FEATURE:
<221> NAME/KEY: misc_feature
<222> LOCATION: 8..8
<223> OTHER INFORMATION: Guanidine-Bridged Nucleic Acid

<400> SEQUENCE: 3
gcgntntntg ct                                                            12

<210> SEQ ID NO 4
<211> LENGTH: 12
<212> TYPE: DNA
<213> ORGANISM: Artificial
<220> FEATURE:
<223> OTHER INFORMATION: Compound 12
<220> FEATURE:
<221> NAME/KEY: misc_feature
<222> LOCATION: 6..6
<223> OTHER INFORMATION: Guanidine-Bridged Nucleic Acid
<220> FEATURE:
<221> NAME/KEY: misc_feature
<222> LOCATION: 7..7
<223> OTHER INFORMATION: Guanidine-Bridged Nucleic Acid

<400> SEQUENCE: 4
gcgttnnttg ct                                                            12

<210> SEQ ID NO 5
<211> LENGTH: 9
<212> TYPE: DNA
<213> ORGANISM: Artificial
<220> FEATURE:
<223> OTHER INFORMATION: Compound 13
<220> FEATURE:
<221> NAME/KEY: misc_feature
<222> LOCATION: 8..8
<223> OTHER INFORMATION: Guanidine-Bridged Nucleic Acid

<400> SEQUENCE: 5 tttttttnt                                                                 9

<210> SEQ ID NO 6
<211> LENGTH: 12
```

```
<212> TYPE: DNA
<213> ORGANISM: Artificial
<220> FEATURE:
<223> OTHER INFORMATION: Target chain

<400> SEQUENCE: 6
agcaaaaaac gc                                                             12

<210> SEQ ID NO 7
<211> LENGTH: 12
<212> TYPE: DNA
<213> ORGANISM: Artificial
<220> FEATURE:
<223> OTHER INFORMATION: Compound 14

<400> SEQUENCE: 7
gcgttttttg ct                                                             12

<210> SEQ ID NO 8
<211> LENGTH: 12
<212> TYPE: DNA
<213> ORGANISM: Artificial
<220> FEATURE:
<223> OTHER INFORMATION: Compound 15
<220> FEATURE:
<221> NAME/KEY: misc_feature
<222> LOCATION: 6..6
<223> OTHER INFORMATION: Urea-Bridged Nucleic Acid

<400> SEQUENCE: 8
gcgttntttg ct                                                             12

<210> SEQ ID NO 9
<211> LENGTH: 12
<212> TYPE: DNA
<213> ORGANISM: Artificial
<220> FEATURE:
<223> OTHER INFORMATION: Compound 16
<220> FEATURE:
<221> NAME/KEY: misc_feature
<222> LOCATION: 6..6
<223> OTHER INFORMATION: Urea-Bridged Nucleic Acid
<220> FEATURE:
<221> NAME/KEY: misc_feature
<222> LOCATION: 8..8
<223> OTHER INFORMATION: Urea-Bridged Nucleic Acid

<400> SEQUENCE: 9
gcgttntntg ct                                                             12

<210> SEQ ID NO 10
<211> LENGTH: 12
<212> TYPE: DNA
<213> ORGANISM: Artificial
<220> FEATURE:
<223> OTHER INFORMATION: Compound 17
<220> FEATURE:
<221> NAME/KEY: misc_feature
<222> LOCATION: 4..4
<223> OTHER INFORMATION: Urea-Bridged Nucleic Acid
<220> FEATURE:
<221> NAME/KEY: misc_feature
<222> LOCATION: 6..6
<223> OTHER INFORMATION: Urea-Bridged Nucleic Acid
<220> FEATURE:
<221> NAME/KEY: misc_feature
<222> LOCATION: 8..8
<223> OTHER INFORMATION: Urea-Bridged Nucleic Acid

<400> SEQUENCE: 10
```

```
gcgntntntg ct                                                    12
```

<210> SEQ ID NO 11
<211> LENGTH: 12
<212> TYPE: DNA
<213> ORGANISM: Artificial
<220> FEATURE:
<223> OTHER INFORMATION: Compound 18
<220> FEATURE:
<221> NAME/KEY: misc_feature
<222> LOCATION: 6..6
<223> OTHER INFORMATION: Urea-Bridged Nucleic Acid
<220> FEATURE:
<221> NAME/KEY: misc_feature
<222> LOCATION: 7..7
<223> OTHER INFORMATION: Urea-Bridged Nucleic Acid

<400> SEQUENCE: 11

```
gcgttnnttg ct                                                    12
```

<210> SEQ ID NO 12
<211> LENGTH: 10
<212> TYPE: DNA
<213> ORGANISM: Artificial
<220> FEATURE:
<223> OTHER INFORMATION: Compound 29
<220> FEATURE:
<221> NAME/KEY: misc_feature
<222> LOCATION: 5..5
<223> OTHER INFORMATION: Guanidine-Bridged Nucleic Acid

<400> SEQUENCE: 12

```
ttttnttttt                                                       10
```

<210> SEQ ID NO 13
<211> LENGTH: 10
<212> TYPE: DNA
<213> ORGANISM: Artificial
<220> FEATURE:
<223> OTHER INFORMATION: Compound 30
<220> FEATURE:
<221> NAME/KEY: misc_feature
<222> LOCATION: 5..5
<223> OTHER INFORMATION: Guanidine-Bridged Nucleic Acid
<220> FEATURE:
<221> NAME/KEY: misc_feature
<222> LOCATION: 7..7
<223> OTHER INFORMATION: Guanidine-Bridged Nucleic Acid

<400> SEQUENCE: 13

```
ttttntnttt                                                       10
```

<210> SEQ ID NO 14
<211> LENGTH: 10
<212> TYPE: DNA
<213> ORGANISM: Artificial
<220> FEATURE:
<223> OTHER INFORMATION: Compound 31
<220> FEATURE:
<221> NAME/KEY: misc_feature
<222> LOCATION: 3..3
<223> OTHER INFORMATION: Guanidine-Bridged Nucleic Acid
<220> FEATURE:
<221> NAME/KEY: misc_feature
<222> LOCATION: 5..5
<223> OTHER INFORMATION: Guanidine-Bridged Nucleic Acid
<220> FEATURE:
<221> NAME/KEY: misc_feature
<222> LOCATION: 7..7
<223> OTHER INFORMATION: Guanidine-Bridged Nucleic Acid

<400> SEQUENCE: 14 ttntntnttt                                                           10

<210> SEQ ID NO 15
<211> LENGTH: 10
<212> TYPE: DNA
<213> ORGANISM: Artificial
<220> FEATURE:
<223> OTHER INFORMATION: Compound 32
<220> FEATURE:
<221> NAME/KEY: misc_feature
<222> LOCATION: 9..9
<223> OTHER INFORMATION: Guanidine-Bridged Nucleic Acid

<400> SEQUENCE: 15 ttttttttnt                                                           10

<210> SEQ ID NO 16
<211> LENGTH: 10
<212> TYPE: DNA
<213> ORGANISM: Artificial
<220> FEATURE:
<223> OTHER INFORMATION: Target chain or Compound 33

<400> SEQUENCE: 16
tttttttttt                                                           10

<210> SEQ ID NO 17
<211> LENGTH: 10
<212> TYPE: DNA
<213> ORGANISM: Artificial
<220> FEATURE:
<223> OTHER INFORMATION: Target chain

<400> SEQUENCE: 17
aaaaaaaaaa                                                           10

<210> SEQ ID NO 18
<211> LENGTH: 10
<212> TYPE: DNA
<213> ORGANISM: Artificial
<220> FEATURE:
<223> OTHER INFORMATION: Target chain

<400> SEQUENCE: 18
aaaaagaaaa                                                           10

<210> SEQ ID NO 19
<211> LENGTH: 10
<212> TYPE: DNA
<213> ORGANISM: Artificial
<220> FEATURE:
<223> OTHER INFORMATION: Target chain

<400> SEQUENCE: 19
aaaaacaaaa                                                           10

<210> SEQ ID NO 20
<211> LENGTH: 10
<212> TYPE: DNA
<213> ORGANISM: Artificial
<220> FEATURE:
<223> OTHER INFORMATION: Target chain

<400> SEQUENCE: 20
aaaaataaaa                                                           10

```
<210> SEQ ID NO 21
<211> LENGTH: 9
<212> TYPE: DNA
<213> ORGANISM: Artificial
<220> FEATURE:
<223> OTHER INFORMATION: Target chain

<400> SEQUENCE: 21 gtgatatgc                                                                 9

<210> SEQ ID NO 22
<211> LENGTH: 9
<212> TYPE: DNA
<213> ORGANISM: Artificial
<220> FEATURE:
<223> OTHER INFORMATION: Compound 35

<400> SEQUENCE: 22 gcatatcac                                                                 9

<210> SEQ ID NO 23
<211> LENGTH: 9
<212> TYPE: DNA
<213> ORGANISM: Artificial
<220> FEATURE:
<223> OTHER INFORMATION: Compound 34
<220> FEATURE:
<221> NAME/KEY: misc_feature
<222> LOCATION: 4..4
<223> OTHER INFORMATION: Guanidine-Bridged Nucleic Acid

<400> SEQUENCE: 23 gcanatcac                                                                 9

<210> SEQ ID NO 24
<211> LENGTH: 15
<212> TYPE: DNA
<213> ORGANISM: Artificial
<220> FEATURE:
<223> OTHER INFORMATION: Compound 36
<220> FEATURE:
<221> NAME/KEY: misc_feature
<222> LOCATION: 6..6
<223> OTHER INFORMATION: Guanidine-Bridged Nucleic Acid
<220> FEATURE:
<221> NAME/KEY: misc_feature
<222> LOCATION: 8..8
<223> OTHER INFORMATION: 2'-deoxy-5-methylcytidine
<220> FEATURE:
<221> NAME/KEY: misc_feature
<222> LOCATION: 10..10
<223> OTHER INFORMATION: Guanidine-Bridged Nucleic Acid
<220> FEATURE:
<221> NAME/KEY: misc_feature
<222> LOCATION: 12..12
<223> OTHER INFORMATION: Guanidine-Bridged Nucleic Acid
<220> FEATURE:
<221> NAME/KEY: misc_feature
<222> LOCATION: 14..14
<223> OTHER INFORMATION: Guanidine-Bridged Nucleic Acid

<400> SEQUENCE: 24 tttttntntntntnt                                                          15

<210> SEQ ID NO 25
<211> LENGTH: 21
<212> TYPE: DNA
<213> ORGANISM: Artificial
<220> FEATURE:
<223> OTHER INFORMATION: Target chain in double strand
```

<220> FEATURE:
<221> NAME/KEY: misc_feature
<222> LOCATION: 11..11
<223> OTHER INFORMATION: Target DNA duplex prepared by linking the 3'
      end of SEQ ID No. 25 and the 5' end of SEQ ID No. 26 via a C-18
      spacer as a linker, where: n25=a and n26=t; n25=t and n26=a;
      n25=g and n26=c; or n25=c and n26=g

<400> SEQUENCE: 25
ggcaaaaaga nagagagacg c                                             21

<210> SEQ ID NO 26
<211> LENGTH: 21
<212> TYPE: DNA
<213> ORGANISM: Artificial
<220> FEATURE:
<223> OTHER INFORMATION: Complementary chain in double strand
<220> FEATURE:
<221> NAME/KEY: misc_feature
<222> LOCATION: 11..11
<223> OTHER INFORMATION: Target DNA duplex prepared by linking the 3'
      end of SEQ ID No. 25 and the 5' end of SEQ ID No. 26 via a C-18
      spacer as a linker, where: n25=a and n26=t; n25=t and n26=a;
      n25=g and n26=c; or n25=c and n26=g

<400> SEQUENCE: 26
gcgtctctct ntcttttgc c                                              21

<210> SEQ ID NO 27
<211> LENGTH: 15
<212> TYPE: DNA
<213> ORGANISM: Artificial
<220> FEATURE:
<223> OTHER INFORMATION: Compound 37
<220> FEATURE:
<221> NAME/KEY: misc_feature
<222> LOCATION: 6..6
<223> OTHER INFORMATION: 2'-deoxy-5-methylcytidine
<220> FEATURE:
<221> NAME/KEY: misc_feature
<222> LOCATION: 10..10
<223> OTHER INFORMATION: 2'-deoxy-5-methylcytidine
<220> FEATURE:
<221> NAME/KEY: misc_feature
<222> LOCATION: 12..12
<223> OTHER INFORMATION: 2'-deoxy-5-methylcytidine
<220> FEATURE:
<221> NAME/KEY: misc_feature
<222> LOCATION: 14..14
<223> OTHER INFORMATION: 2'-deoxy-5-methylcytidine

<400> SEQUENCE: 27 tttttntttntntnt                                                     15

<210> SEQ ID NO 28
<211> LENGTH: 15
<212> TYPE: DNA
<213> ORGANISM: Artificial
<220> FEATURE:
<223> OTHER INFORMATION: Modified Compound 36
<220> FEATURE:
<221> NAME/KEY: misc_feature
<222> LOCATION: 6..6
<223> OTHER INFORMATION: 2'-deoxy-5-methylcytidine
<220> FEATURE:
<221> NAME/KEY: misc_feature
<222> LOCATION: 8..8
<223> OTHER INFORMATION: Guanidine-Bridged Nucleic Acid
<220> FEATURE:
<221> NAME/KEY: misc_feature
<222> LOCATION: 10..10
<223> OTHER INFORMATION: 2'-deoxy-5-methylcytidine
<220> FEATURE:

```
<221> NAME/KEY: misc_feature
<222> LOCATION: 12..12
<223> OTHER INFORMATION: 2'-deoxy-5-methylcytidine
<220> FEATURE:
<221> NAME/KEY: misc_feature
<222> LOCATION: 14..14
<223> OTHER INFORMATION: 2'-deoxy-5-methylcytidine

<400> SEQUENCE: 28 tttttntntntntnt                                                         15

<210> SEQ ID NO 29
<211> LENGTH: 10
<212> TYPE: DNA
<213> ORGANISM: Artificial
<220> FEATURE:
<223> OTHER INFORMATION: Target Chain
<220> FEATURE:
<221> NAME/KEY: misc_feature
<222> LOCATION: 9..9
<223> OTHER INFORMATION: Guanidine-Bridged Nucleic Acid

<400> SEQUENCE: 29 tttttttnt                                                               10

<210> SEQ ID NO 30

<400> SEQUENCE: 30

000

<210> SEQ ID NO 31
<211> LENGTH: 10
<212> TYPE: DNA
<213> ORGANISM: Artificial
<220> FEATURE:
<223> OTHER INFORMATION: Compound 42
<220> FEATURE:
<221> NAME/KEY: misc_feature
<222> LOCATION: 4..4
<223> OTHER INFORMATION: Guanidine-Bridged Nucleic Acid
<220> FEATURE:
<221> NAME/KEY: misc_feature
<222> LOCATION: 5..5
<223> OTHER INFORMATION: Guanidine-Bridged Nucleic Acid
<220> FEATURE:
<221> NAME/KEY: misc_feature
<222> LOCATION: 6..6
<223> OTHER INFORMATION: Guanidine-Bridged Nucleic Acid

<400> SEQUENCE: 31 tttnnntttt                                                              10

<210> SEQ ID NO 32
<211> LENGTH: 10
<212> TYPE: DNA
<213> ORGANISM: Artificial
<220> FEATURE:
<223> OTHER INFORMATION: Compound 43
<220> FEATURE:
<221> NAME/KEY: misc_feature
<222> LOCATION: 1..1
<223> OTHER INFORMATION: Guanidine-Bridged Nucleic Acid
<220> FEATURE:
<221> NAME/KEY: misc_feature
<222> LOCATION: 3..3
<223> OTHER INFORMATION: Guanidine-Bridged Nucleic Acid
<220> FEATURE:
<221> NAME/KEY: misc_feature
<222> LOCATION: 5..5
<223> OTHER INFORMATION: Guanidine-Bridged Nucleic Acid
<220> FEATURE:
```

```
<221> NAME/KEY: misc_feature
<222> LOCATION: 7..7
<223> OTHER INFORMATION: Guanidine-Bridged Nucleic Acid
<220> FEATURE:
<221> NAME/KEY: misc_feature
<222> LOCATION: 9..9
<223> OTHER INFORMATION: Guanidine-Bridged Nucleic Acid

<400> SEQUENCE: 32 ntntntntnt                                                                   10

<210> SEQ ID NO 33
<211> LENGTH: 10
<212> TYPE: DNA
<213> ORGANISM: Artificial
<220> FEATURE:
<223> OTHER INFORMATION: Compound 44
<220> FEATURE:
<221> NAME/KEY: misc_feature
<222> LOCATION: 5..5
<223> OTHER INFORMATION: Thymine LNA

<400> SEQUENCE: 33 ttttnttttt                                                                   10

<210> SEQ ID NO 34
<211> LENGTH: 10
<212> TYPE: DNA
<213> ORGANISM: Artificial
<220> FEATURE:
<223> OTHER INFORMATION: Compound 45
<220> FEATURE:
<221> NAME/KEY: misc_feature
<222> LOCATION: 5..5
<223> OTHER INFORMATION: Thymine LNA
<220> FEATURE:
<221> NAME/KEY: misc_feature
<222> LOCATION: 7..7
<223> OTHER INFORMATION: Thymine LNA

<400> SEQUENCE: 34 ttttntnttt                                                                   10

<210> SEQ ID NO 35
<211> LENGTH: 10
<212> TYPE: DNA
<213> ORGANISM: Artificial
<220> FEATURE:
<223> OTHER INFORMATION: Compound 46
<220> FEATURE:
<221> NAME/KEY: misc_feature
<222> LOCATION: 3..3
<223> OTHER INFORMATION: Thymine LNA
<220> FEATURE:
<221> NAME/KEY: misc_feature
<222> LOCATION: 5..5
<223> OTHER INFORMATION: Thymine LNA
<220> FEATURE:
<221> NAME/KEY: misc_feature
<222> LOCATION: 7..7
<223> OTHER INFORMATION: Thymine LNA

<400> SEQUENCE: 35 ttntntnttt                                                                   10

<210> SEQ ID NO 36
<211> LENGTH: 10
<212> TYPE: DNA
<213> ORGANISM: Artificial
<220> FEATURE:
<223> OTHER INFORMATION: Compound 47
```

```
<220> FEATURE:
<221> NAME/KEY: misc_feature
<222> LOCATION: 4..4
<223> OTHER INFORMATION: Thymine LNA
<220> FEATURE:
<221> NAME/KEY: misc_feature
<222> LOCATION: 5..5
<223> OTHER INFORMATION: Thymine LNA
<220> FEATURE:
<221> NAME/KEY: misc_feature
<222> LOCATION: 6..6
<223> OTHER INFORMATION: Thymine LNA

<400> SEQUENCE: 36 tttnnntttt                                                                  10

<210> SEQ ID NO 37
<211> LENGTH: 10
<212> TYPE: DNA
<213> ORGANISM: Artificial
<220> FEATURE:
<223> OTHER INFORMATION: Compound 48
<220> FEATURE:
<221> NAME/KEY: misc_feature
<222> LOCATION: 1..1
<223> OTHER INFORMATION: Thymine LNA
<220> FEATURE:
<221> NAME/KEY: misc_feature
<222> LOCATION: 3..3
<223> OTHER INFORMATION: Thymine LNA
<220> FEATURE:
<221> NAME/KEY: misc_feature
<222> LOCATION: 5..5
<223> OTHER INFORMATION: Thymine LNA
<220> FEATURE:
<221> NAME/KEY: misc_feature
<222> LOCATION: 7..7
<223> OTHER INFORMATION: Thymine LNA
<220> FEATURE:
<221> NAME/KEY: misc_feature
<222> LOCATION: 9..9
<223> OTHER INFORMATION: Thymine LNA

<400> SEQUENCE: 37 ntntntntnt                                                                  10

<210> SEQ ID NO 38
<211> LENGTH: 12
<212> TYPE: DNA
<213> ORGANISM: Artificial
<220> FEATURE:
<223> OTHER INFORMATION: Compound 53
<220> FEATURE:
<221> NAME/KEY: misc_feature
<222> LOCATION: 1..1
<223> OTHER INFORMATION: Alexa Fluor 488
<220> FEATURE:
<221> NAME/KEY: misc_feature
<222> LOCATION: 2..2
<223> OTHER INFORMATION: Thiol

<400> SEQUENCE: 38 nnttttttttttt                                                               12

<210> SEQ ID NO 39
<211> LENGTH: 12
<212> TYPE: DNA
<213> ORGANISM: Artificial
<220> FEATURE:
<223> OTHER INFORMATION: Compound 54
<220> FEATURE:
<221> NAME/KEY: misc_feature
<222> LOCATION: 1..1
```

```
<223> OTHER INFORMATION: Alexa Fluor 488
<220> FEATURE:
<221> NAME/KEY: misc_feature
<222> LOCATION: 2..2
<223> OTHER INFORMATION: Thiol
<220> FEATURE:
<221> NAME/KEY: misc_feature
<222> LOCATION: 8..8
<223> OTHER INFORMATION: Guanidine-Bridged Nucleic Acid

<400> SEQUENCE: 39 nnttttntttt                                                          12

<210> SEQ ID NO 40
<211> LENGTH: 12
<212> TYPE: DNA
<213> ORGANISM: Artificial
<220> FEATURE:
<223> OTHER INFORMATION: Compound 55
<220> FEATURE:
<221> NAME/KEY: misc_feature
<222> LOCATION: 1..1
<223> OTHER INFORMATION: Alexa Fluor 488
<220> FEATURE:
<221> NAME/KEY: misc_feature
<222> LOCATION: 2..2
<223> OTHER INFORMATION: Thiol
<220> FEATURE:
<221> NAME/KEY: misc_feature
<222> LOCATION: 4..4
<223> OTHER INFORMATION: Guanidine-Bridged Nucleic Acid
<220> FEATURE:
<221> NAME/KEY: misc_feature
<222> LOCATION: 7..7
<223> OTHER INFORMATION: Guanidine-Bridged Nucleic Acid
<220> FEATURE:
<221> NAME/KEY: misc_feature
<222> LOCATION: 11..11
<223> OTHER INFORMATION: Guanidine-Bridged Nucleic Acid

<400> SEQUENCE: 40 nntnttnttnt                                                          12

<210> SEQ ID NO 41
<211> LENGTH: 12
<212> TYPE: DNA
<213> ORGANISM: Artificial
<220> FEATURE:
<223> OTHER INFORMATION: Compound 56
<220> FEATURE:
<221> NAME/KEY: misc_feature
<222> LOCATION: 1..1
<223> OTHER INFORMATION: Alexa Fluor 488
<220> FEATURE:
<221> NAME/KEY: misc_feature
<222> LOCATION: 2..2
<223> OTHER INFORMATION: Thiol
<220> FEATURE:
<221> NAME/KEY: misc_feature
<222> LOCATION: 9..9
<223> OTHER INFORMATION: Guanidine-Bridged Nucleic Acid
<220> FEATURE:
<221> NAME/KEY: misc_feature
<222> LOCATION: 10..10
<223> OTHER INFORMATION: Guanidine-Bridged Nucleic Acid
<220> FEATURE:
<221> NAME/KEY: misc_feature
<222> LOCATION: 11..11
<223> OTHER INFORMATION: Guanidine-Bridged Nucleic Acid

<400> SEQUENCE: 41 nnttttttnnnt                                                         12
```

-continued

```
<210> SEQ ID NO 42
<211> LENGTH: 12
<212> TYPE: DNA
<213> ORGANISM: Artificial
<220> FEATURE:
<223> OTHER INFORMATION: Compound 57
<220> FEATURE:
<221> NAME/KEY: misc_feature
<222> LOCATION: 1..1
<223> OTHER INFORMATION: Alexa Fluor 488
<220> FEATURE:
<221> NAME/KEY: misc_feature
<222> LOCATION: 2..2
<223> OTHER INFORMATION: Thiol
<220> FEATURE:
<221> NAME/KEY: misc_feature
<222> LOCATION: 4..4
<223> OTHER INFORMATION: Guanidine-Bridged Nucleic Acid
<220> FEATURE:
<221> NAME/KEY: misc_feature
<222> LOCATION: 5..5
<223> OTHER INFORMATION: Guanidine-Bridged Nucleic Acid
<220> FEATURE:
<221> NAME/KEY: misc_feature
<222> LOCATION: 7..7
<223> OTHER INFORMATION: Guanidine-Bridged Nucleic Acid
<220> FEATURE:
<221> NAME/KEY: misc_feature
<222> LOCATION: 8..8
<223> OTHER INFORMATION: Guanidine-Bridged Nucleic Acid
<220> FEATURE:
<221> NAME/KEY: misc_feature
<222> LOCATION: 10..10
<223> OTHER INFORMATION: Guanidine-Bridged Nucleic Acid
<220> FEATURE:
<221> NAME/KEY: misc_feature
<222> LOCATION: 11..11
<223> OTHER INFORMATION: Guanidine-Bridged Nucleic Acid

<400> SEQUENCE: 42 nntnntnntnnt                                                          12

<210> SEQ ID NO 43
<211> LENGTH: 12
<212> TYPE: DNA
<213> ORGANISM: Artificial
<220> FEATURE:
<223> OTHER INFORMATION: Compound 58
<220> FEATURE:
<221> NAME/KEY: misc_feature
<222> LOCATION: 1..1
<223> OTHER INFORMATION: Alexa Fluor 488
<220> FEATURE:
<221> NAME/KEY: misc_feature
<222> LOCATION: 2..2
<223> OTHER INFORMATION: Thiol
<220> FEATURE:
<221> NAME/KEY: misc_feature
<222> LOCATION: 8..8
<223> OTHER INFORMATION: 2',4'-BNA/LNA

<400> SEQUENCE: 43 nnttttttntttt                                                         12

<210> SEQ ID NO 44
<211> LENGTH: 12
<212> TYPE: DNA
<213> ORGANISM: Artificial
<220> FEATURE:
<223> OTHER INFORMATION: Compound 59
<220> FEATURE:
<221> NAME/KEY: misc_feature
<222> LOCATION: 1..1
<223> OTHER INFORMATION: Alexa Fluor 488
<220> FEATURE:
```

```
<221> NAME/KEY: misc_feature
<222> LOCATION: 2..2
<223> OTHER INFORMATION: Thiol
<220> FEATURE:
<221> NAME/KEY: misc_feature
<222> LOCATION: 4..4
<223> OTHER INFORMATION: 2',4'-BNA/LNA
<220> FEATURE:
<221> NAME/KEY: misc_feature
<222> LOCATION: 7..7
<223> OTHER INFORMATION: 2',4'-BNA/LNA
<220> FEATURE:
<221> NAME/KEY: misc_feature
<222> LOCATION: 11..11
<223> OTHER INFORMATION: 2',4'-BNA/LNA

<400> SEQUENCE: 44 nntnttntttnt                                                         12

<210> SEQ ID NO 45
<211> LENGTH: 12
<212> TYPE: DNA
<213> ORGANISM: Artificial
<220> FEATURE:
<223> OTHER INFORMATION: Compound 60
<220> FEATURE:
<221> NAME/KEY: misc_feature
<222> LOCATION: 1..1
<223> OTHER INFORMATION: Alexa Fluor 488
<220> FEATURE:
<221> NAME/KEY: misc_feature
<222> LOCATION: 2..2
<223> OTHER INFORMATION: Thiol
<220> FEATURE:
<221> NAME/KEY: misc_feature
<222> LOCATION: 9..9
<223> OTHER INFORMATION: 2',4'-BNA/LNA
<220> FEATURE:
<221> NAME/KEY: misc_feature
<222> LOCATION: 10..10
<223> OTHER INFORMATION: 2',4'-BNA/LNA
<220> FEATURE:
<221> NAME/KEY: misc_feature
<222> LOCATION: 11..11
<223> OTHER INFORMATION: 2',4'-BNA/LNA

<400> SEQUENCE: 45 nnttttttnnnt                                                         12

<210> SEQ ID NO 46
<211> LENGTH: 12
<212> TYPE: DNA
<213> ORGANISM: Artificial
<220> FEATURE:
<223> OTHER INFORMATION: Compound 61
<220> FEATURE:
<221> NAME/KEY: misc_feature
<222> LOCATION: 1..1
<223> OTHER INFORMATION: Alexa Fluor 488
<220> FEATURE:
<221> NAME/KEY: misc_feature
<222> LOCATION: 2..2
<223> OTHER INFORMATION: Thiol
<220> FEATURE:
<221> NAME/KEY: misc_feature
<222> LOCATION: 4..4
<223> OTHER INFORMATION: 2',4'-BNA/LNA
<220> FEATURE:
<221> NAME/KEY: misc_feature
<222> LOCATION: 5..5
<223> OTHER INFORMATION: 2',4'-BNA/LNA
<220> FEATURE:
<221> NAME/KEY: misc_feature
<222> LOCATION: 7..7
<223> OTHER INFORMATION: 2',4'-BNA/LNA
```

```
<220> FEATURE:
<221> NAME/KEY: misc_feature
<222> LOCATION: 8..8
<223> OTHER INFORMATION: 2',4'-BNA/LNA
<220> FEATURE:
<221> NAME/KEY: misc_feature
<222> LOCATION: 10..10
<223> OTHER INFORMATION: 2',4'-BNA/LNA
<220> FEATURE:
<221> NAME/KEY: misc_feature
<222> LOCATION: 11..11
<223> OTHER INFORMATION: 2',4'-BNA/LNA

<400> SEQUENCE: 46 nntnntnntnnt                                                     12
```

OLIGONUCLEOTIDE AND ARTIFICIAL NUCLEOSIDE HAVING GUANIDINE BRIDGE

CROSS-REFERENCE TO RELATED APPLICATION

The present application is a U.S. National Stage Application under USC § 371 claiming benefit of International Application No. PCT/JP2013/075370, filed 19 Sep. 2013, published as WO 2014/046212 A1 on 27 Mar. 2014, which in turn claims priority to Japanese Application No. 2012-208906, filed 21 Sep. 2012 and Japanese Application No. 2013-022360 filed 7 Feb. 2013, the entirety of each of which are incorporated herein by reference.

REFERENCE TO ELECTRONIC SEQUENCE LISTING

The contents of the electronic sequence listing (2018-12-21_NANJP0132WOUS_Sequence_Listing; Size: 16,400 bytes; and Date of Creation: Dec. 21, 2018) is herein incorporated by reference in its entirety.

TECHNICAL FIELD

The present invention relates to artificial nucleosides and oligonucleotides, and more specifically relates to guanidine-bridged artificial nucleosides and oligonucleotides.

BACKGROUND ART

Examples of methods for treating diseases using nucleic acid drugs include antisense therapies, antigene therapies, aptamer-based therapies, siRNA-based therapies, and the like. Of these, the antisense therapies are approaches for treating or preventing diseases, involving inhibiting a translation process of pathogenic RNAs by externally introducing oligonucleotides (antisense strands) that are complementary to disease-associated mRNAs to form double strands. The siRNA-based therapies are similar to the antisense therapies, involving inhibiting translation from mRNAs to proteins by administering double-stranded RNAs into a living body. Meanwhile, the antigene therapies suppress transcription from DNAs to RNAs by externally introducing triplex-forming oligonucleotides corresponding to DNA sites that are to be transcribed into pathogenic RNAs. Since aptamers are short nucleic acid molecules (oligonucleotides), they function as being bound to biological components such as disease-associated proteins.

Although various artificial nucleic acids have been developed as materials for such nucleic acid drugs, no ideal molecule has been found yet. Examples of the materials developed for nucleic acid drugs to date include phosphorothioate (S—$PO_3$) oligonucleotide (S-oligo), 2',4'-bridged nucleic acid (BNA)/2',4'-locked nucleic acid (LNA) (Patent Documents 1 to 4 and Non-Patent Documents 1 to 4), and the like. S-oligo is commercially available in the United States as an antisense drug for cytomegalovirus. S-oligo has a high nuclease resistance, but is problematic and needs improvement in that its binding affinity to the target nucleic acid strands is low. 2',4'-BNA/LNA developed to date has a high binding affinity to the target nucleic acid strands, and provides the most promising molecules as the materials for the future nucleic acid drugs. However, there is still room for improvement in that the nuclease resistance is not sufficient and the stability in a living body is poor.

CITATION LIST

Patent Literature

Patent Literature 1: WO 98/39352
Patent Literature 2: WO 2005/021570
Patent Literature 3: WO 2003/068795
Patent Literature 4: WO 2011/052436

Non Patent Literature

Non Patent Literature 1: C. Wahlestedt et al., Proc. Natl. Acad. Sci. USA, 2000, Vol. 97, No. 10, pp. 5633-5638
Non Patent Literature 2: Y. Hari et al., Bioorg. Med. Chem., 2006, Vol. 14, pp. 1029-1038
Non Patent Literature 3: K. Miyashita et al., Chem. Commun., 2007, pp. 3765-3767
Non Patent Literature 4: S. M. A. Rahman et al, J. Am. Chem. Soc., 2008, Vol., 130, No. 14, pp. 4886-4896
Non Patent Literature 5: M. Kuwahara et al., Nucleic Acids Res., 2008, Vol. 36, No. 13, pp. 4257-4265
Non Patent Literature 6: S. Obika et al., Bioorg. Med. Chem., 2001, Vol. 9, pp. 1001-1011

SUMMARY OF INVENTION

Problems to be Solved by the Invention

It is an object of the present invention to provide a nucleic acid molecule for an oligonucleotide having a high binding affinity and a high specificity to a target nucleic acid and exhibiting a high nuclease resistance.

Means for Solving the Problems

The present inventors accomplished the present invention on the basis of the finding that an oligonucleotide containing a nucleic acid obtained by introducing guanidine to a bridge structure of 2',4'-BNA/LNA particularly has a high binding affinity and a high specificity to DNAs and exhibits a high nuclease resistance.

The present invention provides a compound represented by formula I or II below or a salt thereof:

[Chemical 1]

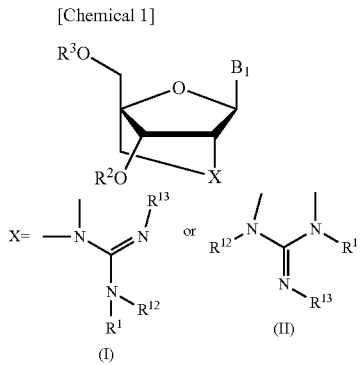

wherein $B_1$ represents:
a purin-9-yl group;
a 2-oxo-1,2-dihydropyrimidin-1-yl group;

a purin-9-yl group that has any one or more substituents selected from the group consisting of a hydroxyl group, a hydroxyl group protected by a protecting group in nucleic acid synthesis, a $C_1$ to $C_6$ linear alkyl group, a $C_1$ to $C_6$ linear alkoxy group, a mercapto group, a mercapto group protected by a protecting group in nucleic acid synthesis, a $C_1$ to $C_6$ linear alkylthio group, an amino group, a $C_1$ to $C_6$ linear alkylamino group, an amino group protected by a protecting group in nucleic acid synthesis, and a halogen atom; or a 2-oxo-1,2-dihydropyrimidin-1-yl group that has any one or more substituents selected from the group consisting of a hydroxyl group, a hydroxyl group protected by a protecting group in nucleic acid synthesis, a $C_1$ to $C_6$ linear alkyl group, a $C_1$ to $C_6$ linear alkoxy group, a mercapto group, a mercapto group protected by a protecting group in nucleic acid synthesis, a $C_1$ to $C_6$ linear alkylthio group, an amino group, a $C_1$ to $C_6$ linear alkylamino group, an amino group protected by a protecting group in nucleic acid synthesis, and a halogen atom;

$R^1$, $R^{12}$, and $R^{13}$ each independently represent a hydrogen atom, a $C_1$ to $C_7$ alkyl group that may be branched or form a ring, a protecting group for an amino group, or

[Chemical 2]

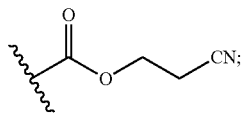

and $R^2$ and $R^3$ each independently represent a hydrogen atom, a protecting group for a hydroxyl group in nucleic acid synthesis, a $C_1$ to $C_7$ alkyl group that is a straight chain, a branched chain or up to a $C_7$ ring, a $C_2$ to $C_7$ alkenyl group that is a straight chain, a branched chain or up to a $C_7$ ring, a $C_6$ to $C_{12}$ aryl group, a $C_6$ to $C_{12}$ aryl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom, a $C_6$ to $C_{12}$ aryl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom, an aralkyl group having a $C_6$ to $C_{12}$ aryl moiety, an aralkyl group having a $C_6$ to $C_{12}$ aryl moiety that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom, an aralkyl group having a $C_6$ to $C_{12}$ aryl moiety, an aralkyl group having a $C_6$ to $C_{12}$ aryl moiety that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom, an acyl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a $C_1$ to $C_6$ linear alkylthio group, a $C_1$ to $C_6$ linear alkylamino group, an amino group protected by a protecting group in nucleic acid synthesis, and a halogen atom, a silyl group that has three substituents selected from the group consisting of a hydroxyl group protected by a protecting group in nucleic acid synthesis, a $C_1$ to $C_6$ linear alkyl group, a $C_1$ to $C_6$ linear alkoxy group, a $C_1$ to $C_6$ linear alkylamino group, and an amino group protected by a protecting group in nucleic acid synthesis, a phosphate group, a phosphate group that has any one or more substituents selected from the group consisting of a $C_1$ to $C_6$ linear alkyl group, and a $C_1$ to $C_6$ linear alkoxy group, a phosphate group protected by a protecting group in nucleic acid synthesis, or —P($R^4$)$R^5$, wherein $R^4$ and $R^5$ each independently represent a hydroxyl group protected by a protecting group in nucleic acid synthesis, a $C_1$ to $C_5$ alkoxy group, a $C_1$ to $C_6$ cyanoalkoxy group, or a dialkylamino group substituted with two $C_1$ to $C_6$ alkyl groups.

In one embodiment, in formula I or II above, $B_1$ represents a 6-aminopurin-9-yl group, a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group, a 4-amino-2-oxo-5-fluoro-1,2-dihydropyrimidin-1-yl group, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group, a 2-oxo-4-hydroxy-5-methyl-1,2-dihydropyrimidin-1-yl group, or a 4-amino-5-methyl-2-oxo-1,2-dihydropyrimidin-1-yl group.

In one embodiment, in formula I or II above, $B_1$ represents a 2-oxo-4-hydroxy-5-methyl-1,2-dihydropyrimidin-1-yl group.

The present invention also provides an oligonucleotide synthesized with at least one of the compounds represented by formula I or II below or a pharmacologically acceptable salt thereof:

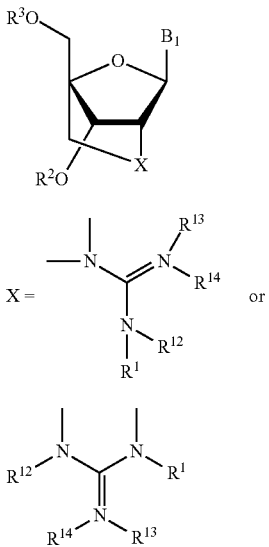

(I)

X = or (II)

wherein $B_1$ represents a purin-9-yl group;

a 2-oxo-1,2-dihydropyrimidin-1-yl group;

a purin-9-yl group that has any one or more substituents selected from the group consisting of a hydroxyl group, a hydroxyl group protected by a protecting group in nucleic acid synthesis, a $C_1$ to $C_6$ linear alkyl group, a $C_1$ to $C_6$ linear alkoxy group, a mercapto group, a mercapto group protected by a protecting group in nucleic acid synthesis, a $C_1$ to $C_6$ linear alkylthio group, an amino group, a $C_1$ to $C_6$ linear alkylamino group, an amino group protected by a protecting group in nucleic acid synthesis, and a halogen atom; or a 2-oxo-1,2-dihydropyrimidin-1-yl group that has any one or more substituents selected from the group consisting of a hydroxyl group, a hydroxyl group protected by a protecting group in nucleic acid synthesis, a $C_1$ to $C_6$ linear alkyl group, a $C_1$ to $C_6$ linear alkoxy group, a mercapto group, a mercapto group protected by a protecting group in nucleic acid synthesis, a $C_1$ to $C_6$ linear alkylthio group, an amino group, a $C_1$ to $C_6$ linear alkylamino group, an amino group protected by a protecting group in nucleic acid synthesis, and a halogen atom;

$R^1$, $R^{12}$, and $R^{13}$ each independently represent a hydrogen atom, a $C_1$ to $C_7$ alkyl group that may be branched or form a ring, a protecting group for an amino group, or

[Chemical 4]

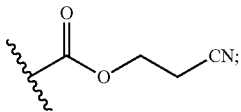

$R^2$ and $R^3$ each independently represent a hydrogen atom, a protecting group for a hydroxyl group in nucleic acid synthesis, a $C_1$ to $C_7$ alkyl group that is a straight chain, a branched chain or up to a $C_7$ ring, a $C_2$ to $C_7$ alkenyl group that is a straight chain, a branched chain or up to a $C_7$ ring, a $C_6$ to $C_{12}$ aryl group, a $C_6$ to $C_{12}$ aryl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom, a $C_6$ to $C_{12}$ aryl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom, an aralkyl group having a $C_6$ to $C_{12}$ aryl moiety, an aralkyl group having a $C_6$ to $C_{12}$ aryl moiety that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom, an aralkyl group having a $C_6$ to $C_{12}$ aryl moiety, an aralkyl group having a $C_6$ to $C_{12}$ aryl moiety that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom, an acyl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a $C_1$ to $C_6$ linear alkylthio group, a $C_1$ to $C_6$ linear alkylamino group, an amino group protected by a protecting group in nucleic acid synthesis, and a halogen atom, a silyl group that has three substituents selected from the group consisting of a hydroxyl group protected by a protecting group in nucleic acid synthesis, a $C_1$ to $C_6$ linear alkyl group, a $C_1$ to $C_6$ linear alkoxy group, a $C_1$ to $C_6$ linear alkylamino group, and an amino group protected by a protecting group in nucleic acid synthesis, a phosphate group, a phosphate group that has any one or more substituents selected from the group consisting of a $C_1$ to $C_6$ linear alkyl group, and a $C_1$ to $C_6$ linear alkoxy group, a phosphate group protected by a protecting group in nucleic acid synthesis, or —P($R^4$)$R^5$, wherein $R^4$ and $R^5$ each independently represent a hydroxyl group protected by a protecting group in nucleic acid synthesis, a $C_1$ to $C_5$ alkoxy group, a $C_1$ to $C_6$ cyanoalkoxy group, or a dialkylamino group substituted with two $C_1$ to $C_6$ alkyl groups).

In one embodiment, in formula I or II above, $B_1$ represents a 6-aminopurin-9-yl group, a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group, a 4-amino-2-oxo-5-fluoro-1,2-dihydropyrimidin-1-yl group, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group, a 2-oxo-4-hydroxy-5-methyl-1,2-dihydropyrimidin-1-yl group, or a 4-amino-5-methyl-2-oxo-1,2-dihydropyrimidin-1-yl group.

In one embodiment, in formula I or II above, $B_1$ represents a 2-oxo-4-hydroxy-5-methyl-1,2-dihydropyrimidin-1-yl group.

Effects of the Invention

The present invention can provide a nucleic acid molecule for an oligonucleotide having a high binding affinity and a high specificity to a target nucleic acid and exhibiting a high nuclease resistance.

BRIEF DESCRIPTION OF DRAWINGS

FIG. 1 is a graph showing a change over time in the percentage of unreacted oligonucleotides when various oligonucleotides having the sequence, SEQ ID No. 29: 5'-d(TTTTTTTTXT)-3' were treated with 3'-exonuclease.

FIG. 2 is a graph showing a change over time in the percentage of unreacted oligonucleotides when various oligonucleotides having the sequence 5'-d(TTTTTTTTX)-3' were treated with 3'-exonuclease.

FIG. 3 is a graph showing Tm curves of an oligonucleotide analog containing a guanidine-bridged artificial nucleic acid and an oligonucleotide containing an LNA, with respect to DNA target strands having a fully complementary sequence (full-match) and DNA target strands having a single-base mismatch (mismatch).

FIG. 4 shows microphotographs of cell penetration of Compound 57 (A to D) and Compound 61 (E to H) in HuH-7 cells: where A and E are phase-contrast images; B and F are fluorescence images using Alexa Fluor 488 (oligonucleotides); C and G are fluorescence images of Hoechst 33342 (nuclei); and D and H are fluorescence images using LysoTracker (lysosomes).

FIG. 5 shows microphotographs of cell penetration of Compound 57 in HuH-7 cells, showing photographs (A to D) obtained by enlarging the region indicated by the arrow in FIG. 4B, in FIGS. 4A to 4D.

MODES FOR CARRYING OUT THE INVENTION

Hereinafter, terms used in this specification will be defined.

In this specification, the term "$C_1$ to $C_6$ linear alkyl group" refers to any linear alkyl group with 1 to 6 carbon atoms, and specific examples thereof include a methyl group, an ethyl group, an n-propyl group, an n-butyl group, an n-pentyl group, and an n-hexyl group.

In this specification, the term "$C_1$ to $C_6$ linear alkoxy group" encompasses an alkoxy group having any linear alkyl group having 1 to 6 carbon atoms. Examples thereof include a methoxy group, an ethoxy group, and an n-propoxy group.

In this specification, the term "$C_1$ to $C_6$ linear alkylthio group" encompasses an alkylthio group having any linear alkyl group with 1 to 6 carbon atoms. Examples thereof include a methylthio group, an ethylthio group, and an n-propylthio group.

In this specification, the term "$C_1$ to $C_6$ linear alkylamino group" encompasses an amino group having any one linear alkyl group with 1 to 6 carbon atoms or any two identical or different linear alkyl groups with 1 to 6 carbon atoms. Examples thereof include a methylamino group, a dimethylamino group, an ethylamino group, a methylethylamino group, and a diethylamino group.

In this specification, the term "$C_1$ to $C_7$ alkyl group that may be branched or form a ring" encompasses any linear alkyl group with 1 to 7 carbon atoms, any branched alkyl group with 3 to 7 carbon atoms having identical or different branched chains, any cyclic alkyl group with 3 to 7 carbon atoms, and any combinations thereof with 4 to 7 carbon atoms. Examples of any linear alkyl group with 1 to 7 carbon atoms include a methyl group, an ethyl group, an n-propyl group, an n-butyl group, an n-pentyl group, an n-hexyl group, and an n-heptyl group. Examples of any branched alkyl group with 3 to 7 carbon atoms having identical or different branched chains include an isopropyl group, an isobutyl group, a tert-butyl group, and an isopentyl group. Examples of any cyclic alkyl group with 3 to 7 carbon atoms include a cyclobutyl group, a cyclopentyl group, and a cyclohexyl group.

In this specification, the term "$C_2$ to $C_7$ alkenyl group that may be branched or form a ring" encompasses any linear alkenyl group with 2 to 7 carbon atoms, any branched alkenyl group with 2 to 7 carbon atoms, any cyclic alkenyl group with 3 to 7 carbon atoms, and any combinations thereof with 4 to 7 carbon atoms. Examples of any linear alkenyl group with 2 to 7 carbon atoms include an ethenyl group, a 1-propenyl group, a 2-propenyl group, a 1-butenyl group, a 2-butenyl group, a 1-pentenyl group, a 2-pentenyl group, a 3-pentenyl group, a 4-pentenyl group, and a 1-hexenyl group. Examples of any branched alkenyl group with 3 to 7 carbon atoms include an isopropenyl group, a 1-methyl-1-propenyl group, a 1-methyl-2-propenyl group, a 2-methyl-1-propenyl group, a 2-methyl-2-propenyl group, and a 1-methyl-2-butenyl group. Examples of any cyclic alkenyl group with 3 to 7 carbon atoms include a cyclobutenyl group, a cyclopentenyl group, and a cyclohexenyl group.

In this specification, the term "aryl group that may have a hetero atom" encompasses any aromatic hydrocarbon compound with 6 to 12 carbon atoms consisting of only hydrocarbon, and any heteroaromatic compound having any ring structure with 6 to 12 carbon atoms in which one or more carbon atoms forming the ring structure are substituted with identical or different hetero atoms (e.g., nitrogen atom, oxygen atom, or sulfur atom). Examples of the aromatic hydrocarbon compound with 6 to 12 carbon atoms consisting of only hydrocarbon include a phenyl group, a naphthyl group, an indenyl group, and an azulenyl group. Examples of the heteroaromatic compound include a pyridine ring, a pyrroline ring, a quinoline ring, an indoline ring, an imidazoline ring, a purine ring, and a thiophene ring. Examples of the pyridine ring include a pyrimidine ring, a piperidine ring, a quinoline ring, and an acridine ring.

In this specification, the term "aralkyl group having a heteroaryl moiety that may have a hetero atom" encompasses any aromatic hydrocarbon compound with 5 to 12 carbon atoms consisting of only hydrocarbon, and any heteroaromatic compound having any ring structure with 5 to 12 carbon atoms in which one or more carbon atoms forming the ring structure are substituted with identical or different hetero atoms (e.g., nitrogen atom, oxygen atom, or sulfur atom). Examples of the term "aralkyl group having a heteroaryl moiety that may have a hetero atom" include a benzyl group, a phenethyl group, a naphthylmethyl group, a 3-phenylpropyl group, a 2-phenylpropyl group, a 4-phenylbutyl group, a 2-phenylbutyl group, a pyridylmethyl group, an indolylmethyl group, a furylmethyl group, a thienylmethyl group, a pyrrolylmethyl group, a 2-pyridylethyl group, a 1-pyridylethyl group, and a 3-thienylpropyl group.

In this specification, examples of the term "acyl group" include an aliphatic acyl group and an aromatic acyl group. Specific examples of the aliphatic acyl group include: alkylcarbonyl groups such as a formyl group, an acetyl group, a propionyl group, a butyryl group, an isobutyryl group, a pentanoyl group, a pivaloyl group, a valeryl group, an isovaleryl group, an octanoyl group, a nonanoyl group, a decanoyl group, a 3-methylnonanoyl group, a 8-methylnonanoyl group, a 3-ethyloctanoyl group, a 3,7-dimethyloctanoyl group, an undecanoyl group, a dodecanoyl group, a tridecanoyl group, a tetradecanoyl group, a pentadecanoyl group, a hexadecanoyl group, a 1-methylpentadecanoyl group, a 14-methylpentadecanoyl group, a 13,13-dimethyltetradecanoyl group, a heptadecanoyl group, a 15-methylhexadecanoyl group, an octadecanoyl group, a 1-methylheptadecanoyl group, a nonadecanoyl group, an eicosanoyl group, and a heneicosanoyl group; carboxylated alkylcarbonyl groups such as a succinoyl group, a glutaroyl group, and an adipoyl group; carbonyl groups substituted with a $C_1$ to $C_6$ alkyl group substituted with a halogen atom such as a chloroacetyl group, a dichloroacetyl group, a trichloroacetyl group, and a trifluoroacetyl group; $C_1$ to $C_6$ alkoxyalkylcarbonyl groups such as a methoxyacetyl group; and unsaturated alkylcarbonyl groups such as an (E)-2-methyl-2-butenoyl group. Examples of the aromatic acyl group include: arylcarbonyl groups such as a benzoyl group, an α-naphthoyl group, and a β-naphthoyl group; halogenoarylcarbonyl groups such as a 2-bromobenzoyl group and a 4-chlorobenzoyl group; arylcarbonyl groups substituted with a $C_1$ to $C_6$ alkyl group such as a 2,4,6-trimethylbenzoyl group and a 4-toluoyl group; arylcarbonyl groups substituted with an $C_1$ to $C_6$ alkoxy group such as a 4-anisoyl group; carboxylated arylcarbonyl groups such as a 2-carboxybenzoyl group, a 3-carboxybenzoyl group, and a 4-carboxybenzoyl group; nitrated arylcarbonyl groups such as a 4-nitrobenzoyl group and a 2-nitrobenzoyl group; carbonylated arylcarbonyl groups substituted with a $C_1$ to $C_6$ alkoxy group such as a 2-(methoxycarbonyl)benzoyl group; and arylated arylcarbonyl groups such as a 4-phenylbenzoyl group.

In this specification, examples of the term "silyl group" include: silyl groups substituted with three $C_1$ to $C_6$ alkyl groups such as a trimethylsilyl group, a triethylsilyl group, an isopropyldimethylsilyl group, a t-butyldimethylsilyl group, a methyldiisopropylsilyl group, a methyl di-t-butylsilyl group, and a triisopropylsilyl group; and silyl groups substituted with three $C_1$ to $C_6$ alkyl groups substituted with one or two aryl groups such as a diphenylmethylsilyl group, a butyldiphenylbutylsilyl group, a diphenylisopropylsilyl group, and a phenyldiisopropylsilyl group.

In this specification, examples of the term "halogen atom" include a fluorine atom, a chlorine atom, a bromine atom, and an iodine atom.

In this specification, there is no particular limitation on the term "protecting group" in "a protecting group for an amino group in nucleic acid synthesis", "a protecting group for a hydroxyl group in nucleic acid synthesis", "a hydroxyl group protected by a protecting group in nucleic acid synthesis", "a phosphate group protected by a protecting group in nucleic acid synthesis", and "a mercapto group protected by a protecting group in nucleic acid synthesis", as long as it can stably protect an amino group, a hydroxyl group, a phosphate group or a mercapto group in nucleic acid synthesis. Specifically, the protecting group refers to those that are stable in acidic or neutral condition and may be cleaved by chemical methods such as hydrogenolysis, hydrolysis, electrolysis and photolysis. Examples of the protecting group include: a $C_1$ to $C_6$ alkyl group; a $C_1$ to $C_6$ alkenyl group; an acyl group; a tetrahydropyranyl group and a tetrahydrothiopyranyl group; a tetrahydrofuranyl group and a tetrahydrothiofuranyl group; a silyl group; a methyl group substituted with a $C_1$ to $C_6$ alkoxy group; a methyl group substituted with a $C_1$ to $C_6$ alkoxy group substituted with a $C_1$ to $C_6$ alkoxy group; a methyl group substituted with a $C_1$ to $C_6$ alkoxy group substituted with a halogen atom; an ethyl group substituted with a $C_1$ to $C_6$ alkoxy group; an ethyl group substituted with a halogen atom; a methyl group substituted with one to three aryl groups; a methyl group substituted with one to three aryl groups substituted with a $C_1$ to $C_6$ alkyl group, a $C_1$ to $C_6$ alkoxy group, a halogen atom, and/or a cyano group; a carbonyl group substituted with a $C_1$ to $C_6$ alkoxy group; an aryl group substituted with a halogen atom, a $C_1$ to $C_6$ alkoxy group, and/or a nitro group; a carbonyl group substituted with a $C_1$ to $C_6$ alkoxy group substituted with one or more halogen atoms and/or a silyl group substituted with three $C_1$ to $C_6$ alkyl groups; an alkenyloxycarbonyl group; and an aralkyloxycarbonyl group that may be substituted with an aryl group substituted with a $C_1$ to $C_6$ alkoxy group and/or a nitro group.

More specific examples of the tetrahydropyranyl group or the tetrahydrothiopyranyl group include a tetrahydropyran-2-yl group, a 3-bromotetrahydropyran-2-yl group, a 4-methoxytetrahydropyran-4-yl group, a tetrahydrothiopyran-4-yl group, and a 4-methoxytetrahydrothiopyran-4-yl group. Examples of the tetrahydrofuranyl group or the tetrahydrothiofuranyl group include a tetrahydrofuran-2-yl group and a tetrahydrothiofuran-2-yl group. Examples of the methyl group substituted with a $C_1$ to $C_6$ alkoxy group include a methoxymethyl group, a 1,1-dimethyl-1-methoxymethyl group, an ethoxymethyl group, a propoxymethyl group, an isopropoxymethyl group, a butoxymethyl group, and a t-butoxymethyl group. Examples of the methyl group substituted with a $C_1$ to $C_6$ alkoxy group substituted with a $C_1$ to $C_6$ alkoxy group include a 2-methoxyethoxymethyl group. Examples of the methyl group substituted with a $C_1$ to $C_6$ alkoxy group substituted with a halogen atom include a 2,2,2-trichloroethoxymethyl group, a bis(2-chloroethoxy)methyl group. Examples of the ethyl group substituted with a $C_1$ to $C_6$ alkoxy group include a 1-ethoxyethyl group and a 1-(isopropoxy)ethyl group. Examples of the ethyl group substituted with a halogen atom include a 2,2,2-trichloroethyl group. Examples of the methyl group substituted with one to three aryl groups include a benzyl group, an α-naphthylmethyl group, a β-naphthylmethyl group, a diphenylmethyl group, a triphenylmethyl group, an α-naphthyldiphenylmethyl group, and a 9-anthrylmethyl group. Examples of the "methyl group substituted with one to three aryl groups substituted with a $C_1$ to $C_6$ alkyl group, a $C_1$ to $C_6$ alkoxy group, a halogen atom, and/or a cyano group" include a 4-methylbenzyl group, a 2,4,6-trimethylbenzyl group, a 3,4,5-trimethylbenzyl group, a 4-methoxybenzyl group, a 4-methoxyphenyldiphenylmethyl group, a 4,4'-dimethoxytriphenylmethyl group, a 2-nitrobenzyl group, a 4-nitrobenzyl group, a 4-chlorobenzyl group, a 4-bromobenzyl group, and a 4-cyanobenzyl group. Examples of the carbonyl group substituted with a $C_1$ to $C_6$ alkoxy group include a methoxycarbonyl group, an ethoxycarbonyl group, a t-butoxycarbonyl group, and an isobutoxycarbonyl group. Examples of the "aryl group substituted with a halogen atom, a $C_1$ to $C_6$ alkoxy group, and/or a nitro group" include a 4-chlorophenyl group, a 2-fluorophenyl group, a 4-methoxyphenyl group, a 4-nitrophenyl group, and a 2,4-dinitrophenyl group. Examples of the "carbonyl group substituted with a $C_1$ to $C_6$ alkoxy group substituted with a silyl group substituted with a halogen atom and/or three $C_1$ to $C_6$ alkyl groups" include a 2,2,2-trichloroethoxycarbonyl group and a 2-trimethylsilylethoxycarbonyl group. Examples of the alkenyloxycarbonyl group include a vinyloxycarbonyl group and an aryloxycarbonyl group. Examples of the "aralkyloxycarbonyl group that may be substituted with an aryl group substituted with a $C_1$ to $C_6$ alkoxy group and/or a nitro group" include a benzyloxycarbonyl group, a 4-methoxybenzyloxycarbonyl group, a 3,4-dimethoxybenzyloxycarbonyl group, a 2-nitrobenzyloxycarbonyl group, and a 4-nitrobenzyloxycarbonyl group.

Examples of the "protecting group for a hydroxyl group in nucleic acid synthesis" include an aliphatic acyl group; an aromatic acyl group; a methyl group substituted with one to three aryl groups; a methyl group substituted with one to three aryl groups substituted with a $C_1$ to $C_6$ alkyl group, a $C_1$ to $C_6$ alkoxy group, a halogen atom, and/or a cyano group; and a silyl group. Examples of the protecting group in the "hydroxyl group protected by a protecting group in nucleic acid synthesis" include: an aliphatic acyl group; an aromatic acyl group; a methyl group substituted with one to three aryl groups; an aryl group substituted with a halogen atom, a $C_1$ to $C_6$ alkoxy group, and/or a nitro group; a $C_1$ to $C_6$ alkyl group; and a $C_1$ to $C_6$ alkenyl group. Examples of the "protecting group for an amino group in nucleic acid synthesis" include an acyl group and a benzoyl group. Examples of the "protecting group" in the "phosphate group protected by a protecting group in nucleic acid synthesis" include: a $C_1$ to $C_6$ alkyl group substituted with a $C_1$ to $C_6$ alkyl group and/or a cyano group; an aralkyl group; an aralkyl group substituted with an aryl group substituted with a nitro group and/or a halogen atom; an aryl group substituted with a $C_1$ to $C_6$ alkyl group, a halogen atom, or a nitro group; a 2-cyanoethyl group; a 2,2,2-trichloroethyl group; a benzyl group; a 2-chlorophenyl group; and a 4-chlorophenyl group. Examples of the "protecting group" in the "mercapto group protected by a protecting group in nucleic acid synthesis" include an aliphatic acyl group, an aromatic acyl group, and a benzoyl group.

In this specification, among the groups represented by $-P(R^4)R^5$ (wherein $R^4$ and $R^5$ each independently represent a hydroxyl group protected by a protecting group in nucleic acid synthesis, a mercapto group, a $C_1$ to $C_5$ alkoxy group, a $C_1$ to $C_6$ cyanoalkoxy group, or a dialkylamino group substituted with two $C_1$ to $C_6$ alkyl groups), groups in which $R^4$ can be represented by $OR^{4a}$ and $R^5$ can be represented by $N(R^{5a})_2$ are referred to as a "phosphoramidite group". Examples of the phosphoramidite group include a group represented by the formula $-P(OC_2H_4CN)(N(iPr)_2)$ and a group represented by the formula $-P(OCH_3)(N(iPr)_2)$. In these formulae, iPr represents an isopropyl group.

In this specification, the terms "artificial nucleoside" and "nucleoside analog" refer to a non-naturally occurring nucleoside in which a purine or a pyrimidine base is bound to a sugar (i.e., a nucleoside that is not a naturally occurring nucleoside and that can be only artificially produced), and a nucleoside in which a heteroaromatic ring or an aromatic hydrocarbon ring that is neither purine nor pyrimidine and that can be used in place of a purine or a pyrimidine base (e.g., there is no particular limitation, but examples thereof include pyridone, hydroxybenzene, and aminopyridine) is bound to a sugar.

In this specification, the terms "artificial oligonucleotide" and "oligonucleotide analog" refer to a non-naturally occurring derivative of "oligonucleotide" in which 2 to 50 identical or different "nucleosides" or "nucleoside analogs" are bound to each other through phosphodiester bond. Examples of such analogs include: a sugar derivative in which the sugar moiety is modified; a thioate derivative in which the phosphate diester moiety is thioated; an ester in which the terminal phosphate moiety is esterified; an amide in which the amino group on the purine base is amidated; and a sugar derivative in which the sugar moiety is modified.

In this specification, the term "a salt of a compound represented by formula I or II" refers to a salt of a compound represented by formula I or II of the present invention. Examples of such a salt include: metal salts such as alkali metal salts (e.g., sodium salts, potassium salts, and lithium salts), alkaline-earth metal salts (e.g., calcium salts and magnesium salts), aluminum salts, iron salts, zinc salts, copper salts, nickel salts, and cobalt salts of the compound represented by formula I or II; amine salts such as inorganic salts (e.g., ammonium salts) and organic salts (e.g., t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenethamine salts, chloroprocaine salts, procaine salts, diethanolamine salts, N-benzyl-phenethylamine salts, piperazine salts, tetramethylammonium salts, and tris(hydroxymethyl)aminomethane salts) of the compound represented by formula I or II; inorganic acid salts such as hydrohalides (e.g., hydrofluoride, hydrochloride, hydrobromide, and hydroiodide), nitrate, perchlorate, sulfate, and phosphate of the compound represented by formula I or II; organic acid salts such as alkanesulfonate with 1 to 6 carbon atoms (e.g., methanesulfonate, trifluoromethanesulfonate, and ethanesulfonate), arylsulfonate (e.g., benzenesulfonate and p-toluenesulfonate), acetate, malate, fumarate, succinate, citrate, tartrate, oxalate, and maleate of the compound represented by formula I or II; and amino acid salts such as glycine salts, lysine salts, arginine salts, ornithine salts, glutamate, and aspartate of the compound represented by formula I or II.

In this specification, the term "a pharmacologically acceptable salt of an oligonucleotide" refers to a salt of an oligonucleotide analog synthesized with at least one of the compounds represented by formula I or II of the present invention. Examples of such a salt include: metal salts such as alkali metal salts (e.g., sodium salts, potassium salts, and lithium salts), alkaline-earth metal salts (e.g., calcium salts and magnesium salts), aluminum salts, iron salts, zinc salts, copper salts, nickel salts, and cobalt salts of an oligonucleotide synthesized with at least one of the compounds represented by formula I or II; amine salts such as inorganic salts (e.g., ammonium salts) and organic salts (e.g., t-octylamine salts, dibenzylamine salts, morpholine salts, glucosamine salts, phenylglycine alkyl ester salts, ethylenediamine salts, N methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, and tris(hydroxymethyl)aminomethane salts) of an oligonucleotide synthesized with at least one of the compounds represented by formula I or II; inorganic acid salts such as hydrohalides (e.g., hydrofluoride, hydrochloride, hydrobromide, and hydroiodide), nitrate, perchlorate, sulfate, and phosphate of an oligonucleotide synthesized with at least one of the compounds represented by formula I or II; organic acid salts such as sulfonate substituted with alkane with 1 to 6 carbon atoms (e.g., methanesulfonate, trifluoromethanesulfonate, and ethanesulfonate), arylsulfonate (e.g., benzenesulfonate and p-toluenesulfonate), acetate, malate, fumarate, succinate, citrate, tartrate, oxalate, and maleate of an oligonucleotide synthesized with at least one of the compounds represented by formula I or II; and amino acid salts such as glycine salts, lysine salts, arginine salts, ornithine salts, glutamate, and aspartate of an oligonucleotide synthesized with at least one of the compounds represented by formula I or II.

Hereinafter, the present invention will be described in detail.

According to the present invention, 2',4'-bridged artificial nucleosides and nucleotides or salts thereof have the structures represented by formula I or II below:

[Chemical 5]

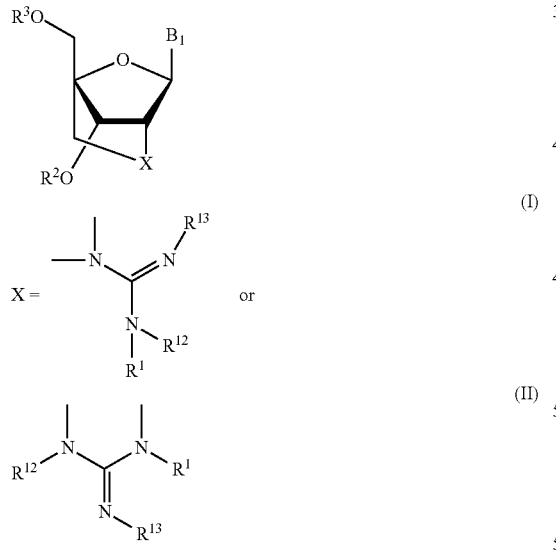

wherein $B_1$ represents
a purin-9-yl group;
a 2-oxo-1,2-dihydropyrimidin-1-yl group;
a purin-9-yl group that has any one or more substituents selected from the group consisting of a hydroxyl group, a hydroxyl group protected by a protecting group in nucleic acid synthesis, a $C_1$ to $C_6$ linear alkyl group, a $C_1$ to $C_6$ linear alkoxy group, a mercapto group, a mercapto group protected by a protecting group in nucleic acid synthesis, a $C_1$ to $C_6$ linear alkylthio group, an amino group, a $C_1$ to $C_6$ linear alkylamino group, an amino group protected by a protecting group in nucleic acid synthesis, and a halogen atom; or
a 2-oxo-1,2-dihydropyrimidin-1-yl group that has any one or more substituents selected from the group consisting of a hydroxyl group, a hydroxyl group protected by a protecting group in nucleic acid synthesis, a $C_1$ to $C_6$ linear alkyl group, a $C_1$ to $C_6$ linear alkoxy group, a mercapto group, a mercapto group protected by a protecting group in nucleic acid synthesis, a $C_1$ to $C_6$ linear alkylthio group, an amino group, a $C_1$ to $C_6$ linear alkylamino group, an amino group protected by a protecting group in nucleic acid synthesis, and a halogen atom;

$R^1$, $R^{12}$, and $R^{13}$ each independently represent a hydrogen atom, a $C_1$ to $C_7$ alkyl group that may be branched or form a ring, a protecting group for an amino group, or

[Chemical 6]

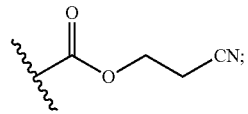

and, $R^2$ and $R^3$ each independently represent
a hydrogen atom,
a protecting group for a hydroxyl group in nucleic acid synthesis,
a $C_1$ to $C_7$ alkyl group that is a straight chain, a branched chain or up to a $C_7$ ring,
a $C_2$ to $C_7$ alkenyl group that is a straight chain, a branched chain or up to a $C_7$ ring,
a $C_6$ to $C_{12}$ aryl group,
a $C_6$ to $C_{12}$ aryl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom,
a $C_6$ to $C_{12}$ aryl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom,
an aralkyl group having a $C_6$ to $C_{12}$ aryl moiety,
an aralkyl group having a $C_6$ to $C_{12}$ aryl moiety that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom,
an aralkyl group having a $C_6$ to $C_{12}$ aryl moiety,
an aralkyl group having a $C_6$ to $C_{12}$ aryl moiety that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom, an acyl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a $C_1$ to $C_6$ linear alkylthio group, a $C_1$ to $C_6$ linear alkylamino group, an amino group protected by a protecting group in nucleic acid synthesis, and a halogen atom, a silyl group that has three substituents selected from the group consisting of a hydroxyl group protected by a protecting group in nucleic acid synthesis, a $C_1$ to $C_6$ linear alkyl group, a $C_1$ to $C_6$ linear alkoxy group, a $C_1$ to $C_6$ linear alkylamino group, and an amino group protected by a protecting group in nucleic acid synthesis, a phosphate group, a phosphate group that has any one or more substituents selected from the group consisting of a $C_1$ to $C_6$ linear alkyl group, and a $C_1$ to $C_6$ linear alkoxy group, a phosphate group protected by a protecting group in nucleic acid synthesis, or —$P(R^4)R^5$, wherein $R^4$ and $R^5$ each independently represent a hydroxyl group protected by a protecting group in nucleic acid synthesis, a $C_1$ to $C_5$ alkoxy group, a $C_1$ to $C_6$ cyanoalkoxy group, or a dialkylamino group substituted with two $C_1$ to $C_6$ alkyl groups).

In formula I or II above, $B_1$ represents a purine base (i.e., purin-9-yl group) or a pyrimidine base (i.e., 2-oxo-1,2-dihydropyrimidin-1-yl group). These bases may have any one or more substituents selected from a group α consisting of a hydroxyl group, a $C_1$ to $C_6$ linear alkyl group, a $C_1$ to $C_6$ linear alkoxy group, a mercapto group, a $C_1$ to $C_6$ linear alkylthio group, an amino group, a $C_1$ to $C_6$ linear alkylamino group, and a halogen atom.

Specific examples of the base ($B_1$) include a 6-aminopurin-9-yl group (adeninyl group), a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group (guaninyl group), a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group (cytosinyl group), a 4-amino-2-oxo-5-fluoro-1,2-dihydropyrimidin-1-yl group, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group (uracilyl group), a 2-oxo-4-hydroxy-5-methyl-1,2-dihydropyrimidin-1-yl group (thyminyl group), and a 4-amino-5-methyl-2-oxo-1,2-dihydropyrimidin-1-yl group.

Of these, for the purpose of safe and effective application to nucleic acid drugs, $B_1$ is preferably one of compounds that have the structural formulae represented as follows:

[Chemical 7]

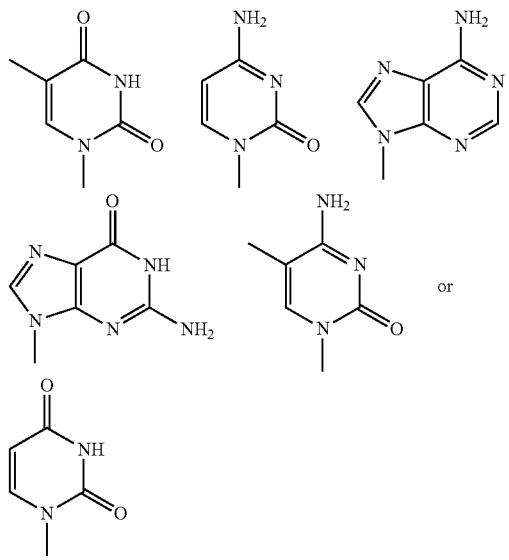

such as a 2-oxo-4-hydroxy-5-methyl-1,2-dihydropyrimidin-1-yl group (thyminyl group), a 2-oxo-4-amino-1,2-dihydropyrimidin-1-yl group (cytosinyl group), a 6-aminopurin-9-yl group (adeninyl group), a 2-amino-6-hydroxypurin-9-yl group (guaninyl group), a 4-amino-5-methyl-2-oxo-1,2-dihydropyrimidin-1-yl group, and a 2-oxo-4-hydroxy-1,2-dihydropyrimidin-1-yl group (uracilyl group), and particularly preferably a 2-oxo-4-hydroxy-5-methyl-1,2-dihydropyrimidin-1-yl group (thyminyl group). During the synthesis of the oligonucleotides, the hydroxyl group is preferably protected by the protecting group.

In formula I or II above, $R^1$, $R^{12}$, and $R^{13}$ each independently represent a hydrogen atom, a $C_1$ to $C_7$ alkyl group that may be branched or form a ring, a protecting group for an amino group, or

[Chemical 8]

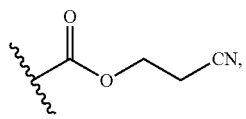

and preferably represent a hydrogen atom or a methyl group. Examples of the "protecting group for an amino group" include an acetyl group, a tert-butoxycarbonyl (Boc) group, and a 9-fluorenylmethyloxycarbonyl (Fmoc) group.

In formula I or II above, $R^2$ and $R^3$ each independently represent a hydrogen atom, a protecting group for a hydroxyl group in nucleic acid synthesis, a $C_1$ to $C_7$ alkyl group that may be branched or form a ring, a $C_2$ to $C_7$ alkenyl group that may be branched or form a ring, a $C_6$ to $C_{12}$ aryl group that may have any one or more substituents selected from the group α and that may have a hetero atom, an aralkyl group having a $C_6$ to $C_{12}$ aryl moiety that may have any one or more substituents selected from the group α and that may have a hetero atom, an acyl group that may have any one or more substituents selected from the group α, a silyl group that may have any one or more substituents selected from the group α, a phosphate group that may have any one or more substituents selected from the group α, a phosphate group protected by a protecting group in nucleic acid synthesis, or —P(R⁴)R⁵ (wherein R⁴ and R⁵ each independently represent a hydroxyl group protected by a protecting group in nucleic acid synthesis, a mercapto group, a $C_1$ to $C_5$ alkoxy group, a $C_1$ to $C_6$ cyanoalkoxy group, and/or a dialkylamino group substituted with two $C_1$ to $C_6$ alkyl groups).

The 2',4'-bridged artificial nucleoside of the present invention is obtained by introducing guanidine to a bridge structure of 2',4'-BNA/LNA. Since guanidine has positive electric charge, for example, it is expected that the ability to form a double strand with the target nucleic acid is improved due to the enhancement in the suppression of anionic repulsion (electrostatic interaction) at the phosphate diester moiety and the hydration effect and that the enzyme resistance is improved.

A 2',4'-bridged artificial nucleotide can be easily prepared from the 2',4'-bridged artificial nucleoside of the present invention. For example, the 2',4'-bridged artificial nucleotide can be easily triphosphorylated according to the method described in Non-Patent Document 5.

The oligonucleotide or a pharmacologically acceptable salt thereof of the present invention is synthesized with at least one of the compounds represented by formula I or II below:

[Chemical 9]

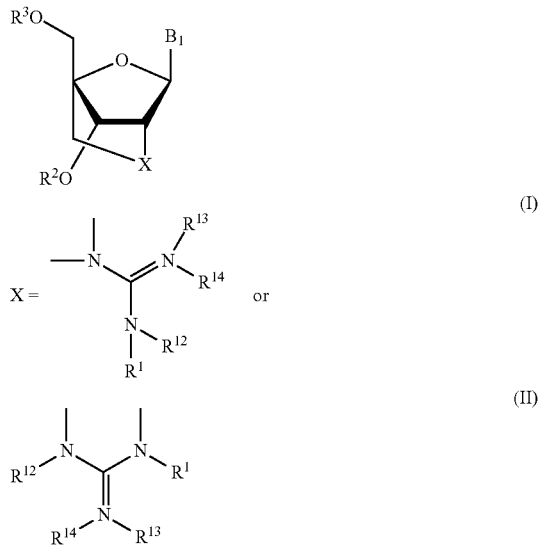

(wherein $B_1$, $R^2$, and $R^3$ are as defined above).

In formula I or II above, $R^1$, $R^{12}$, and $R^{13}$ each independently represent a hydrogen atom, a $C_1$ to $C_7$ alkyl group that may be branched or form a ring, a protecting group for an amino group, or

[Chemical 10]

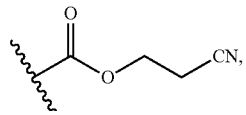

and preferably represent a hydrogen atom or a methyl group.

The oligonucleotide of the present invention has at least one nucleoside structure described above at a suitable position. There is no particular limitation on the number and position of nucleoside structures described above contained in one oligonucleotide, and they can be designed as appropriate according to the purpose. As the number of structures increases, the oligonucleotide has a higher binding affinity and a higher specificity to the target nucleic acid, exhibits higher speeds in forming double strands and triple strands, and exhibits a higher nuclease resistance. In this specification, the nucleoside structures described above contained in the 2',4'-bridged artificial nucleoside of the present invention and the oligonucleotide of the present invention may be collectively referred to as a "guanidine-bridged artificial nucleic acid" or a "guanidine-bridged nucleic acid".

The oligonucleotide containing such a nucleoside structure and an analog thereof have a fixed structure due to a bridge of the sugar moiety, and, thus, they are resistant to be degraded by various nucleases, and can remain in a living body for a long period of time after administration. Furthermore, such an oligonucleotide or an analog thereof, with the electrostatic action from the cationic guanidine existing on the bridge of the sugar moiety thereof, for example, form a stable duplex with an mRNA to inhibit biosynthesis of pathogenic protein, or form a triplex with a DNA duplex in the genome to inhibit the transcription into an mRNA. Also, it allows to suppress the proliferation of a virus that has infected a living body.

Accordingly, it is expected that the oligonucleotide and an analog thereof synthesized from the 2',4'-bridged artificial nucleoside according to the present invention are useful as pharmaceuticals (antisense molecules, etc.) for treating diseases by inhibiting the action of a specific gene, such as an antitumor agent or an antiviral agent.

In particular, in the antisense therapies, both of the binding affinity to complementary sense strand RNAs and the resistance to deoxyribonuclease in vivo are required. It is known that, typically, a nucleic acid in the form of a single strand constantly has a structural fluctuation of a sugar moiety between the form close to a sugar moiety in a DNA duplex and the form close to a sugar moiety in a DNA-RNA duplex or a RNA duplex. When a single-stranded nucleic acid forms a double strand with the complementary RNA strand, the sugar moiety structure is fixed. The 2',4'-bridged artificial nucleoside of the present invention easily forms a double strand with a target RNA strand and can stably remain, because the sugar moiety has been fixed in advance in the state of forming a double strand. It is also known that a double-stranded nucleic acid is stabilized with hydrated water with a chain-like structure referred to as a network of water molecules. Since the 2',4'-bridged artificial nucleoside of the present invention contains guanidine, for example, it is expected that the double strand-forming ability is improved due to the electrostatic interaction and the hydration effect and that the enzyme resistance is improved. Furthermore, it is expected that, when guanidine is introduced into the bridge, the positions of cations are fixed, and the electrostatic interaction and the hydration effect are enhanced. It is expected that the 2',4'-bridged artificial nucleoside of the present invention can be more efficiently taken up into cells and can more efficiently hybridize with a target nucleic acids, compared with naturally occurring nucleic acids and conventionally known artificial nucleic acids, because the 2',4'-bridged artificial nucleoside have positive electric charge derived from guanidinium groups in the molecule. Accordingly, it is expected that the antisense effect is enhanced and the retention time in the body becomes longer, and, thus, a dosage amount can be reduced to ameliorate side effects and reduce costs.

The oligonucleotide and an analog thereof of the present invention can be formulated into a parenteral preparation or a liposomal preparation, by adding an auxiliary substance usually used in the technical field of pharmaceutical formulations, such as a vehicle, a binder, an antiseptic, an oxidation stabilizer, a disintegrant, a lubricant, and a corrigent. Also, for example, it is possible to prepare a topical preparation such as a solution, a cream, and an ointment, by adding a pharmaceutical carrier usually used in this technical field.

EXAMPLES

Hereinafter, synthesis of the 2',4'-bridged artificial nucleoside and an analog thereof of the present invention will be described in more detail by way of examples.

In the following examples, hydrogen nuclear magnetic resonance ($^1$H-NMR) spectra were measured with a JNM-ECS400 (400 MHz) (manufactured by JEOL Ltd.) using tetramethylsilane (0.00 ppm), chloroform-d (7.26 ppm), and methanol-$d_4$ (3.30 ppm), as internal standard. Splitting patterns were expressed such that singlet, doublet, triplet, multiplet, AB quartet, and doublet of doublets were respectively abbreviated as s, d, t, m, AB, and dd. Carbon nuclear magnetic resonance ($^{13}$C-NMR) spectra were measured with a JNM-ECS400 (100 MHz) using chloroform-d (77.0 ppm) and methanol-$d_4$ (49.0 ppm) as internal standard. Phosphorus nuclear magnetic resonance ($^{31}$P-NMR) measurement was performed with a JNM-ECS400 (161.8 MHz) (manufactured by JEOL Ltd.) using 5% phosphoric acid-deuterium oxide solution (0.00 ppm) as external standard. Mass spectrometry (FAB-MS) was performed with a JMS-600, a JMS-700, and a JMS-D300 (manufactured by JEOL Ltd.). Silica gel chromatography was performed using an absorbent PSQ-100B (ave. 0.110 mm) (manufactured by Fuji Silysia Chemical Ltd.), and flash silica gel chromatography was performed using an absorbent PSQ-60B (ave. 0.060 mm) (manufactured by Fuji Silysia Chemical Ltd.). High performance liquid chromatography (HPLC) was performed using a Shimadzu LC-10AT$_{VP}$, a Shimadzu SPD-10A$_{VP}$, and a Shimadzu CTO-10$_{VP}$ (manufactured by Shimadzu Corporation). In the HPLC, an analytical column used was a Waters XBridge™ OST C18 2.5 µm (4.6×50 mm), and a preparative column used was a Waters XBridge™ OST C18 2.5 µm (10×50 mm). Tm measurement was performed using a Shimadzu UV-1650B and a Shimadzu UV-1650PC (manufactured by Shimadzu Corporation). MALDI-TOF-MS measurement was performed using a Daltonics (registered trademark) Autoflex II TOF/TOF (manufactured by Bruker).

Methylene chloride, dimethylformamide (DMF), tetrahydrofuran (THF), acetonitrile, and pyridine were used as reaction solvents and bases after being dried over calcium hydride and distilled. As the other reagents, those commercially available were used as they were, unless otherwise specified.

Example 1: Synthesis of Nucleoside Analog (Compound 8)

[Chemical 11]

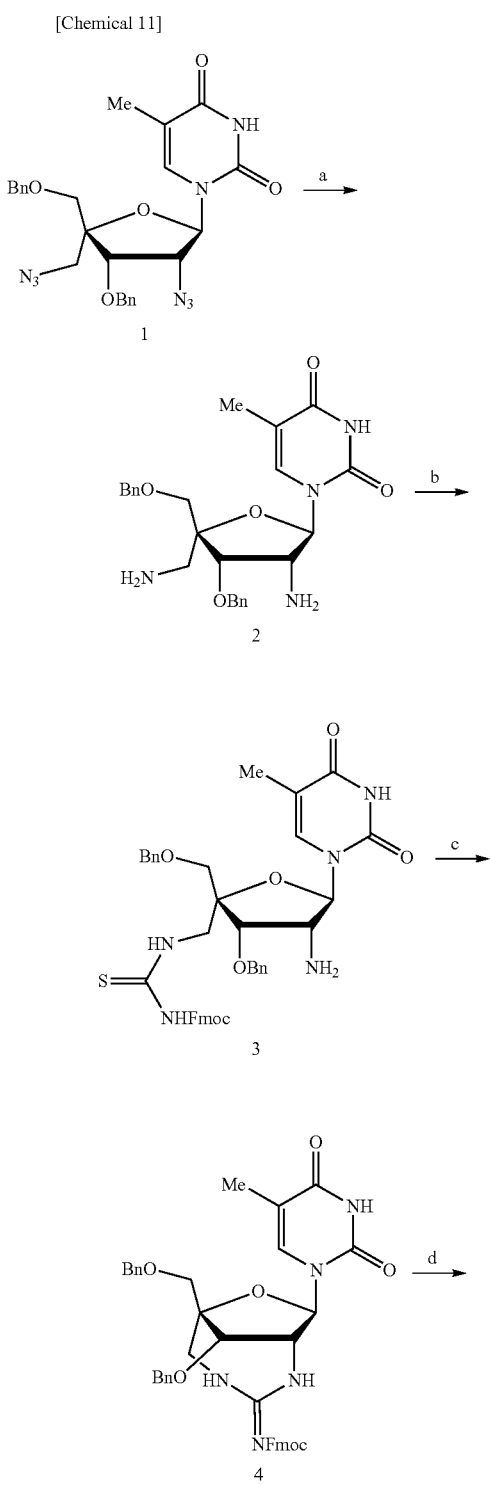

21
-continued
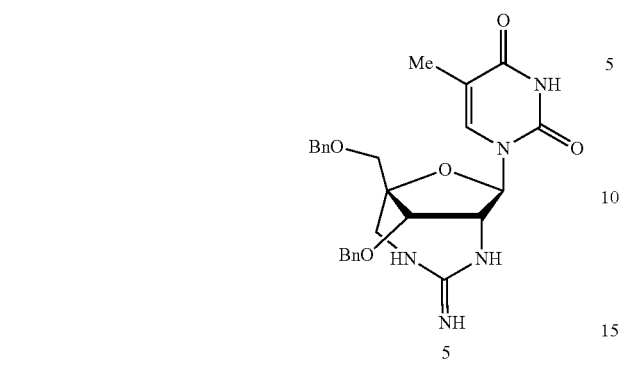
5
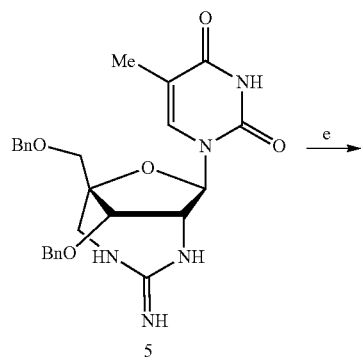
5
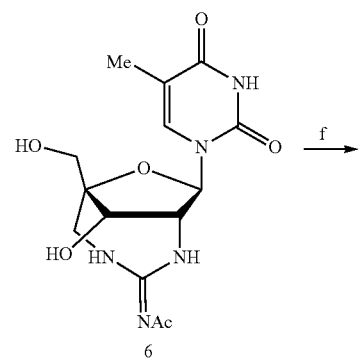
6
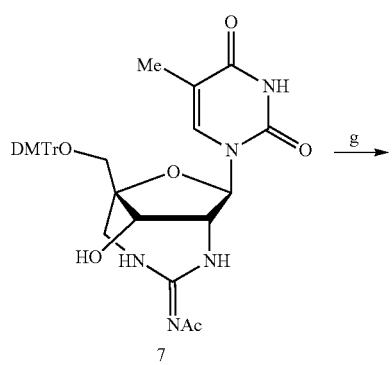
7
22
-continued
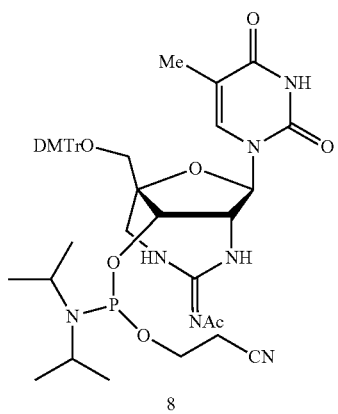
8
(1) Synthesis of Compound 5
[Chemical 12]
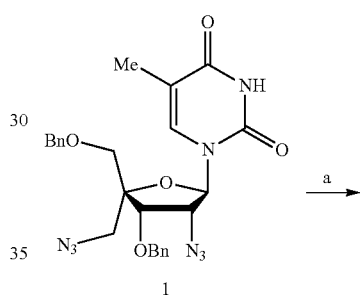
1
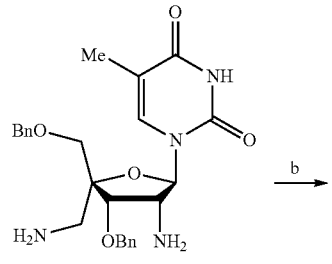
2
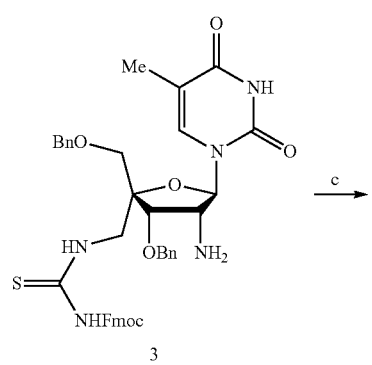
3

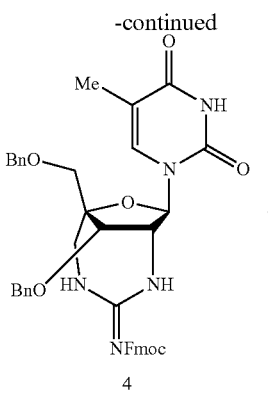

4

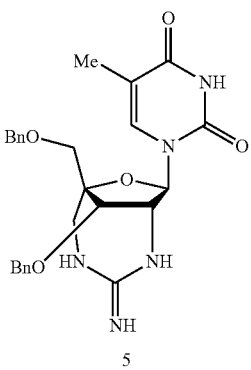

5

Compound 1 was synthesized in 15 steps from D-glucose according to the method described in Chem. Commun. (Nishida, M. et al., 2010, vol. 46, p. 5283-5285).

Nickel chloride (36 mg, 0.28 mmol) was added to 50 mL of methanol solution containing the obtained Compound 1 (2.00 mg, 3.86 mmol) in a nitrogen gas flow, and sodium borohydride (600 mg, 15.4 mmol) was further added thereto at 0° C., after which the mixture was stirred at room temperature for 10 minutes. After the mixture was filtered through celite, the solvent was evaporated off to obtain a crude product. The obtained crude product was purified by silica gel column chromatography (methanol) to obtain Compound 2 (1.47 g, 81%) as a white amorphous (Step a).

The physical property data of the obtained Compound 2 was as follows: $^1$H-NMR (CD$_3$OD) δ: 1.60 (3H, d, J=1.0 Hz), 2.61, 2.93 (2H, AB, J=14.0 Hz), 3.54, 3.61 (2H, AB, J=10.0 Hz), 3.70 (1H, t, J=6.0 Hz, 9.0 Hz), 4.19 (1H, d, J=6.0 Hz), 4.58, 4.61 (2H, AB, J=11.5 Hz), 4.65, 4.81 (2H, AB, J=11.0 Hz), 5.89 (1H, d, J=9.0 Hz), 7.30-7.43 (10H, m), 7.53 (1H, d, J=1.0 Hz).

Next, a dichloromethane solution (4 mL) containing 9-fluorenylmethoxycarbonyl isocyanate (350 mg, 1.23 mmol) was added to 10 mL of dichloromethane solution containing the obtained Compound 2 (576 mg, 1.23 mmol) in a nitrogen gas flow at 0° C., after which the mixture was stirred at 0° C. for 15 minutes. Next, after the reaction was quenched by adding water at 0° C., the reaction liquid was extracted with dichloromethane, and the organic layer was washed with water and saturated saline and dried over anhydrous sodium sulfate. Next, the solvent was evaporated off to obtain a crude product. The obtained crude product was purified by silica gel column chromatography (chloroform:methanol=80:1) to obtain Compound 3 (638 mg, 69%) as a white solid (Step b).

The physical property data of the obtained Compound 3 was as follows: $^1$H-NMR (CDCl$_3$) δ: 1.57 (3H, d, J=1.0 Hz), 3.57, 3.69 (2H, AB, J=10.0 Hz), 3.65 (1H, t, J=7.5 Hz), 3.91, 4.24 (2H, AB, J=12.0 Hz), 4.16 (1H, d, J=7.5 Hz), 4.22 (1H, t, J=7.0 Hz), 4.46 (2H, d, J=7.0 Hz), 4.53 (2H, s), 4.68, 4.77 (2H, AB, J=11.0 Hz), 5.88 (1H, d, J=7.5 Hz), 7.19-7.44 (15H, m), 7.55 (1H, d, J=7.5 Hz), 7.78 (1H, d, J=8.0 Hz), 8.12 (1H, s), 8.29 (1H, s), 9.98 (1H, s).

Next, 1-ethyl-3-(3-dimethylaminopropyl)carbodiimide hydrochloride (103 mg, 0.54 mmol) was added to 5 mL of dichloromethane solution containing the obtained Compound 3 (335 mg, 0.45 mmol) in a nitrogen gas flow, after which the mixture was stirred at room temperature for 6 hours. Next, after the reaction was quenched by adding water at 0° C., the reacted liquid was extracted with dichloromethane, and the organic layer was washed with water and saturated saline and dried over anhydrous sodium sulfate. Next, the solvent was evaporated off to obtain a crude product. The obtained crude product was purified by silica gel column chromatography (chloroform:methanol=80:1) to obtain Compound 4 (268 mg, 83%) as a yellowish white solid (Step c).

The physical property data of the obtained Compound 4 was as follows: $^1$H-NMR (CD$_3$OD) δ: 1.35 (3H, s), 3.11, 3.45 (2H, AB, J=13.5 Hz), 3.69, 3.83 (2H, AB, J=11.0 Hz), 4.28 (2H, d, J=6.5 Hz), 4.30 (1H, d, J=6.5 Hz), 4.32 (1H, t, J=6.5 Hz), 4.38 (1H, d, J=6.5 Hz), 4.48, 4.71 (2H, AB, J=11.5 Hz), 4.51, 4.57 (2H, AB, J=11.0 Hz), 5.91 (1H, s), 7.23-7.85 (19H, m).

Diethylamine (2 mL) was added to 8 mL of dichloromethane solution containing the obtained Compound 4 (971 mg, 1.36 mmol) in a nitrogen gas flow, after which the mixture was stirred at room temperature for 5 hours. Next, after the solvent was evaporated off, the obtained product was washed with hexane to obtain Compound 5 (609 mg, 91%) as a white solid (Step d).

The physical property data of the obtained Compound 5 was as follows: $^1$H-NMR (CD$_3$OD) δ: 1.37 (3H, s), 3.12, 3.46 (2H, AB, J=14.0 Hz), 3.60, 3.86 (2H, AB, J=11.0 Hz), 4.25 (1H, d, J=6.5 Hz), 4.44 (1H, d, J=6.5 Hz), 4.50, 4.71 (2H, AB, J=11.5 Hz), 4.51, 4.59 (2H, AB, J=11.0 Hz), 5.89 (1H, s), 7.24-7.80 (10H, m), 7.89 (1H, s).

(2) Synthesis of Compound 8

[Chemical 13]

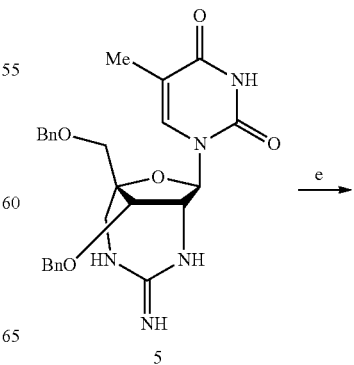

5

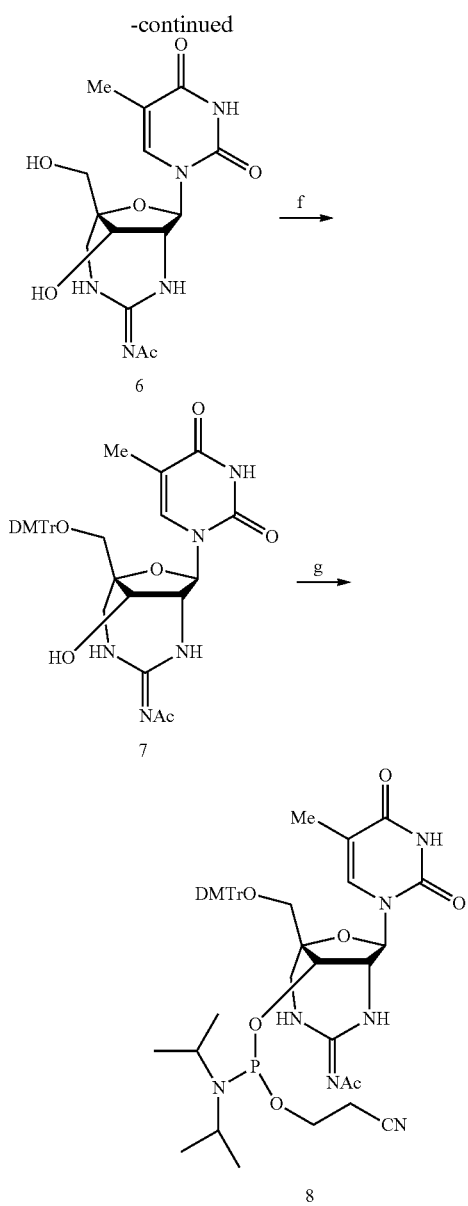

Triethylamine (0.68 mL, 4.93 mmol) was added to 12 mL of dichloromethane solution containing the obtained Compound 5 (551 mg, 1.12 mmol) in a nitrogen gas flow at room temperature, and acetic anhydride (0.23 mL, 2.47 mmol) was further added thereto at 0° C., after which the mixture was stirred at room temperature for 2 hours. Next, after the reaction was quenched by adding saturated sodium bicarbonate solution to the reacted liquid at 0° C., the reacted liquid was extracted with dichloromethane, and the organic layer was washed with water and saturated saline and dried over anhydrous sodium sulfate. Next, the solvent was evaporated off to obtain a crude product. Potassium carbonate (400 mg, 2.89 mmol) was added to 10 mL of isopropanol solution containing the obtained crude product (616 mg), after which the mixture was stirred at room temperature for 6 days. Next, after the reaction was quenched by adding water at 0° C., the reacted liquid was extracted with dichloromethane, and the organic layer was washed with water and saturated saline and dried over anhydrous sodium sulfate. Next, the solvent was evaporated off to obtain a crude product. Palladium hydroxide on carbon (1.40 g) was added to 10 mL of isopropanol solution containing the obtained crude product (517 mg) in a hydrogen gas flow, after which the mixture was stirred at room temperature for 26 hours. The solvent of filtrate obtained by filtering the reacted liquid was evaporated off to obtain Compound 6 (319 mg, 80%) as a white solid (Step e).

The physical property data of the obtained Compound 6 was as follows: $^1$H-NMR (CD$_3$OD) δ: 1.87 (3H, d, J=1.0 Hz), 2.21 (3H, s), 3.45, 3.54 (2H, AB, J=14.5 Hz), 3.71, 3.86 (2H, AB, J=12.0 Hz), 4.23 (1H, d, J=6.5 Hz), 4.61 (1H, d, J=6.5 Hz), 5.85 (1H, s), 8.10 (1H, d, J=1.0 Hz).

Then, 4,4'-dimethoxytrityl chloride (630 mg, 1.86 mmol) was added to 7 mL of pyridine solution containing the obtained Compound 6 (219 mg, 0.62 mmol) in a nitrogen gas flow at 0° C., after which the mixture was stirred at room temperature for 20 hours. Next, after the reaction was quenched by adding saturated sodium bicarbonate solution to the reacted liquid at 0° C., the reacted liquid was extracted with dichloromethane, and the organic layer was washed with water and saturated saline and dried over anhydrous sodium sulfate. Next, the solvent was evaporated off to obtain a crude product. The obtained crude product was purified by silica gel chromatography (chloroform:methanol=40:1→5:1) to obtain Compound 7 (267 mg, 66%) as a white amorphous (Step f).

The physical property data of the obtained Compound 7 was as follows: $^1$H-NMR (CD$_3$OD) δ: 1.87 (3H, d, J=1.0 Hz), 2.21 (3H, s), 3.45, 3.54 (2H, AB, J=14.5 Hz), 3.71, 3.86 (2H, AB, J=12.0 Hz), 4.23 (1H, d, J=6.5 Hz), 4.61 (1H, d, J=6.5 Hz), 5.85 (1H, s), 8.10 (1H, d, J=1.0 Hz).

Diisopropylethylamine (146 μL, 0.84 mmol) was added to 2 mL of dichloromethane solution containing the obtained Compound 7 (131 mg, 0.21 mmol) in a nitrogen gas flow, and 2-cyanoethyl diisopropyl chlorophosphoramidite (96 μL, 0.43 mmol) was further added thereto at 0° C., after which the mixture was stirred at room temperature for 14 hours. Next, after the reaction was quenched by adding saturated sodium bicarbonate solution to the reacted liquid at 0° C., the reacted liquid was extracted with dichloromethane, and the organic layer was washed with water and dried over anhydrous sodium sulfate. Next, the solvent was evaporated off to obtain a crude product. The obtained crude product was purified through reprecipitation using dichloromethane and hexane to obtain Compound 8 (110 mg, 61%) as a white amorphous (Step g).

The physical property data of the obtained Compound 8 was as follows: $^{31}$P-NMR (CDCl$_3$) δ: 149.94, 151.37.

Example 2: Synthesis and Purification of Oligonucleotide Analog

Using Compound 8 obtained in Example 1, oligonucleotide analogs (Compounds 9 to 13: shown in Table 1 below) were synthesized by an automated DNA/RNA oligonucleotide synthesizer nS-8 (manufactured by Gene Design Inc.) with a 0.2 μmol-scale CPG support. The coupling time of acetonitrile solution (0.1M) containing Compound 8 was set to 16 minutes, and the other conditions were as those for synthesis of naturally occurring DNA. The activator used was 5-ethylthio-1H-tetrazole (0.5M). After the synthesized oligonucleotides were cut out of the CPG support using a 28% ammonia aqueous solution, the protecting groups of the base moieties were removed at 55° C. over 12 hours. The obtained crude product was purified using a reversed-phase short column (Sep-Pak@Plus C18 Environmental Cartridges, Waters) and was further purified by reversed-phase HPLC.

The synthesized oligonucleotide analogs (Compounds 9 to 13) were purified and their purities were determined by reversed-phase HPLC following the conditions below.

Mobile Phase
Solution (A): 0.1M triethylammonium acetate buffer, pH 7.0
Solution (B): 0.1M triethylammonium acetate buffer: acetonitrile=1:1, pH 7.0
Gradient:
Analytical 5-9% MeCN (30 min), Preparative 5-9% MeCN (30 min): Compound 9
Analytical 4-8% MeCN (30 min), Preparative 4-8% MeCN (30 min): Compound 10
Analytical 3-7% MeCN (30 min), Preparative 3-7% MeCN (30 min): Compound 11
Analytical 4-8% MeCN (30 min), Preparative 4-8% MeCN (30 min): Compound 12
Analytical 7-11% MeCN (30 min), Preparative 7-11% MeCN (30 min): Compound 13
Columns Used:
Analytical Waters XBridge™ OST C18 2.5 μm (4.6×50 mm) Preparative Waters XBridge™ OST C18 2.5 μm (10× 50 mm)
Flow Rate:
Analytical 1.0 mL/min
Preparative 4.5 mL/min
Column Temperature: 50° C.
Detection: UV (254 nm)

The molecular weights of the synthesized oligonucleotide analogs (Compounds 9 to 13) were determined by Time of Flight mass spectrometry (MALDI-TOF-MS). Table 1 shows the results.

TABLE 1

| Oligonucleotide[*1] | Yield (%) | Time of Flight Mass Spectrometry | |
|---|---|---|---|
| | | Cald. (M-H⁻) | Measured (M-H⁻) |
| SEQ ID No. 1: 5'-d(GCGTT<u>TTT</u>TGCT)-3' (Compound 9) | 15 | 3701.50 | 3700.64 |
| SEQ ID No. 2: 5'-d(GCGTT<u>TTT</u>TGCT)-3' (Compound 10) | 9 | 3770.56 | 3770.61 |
| SEQ ID No. 3: 5'-d(GCGT<u>TTT</u>TTGCT)-3' (Compound 11) | 7 | 3839.62 | 3838.94 |
| SEQ ID No. 4: 5'-d(GCGTT<u>T</u>TTTGCT)-3' (Compound 12) | 10 | 3770.56 | 3770.37 |
| SEQ ID No. 5: 5'-d(TTTTTTT<u>TT</u>)-3' (Compound 13) | 14 | 3048.02 | 3048.11 |

[*1]<u>T</u>: Guanidine-bridged Nucleic Acid

It was seen that the intended oligonucleotides were obtained because, as is clear from Table 1, the results of the molecular weight measurement by Time of Flight mass spectrometry (MALDI-TOF-MS) well matched the theoretical values.

For the purpose of comparison, an oligonucleotide containing a native nucleoside (Compound 14: Table 2 below, SEQ ID No. 7), and oligonucleotide analogs containing an urea-bridged artificial nucleic acid 2',4'-BNA/LNA (5-methyl-2'-O,4'-C-methyleneuridine (synthesized according to Non-Patent Document 6) (Compounds 15 to 18: Table 3 below, SEQ ID Nos. 8 to 11) were also synthesized and purified in a similar manner according to the standard phosphoramidite protocol.

Example 3: Measurement of Melting Temperature (Tm)

After each of the various oligonucleotides obtained in Example 2 (Compounds 9 to 12 (SEQ ID Nos. 1 to 4), oligonucleotide analogs produced using Compound 8; Compound 14 (SEQ ID No. 7), an oligonucleotide containing a native nucleoside; and Compounds 15 to 18 (SEQ ID Nos. 8 to 11), oligonucleotide analogs containing an urea-bridged artificial nucleic acid) was annealed to a target strand (SEQ ID No. 6: 5'-AGCAAAAAACGC-3') to form a duplex, its Tm value, a temperature at which 50% of duplexes are dissociated, was measured to determine the ability of the oligonucleotide for hydridization.

Specifically, a sample solution (130 μL) containing 100 mM NaCl, 10 mM sodium phosphate buffer (pH 7.2), 4 μM oligonucleotides, and 4 μM target strands was heated in a boiling water bath, and was then cooled down to room temperature over 10 hours. A nitrogen gas flow was passed through a cell chamber of a spectrophotometer (Shimadzu, UV-1650PC) in order to prevent dew condensation, and the sample solution was gradually cooled down to 5° C. and was kept at 5° C. for 5 minutes, after which the measurement was started. The temperature was gradually raised to 90° C. at a rate of 0.5° C./min, and ultraviolet absorption was measured at 260 nm at intervals of 0.1° C. Note that a cell with a lid was used in order to prevent the concentration from being changed by an increase in the temperature. Table 2 shows the results in Tm values and differences in the Tm values per modification unit. A higher Tm value indicates a higher duplex-forming ability.

TABLE 2

| Oligonucleotide[*1] | Tm (ΔTm/Unit modification) (° C.)[*2] | |
|---|---|---|
| | RNA | DNA |
| SEQ ID No. 7: 5'-d(GCGTTTTTTGCT)-3' (Compound 14) | 48 | 50 |
| SEQ ID No. 1: 5'-d(GCGTT<u>T</u>TTTGCT)-3' (Compound 9) | 47 (−1.0) | 49 (−1.0) |
| SEQ ID No. 2: 5'-d(GCGTT<u>T</u>TTTGCT)-3' (Compound 10) | 48 (+0.0) | 48 (−1.0) |
| SEQ ID No. 3: 5'-d(GCGT<u>T</u>TTTTGCT)-3' (Compound 11) | 49 (+0.3) | 46 (−1.3) |
| SEQ ID No. 4: 5'-d(GCGTT<u>T</u>TTTGCT)-3' (Compound 12) | 45 (−1.5) | 47 (−1.5) |

[*1]<u>T</u>: Guanidine-bridged Nucleic Acid
[*2]Target Strand Sequence: 5'-(AGCAAAAAACGC)-3'
[*2]Conditions: 10 mM Sodium phosphate buffer (pH 7.2), 100 mM NaCl, 4 μM Oligonucleotide, 0.5° C./min. (260 nm)

As is clear from Table 2, contrary to the prediction that the duplex-forming ability will be improved by the effects of the bridge structures and the cations, the duplex-forming ability was substantially the same as that of the native DNA. Also, it was seen that the Tm value increased as the ratio of artificial nucleic acids introduced into an oligonucleotide increased. Accordingly, it seems that the nucleotide analogs of the present invention are useful in synthesis of the oligonucleotides suitable for the antisense therapies.

In order to further study the effect of the cations at the bridge portions, Tm measurement was performed in a low salt concentration condition for developing the effect of the cations more (using a solution having the same compositions as those in the sample solution but free from NaCl). For the purpose of comparison, Tm measurement was performed also on the urea-bridged artificial nucleic acids (Compounds 15 to 18, SEQ ID Nos. 8-11). Table 3 shows the results.

TABLE 3

| Oligonucleotide[*1] | Tm (° C.)[*2] | |
|---|---|---|
| | RNA | DNA |
| SEQ ID No. 7: 5'-d(GCGTTTTTTGCT)-3' (Compound 14) | 33 | 38 |
| SEQ ID No. 1: 5'-d(GCGTTTTTGCT)-3' (Compound 9) | 34 | 39 |
| SEQ ID No. 2: 5'-d(GCGTTTTTGCT)-3' (Compound 10) | 34 | 39 |
| SEQ ID No. 3: 5'-d(GCGTTTTTGCT)-3' (Compound 11) | 38 | 39 |
| SEQ ID No. 4: 5'-d(GCGTTTTTGCT)-3' (Compound 12) | 32 | 33 |
| SEQ ID No. 8: 5'-d(GCGTTTTTGCT)-3' (Compound 15) | 34 | 37 |
| SEQ ID No. 9: 5'-d(GCGTTTTTGCT)-3' (Compound 16) | 37 | 30 |
| SEQ ID No. 10: 5'-d(GCGTTTTTGCT)-3' (Compound 17) | 40 | 28 |
| SEQ ID No. 11: 5'-d(GCGTTTTTGCT)-3' (Compound 18) | 36 | 29 |

[*1]T: Guanidine-bridged Nucleic Acid, T: Urea-bridged Nucleic Acid
[*2]Target Strand Sequence: 5'-(AGCAAAAAACGC)-3'
[*2]Conditions: 10 mM Sodium phosphate buffer (pH 7.2), no NaCl, 4 μM Oligonucleotide, 0.5° C./min. (260 nm)

As is clear from Table 3, there was not seen so much difference in the Tm values when RNA was targeted. On the other hand, when DNA was targeted, in the case of the urea-bridged artificial nucleic acids, the Tm value decreased as the ratio of artificial nucleic acids introduced to an oligonucleotide increased, whereas, in the case where guanidine-bridged artificial nucleic acids were introduced, such a drop in the Tm value was not seen. Accordingly, it was indicated that the cations at the bridge portions affect the stabilization of duplex with DNA.

Example 4: Synthesis of Nucleoside Analog (Compound 28)

[Chemical 14]

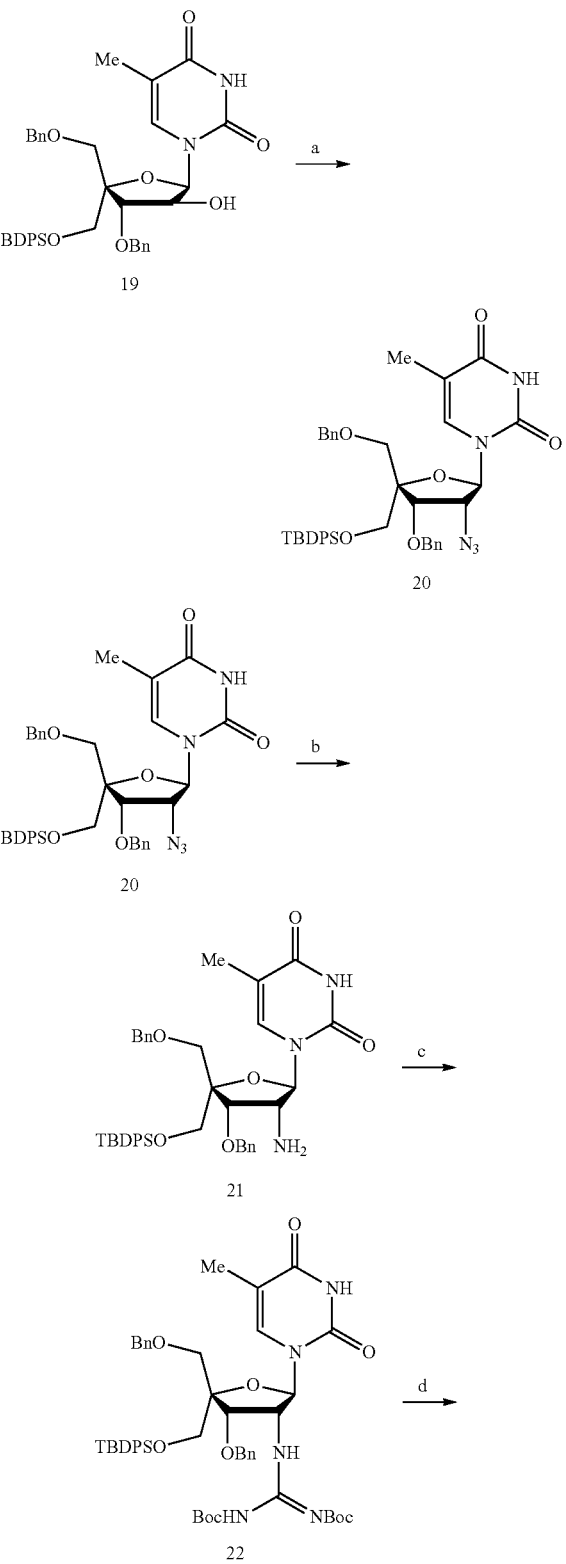

31
-continued
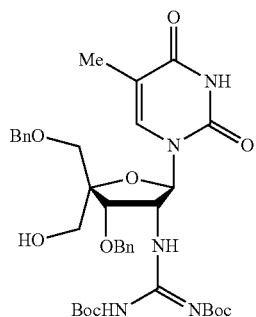
23
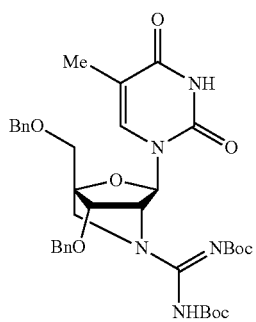
24
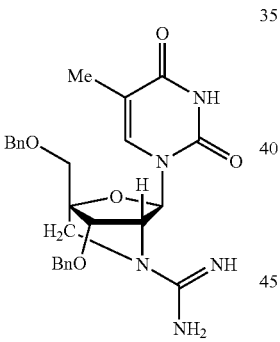
25
e →
e' →
f →
32
-continued
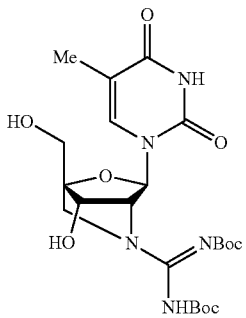
26
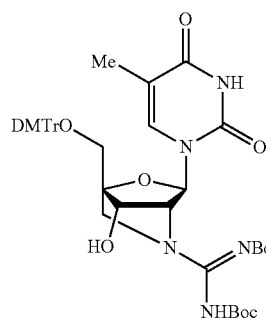
27
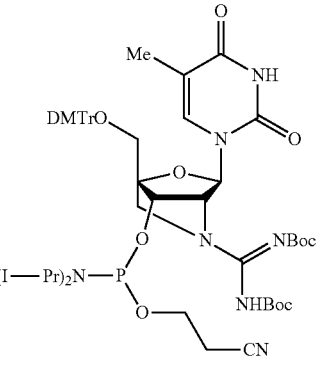
28
g →
h →
(1) Synthesis of Compound 20
[Chemical 15]
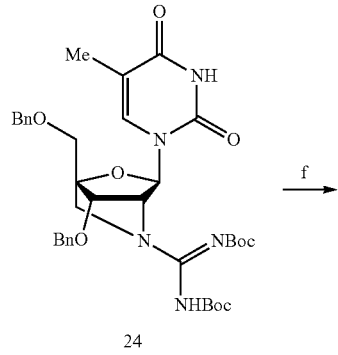
24
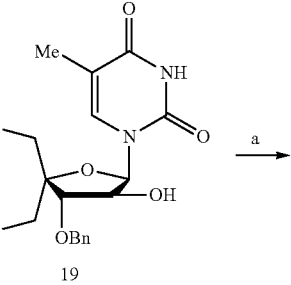
19
a →

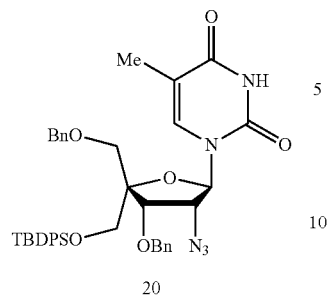
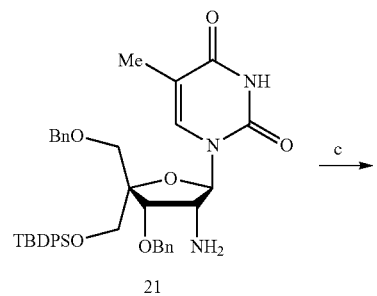

Compound 19 was obtained according to the preparation procedure of Compound 7 described in J. Org. Chem. (Shrestha, A. R. et al., 2011, vol. 76, p. 9891-9899). Pyridine (1.65 mL, 20.5 mmol) and trifluoromethanesulfonic anhydride (1.37 mL, 8.20 mmol) were added to a dichloromethane solution (40 mL) containing Compound 19 (2.86 g, 4.10 mmol) in a nitrogen gas flow on ice cooling, after which the mixture was stirred for 1 hour in ice-cooling condition. After the acid was decomposed by adding water, extraction with dichloromethane was performed, and the organic layer was dried over anhydrous sodium sulfate. After the solvent was evaporated off, a crude product was obtained as a yellow oil, and was simply purified by flash chromatography (n-hexane:ethyl acetate=3:1→2:1) to obtain a crude product as a light yellow amorphous. Subsequently, sodium azide (0.23 g, 3.60 mmol) was added to a dimethylformamide solution (80 mL) containing the crude product (1.96 g, 2.34 mmol) in a nitrogen gas flow, after which the mixture was stirred. After 48 hours, the solvent was evaporated off and water was added, and extraction with dichloromethane was performed, and the organic layer was washed with saturated saline and dried over anhydrous sodium sulfate. After the solvent was evaporated off, the obtained crude product was purified by flash column chromatography (n-hexane:ethyl acetate=3: 1) to obtain Compound 20 (1.71 g, 66%) as a white amorphous (Step a).

The physical property data of the obtained Compound 20 was as follows: $^1$H-NMR (300 MHz, CDCl$_3$) δ: 0.99 (9H, s), 1.58 (3H, s), 3.63, 3.69 (2H, AB, J=10.5 Hz), 3.69, 3.91 (2H, AB, J=10.5 Hz), 3.91 (1H, dd, J=7.2 Hz, 5.4 Hz), 4.23 (1H, d, J=5.4 Hz), 4.47, 4.53 (2H, AB, J=11.4 Hz), 4.57, 4.75 (2H, AB, J=11.4 Hz), 6.03 (1H, d, J=7.2 Hz), 7.23-7.60 (20H, m), 8.70 (1H, s).

(2) Synthesis of Compounds 24 and 25

[Chemical 16]

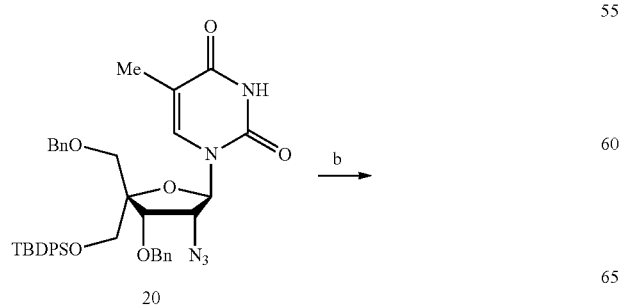

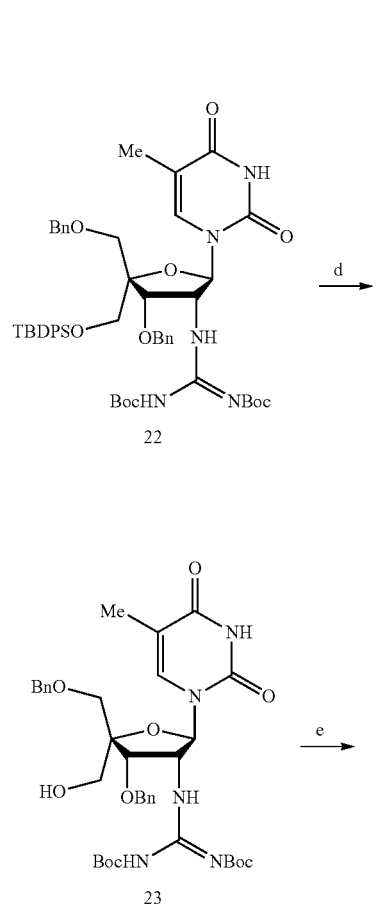

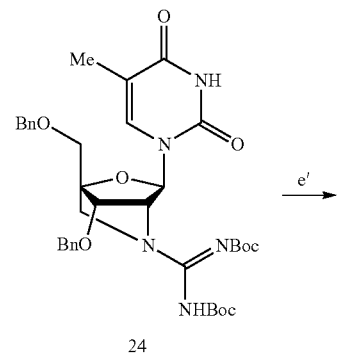

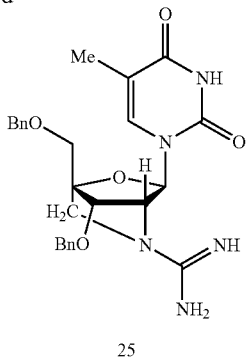

25

Nickel chloride (11 mg, 0.085 mmol) was added to 8 mL of methanol solution containing the obtained Compound 20 (622 mg, 0.85 mmol) in a nitrogen gas flow, and sodium borohydride (64 mg, 1.7 mmol) was further added thereto on ice cooling, after which the mixture was stirred at room temperature for 10 minutes. After the reacted liquid was filtered, the solvent was evaporated off and water was added, and extraction with ethyl acetate was performed. Next, the organic layer was washed with water and saturated saline and dried over sodium sulfate, and the solvent was evaporated off to obtain a crude product. The obtained crude product was purified by silica gel column chromatography (ethyl acetate:triethylamine=200:1) to obtain Compound 21 (456 mg, 76%) as a white solid (Step b).

The physical property data of the obtained Compound 21 was as follows: $^1$H-NMR (CDCl$_3$) δ: 1.04 (9H, s), 1.63 (3H, d, J=1.5 Hz), 3.59, 3.66 (2H, AB, J=10.0 Hz), 3.67 (1H, dd, J=5.5 Hz, 9.0 Hz), 3.79, 3.99 (2H, AB, J=11.0 Hz), 4.06 (1H, d, J=5.5 Hz), 4.55, 4.58 (2H, AB, J=11.0 Hz), 4.67, 4.76 (2H, AB, J=11.0 Hz), 5.81 (1H, d, J=9.0 Hz), 7.19-7.61 (21H, m), 7.95 (1H, s).

N,N'-di-(tert-butoxycarbonyl)thiourea (30.4 mg, 0.11 mmol), diisopropylethylamine (9 μL, 0.035 mmol), 1-ethyl-3-(3-dimethylaminopropyl)carbodiimide hydrochloride (21 mg, 0.11 mmol) were added to 1 mL of dichloromethane solution containing the obtained Compound 21 (50 mg, 0.071 mmol) in a nitrogen gas flow, after which the mixture was stirred at room temperature for 3 hours. Next, after the reaction was quenched by adding water at 0° C., the reacted liquid was extracted with dichloromethane, the organic layer was washed with water and saturated saline and dried over sodium sulfate, and the solvent was evaporated off to obtain a crude product. The obtained crude product was purified by silica gel column chromatography (hexane:ethyl acetate=4:1) to obtain Compound 22 (58 mg, 86%) as a white solid (Step c).

The physical property data of the obtained Compound 22 was as follows: $^1$H-NMR (CDCl$_3$) δ: 1.04 (9H, s), 1.42 (9H, s), 1.46 (9H, s), 1.72 (3H, d, J=1.0 Hz), 3.57, 3.96 (2H, AB, J=10.0 Hz), 3.73, 3.78 (2H, AB, J=11.0 Hz), 4.25 (1H, d, J=8.0 Hz), 4.57, 4.65 (2H, AB, J=11.0 Hz), 4.59, 4.61 (2H, AB, J=9.0 Hz), 4.89 (1H, q, J=8.0 Hz), 5.98 (1H, d, J=8.0 Hz), 7.20-7.69 (22H, m), 8.93 (1H, d, J=8.0 Hz), 11.34 (1H, s).

Tetra-n-butylammonium fluoride (0.14 mL, 0.14 mmol) was added to 1 mL of tetrahydrofuran solution containing the obtained Compound 22 (106 mg, 0.11 mmol) in a nitrogen gas flow, after which the mixture was stirred at room temperature for 4.5 hours. Next, the solvent was evaporated off, and the obtained crude product was purified by silica gel column chromatography (hexane:ethyl acetate=1:1) to obtain Compound 23 (80 mg, quantitative) as a white solid (Step d).

The physical property data of the obtained Compound 23 was as follows: $^1$H-NMR (CDCl$_3$) δ: 1.42 (9H, s), 1.50 (9H, s), 1.75 (3H, d, J=1.0 Hz), 2.05 (1H, dd, J=3.5 Hz, 9.0 Hz), 3.57, 3.62 (2H, AB, J=10.0 Hz), 3.68 (1H, dd, J=11.0 Hz, 9.0 Hz), 3.84 (1H, dd, J=11.0 Hz, 3.5 Hz), 4.35 (1H, d, J=7.5 Hz), 4.51, 4.72 (2H, AB, J=11.0 Hz), 4.58, 4.62 (2H, AB, J=11.5 Hz), 4.87 (1H, q, J=7.5 Hz), 6.07 (1H, d, J=7.5 Hz), 7.26-7.52 (11H, m), 7.88 (1H, s), 9.05 (1H, d, J=7.5 Hz), 11.39 (1H, s).

Pyridine (0.29 mL, 3.59 mmol) was added to 12 mL of dichloromethane solution containing the obtained Compound 23 (850 mg, 1.20 mmol) in a nitrogen gas flow, and trifluoromethanesulfonic anhydride (0.3 mL, 1.78 mmol) was further added thereto at 0° C., after which the mixture was stirred at 0° C. for 3 hours. Next, after the reaction was quenched by adding saturated sodium bicarbonate solution to the reacted liquid at 0° C., the reacted liquid was extracted with dichloromethane, and the organic layer was washed with water and saturated saline and dried over anhydrous sodium sulfate. Next, the solvent was evaporated off to obtain a crude product. Then, 2 mL of triethylamine was added to 8 mL of dichloromethane solution containing the crude product in a nitrogen gas flow, after which the mixture was stirred at room temperature for 27 hours. Next, the solvent was evaporated off and the obtained crude product was purified by silica gel column chromatography (hexane:ethyl acetate=1:1) to obtain Compound 24 (644 mg, 77%) as a yellowish white amorphous (Step e).

Next, 35% hydrochloric acid (0.3 mL) was added to 1 mL of tetrahydrofuran solution containing Compound 24 (57 mg, 0.082 mmol), after which the mixture was stirred at room temperature for 40 minutes. Next, after the reaction was quenched by adding saturated sodium bicarbonate solution to the reacted liquid at 0° C., the reacted liquid was extracted with dichloromethane, and the organic layer was washed with water and saturated saline and dried over anhydrous sodium sulfate. Next, the solvent was evaporated off to obtain Compound 25 (44 mg, quantitative) as a white solid (Step e').

The physical property data of the obtained Compound 25 was as follows: $^1$H-NMR (CD$_3$OD) δ: 1.54 (3H, d, J=1.0 Hz), 3.53, 3.70 (2H, AB, J=10.0 Hz), 3.90, 3.97 (2H, AB, J=11.0 Hz), 4.16 (1H, s), 4.60, 4.66 (2H, AB, J=11.5 Hz), 4.62 (2H, s), 4.78 (1H, s), 5.66 (1H, s), 7.27-7.38 (m, 10H), 7.50 (1H, d, J=1.0 Hz).

(2) Synthesis of Compound 28

[Chemical 17]

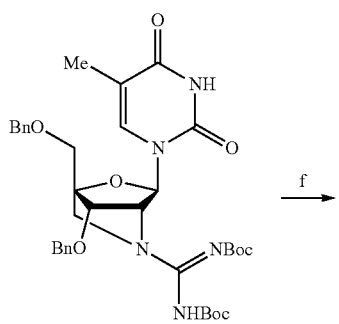

24 f →

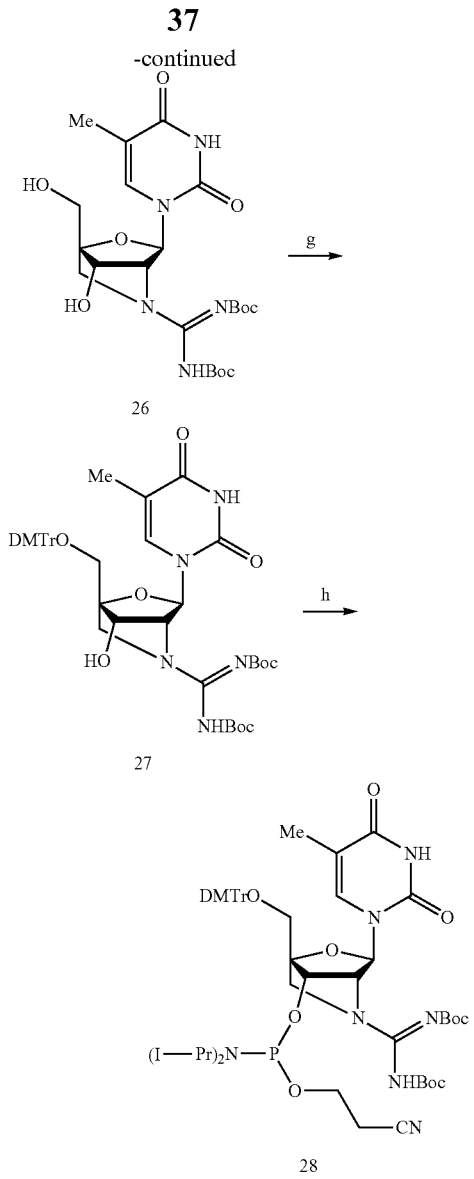

Palladium hydroxide on carbon (900 mg) was added to 10 mL of methanol solution containing the obtained Compound 24 (644 mg, 0.93 mmol) in a hydrogen gas flow, after which the mixture was stirred at room temperature for 14 hours. Next, the solvent of filtrate obtained by filtering the reacted liquid was evaporated off to obtain a crude product of Compound 26 (Step f).

Next, 4,4'-dimethoxytrityl chloride (469 mg, 1.38 mmol) was added to 7 mL of pyridine solution containing the crude product (354 mg) of Compound 26 in a nitrogen gas flow at 0° C., after which the mixture was stirred at room temperature for 12 hours. Next, after the reaction was quenched by adding saturated sodium bicarbonate solution to the reacted liquid at 0° C., the reacted liquid was extracted with dichloromethane, and the organic layer was washed with water and saturated saline and dried over anhydrous sodium sulfate. Next, the solvent was evaporated off to obtain a crude product. The obtained crude product was purified by silica gel column chromatography (hexane:ethyl acetate=1:1) to obtain Compound 27 (442 mg, 58%) as a white solid (Step g).

The physical property data of the obtained Compound 27 was as follows: $^1$H-NMR (CD$_3$OD) δ: 1.42 (18H, s), 1.49 (3H, s), 3.39-3.55 (4H, m), 3.73 (6H, s), 4.39 (1H, s), 4.57 (1H, s), 5.51 (1H, s), 6.83 (4H, d, J=9.0 Hz), 7.17-7.44 (m, 9H), 7.77 (1H, s).

N,N-diisopropyl ammonium tetrazolide (39 mg, 0.23 mmol) and 2-cyanoethyl N,N,N',N'-tetraisopropyl phosphoramidite (73 μL, 0.23 mmol) were added to 2 mL of acetonitrile solution containing the obtained Compound 27 (141 mg, 0.17 mmol) in a nitrogen gas flow, after which the mixture was stirred at room temperature for 3 hours. Next, after the reaction was quenched by adding water to the reacted liquid at 0° C., extraction with ethyl acetate was performed, and the organic layer was washed with water and saturated saline and dried over Na$_2$SO$_4$. The solvent was evaporated off, and the obtained crude product was purified by silica gel column chromatography (hexane:ethyl acetate=3:2) to obtain Compound 28 (148 mg, 86%) as a white amorphous (Step h).

The physical property data of the obtained Compound 28 was as follows: $^{31}$P-NMR (CDCl$_3$) δ: 148.78, 149.48, 149.78.

Example 5: Synthesis and Purification of Oligonucleotide Analogs

Using Compound 28 obtained in Example 4, 10 mers of oligonucleotide analogs (Compounds 29 to 32: shown in Table 4 below, SEQ ID Nos. 12 to 15) were synthesized by an automated DNA/RNA oligonucleotide synthesizer nS-8 (manufactured by Gene Design Inc.) with a 0.2 μmol-scale CPG support. The coupling time of acetonitrile solution (0.1M) containing Compound 28 was set to 8 minutes, and the other conditions were as those for synthesis of native DNA. The activator used was 5-[3,5-bis(trifluoromethyl)phenyl]-1H-tetrazole (0.25M). The synthesized oligonucleotides were cut out of the CPG support using a 28% ammonia aqueous solution. The crude products of the obtained Compounds 29 to 31 were purified using a reversed-phase short column (Sep-Pak@Plus C18 Environmental Cartridges, Waters) and then treated with trifluoroacetic acid (TFA) 50% for 24 hours, and were further purified by reversed-phase HPLC. The crude product of the obtained Compound 32 (SEQ ID No. 15) was purified using a reversed-phase short column (Sep-Pak@Plus C18 Environmental Cartridges, Waters) and was further purified by reversed-phase HPLC.

The synthesized oligonucleotide analogs (Compounds 29 to 32, SEQ ID Nos. 12 to 15) were purified and their purities were determined as in Example 2.

The molecular weights of the synthesized oligonucleotide analogs (Compounds 29 to 32, SEQ ID Nos. 12 to 15) were determined by MALDI-TOF-MASS measurement. Table 4 shows the results.

TABLE 4

| Oligonucleotide*1 | Yield (%) | Time of Flight Mass Spectrometry | |
|---|---|---|---|
| | | Cald. (M-H$^-$) | Measured (M-H$^-$) |
| SEQ ID No. 12: 5'-d(TTTTtTTTTT)-3' (Compound 29) | 9 | 3048.02 | 3048.84 |
| SEQ ID No. 13: 5'-d(TTTTtTtTTT)-3' (Compound 30) | 7 | 3117.09 | 3117.57 |

TABLE 4-continued

| Oligonucleotide*1 | Yield (%) | Time of Flight Mass Spectrometry | |
|---|---|---|---|
| | | Cald. (M-H⁻) | Measured (M-H⁻) |
| SEQ ID No. 14:<br>5'-d(TTtTtTtTTT)-3'<br>(Compound 31) | 3 | 3186.16 | 3186.50 |
| SEQ ID No. 15:<br>5'-d(TTTTTTTTtT)-3'<br>(Compound 32) | 2 | 3048.02 | 3047.85 |

*¹t: Guanidine-bridged Nucleic Acid

For the purpose of comparison, an oligonucleotide containing a native nucleoside (Compound 33: shown in Table 5 below, SEQ ID No. 16) was also synthesized and purified in a similar manner according to the standard phosphoramidite protocol.

Example 6: Measurement of Melting Temperature (Tm)

After each of the various oligonucleotides (Compounds 29 to 31 (SEQ ID Nos. 12 to 14), oligonucleotide analogs produced using Compound 28; and Compound 33 (SEQ ID No. 16), an oligonucleotide containing a native nucleoside) obtained in Example 5 was annealed to any of target strands (10 mers of poly A and SEQ ID Nos. 17 to 20) shown in Tables 5 and 6 below to form a complex, its Tm value, a temperature at which 50% of the complexes are dissociated, was measured to determine the ability of the oligonucleotide for hybridization.

Specifically, a sample solution (130 μL) containing 100 mM NaCl, 10 mM sodium phosphate buffer (pH 7.2), 4 μM oligonucleotides, and 4 μM target strands was heated in a boiling water bath, and was then cooled down to room temperature over 10 hours. A nitrogen gas flow was passed through a cell chamber of a spectrophotometer (Shimadzu, UV-1650PC) in order to prevent dew condensation, and the sample solution was gradually cooled down to 0° C. and was kept at 0° C. for 5 minutes, after which the measurement was started. The temperature was gradually raised to 80° C. at a rate of 0.5° C./min, and ultraviolet absorption was measured at 260 nm at intervals of 0.1° C. Note that a cell with a lid was used in order to prevent the concentration from being changed by an increase in the temperature. Table 5 shows, in terms of Tm values and differences in the Tm values per modification unit, the abilities of the various oligonucleotide analogs containing a different number of guanidine-bridged artificial nucleic acids to hybridize to poly A. Table 6 shows, in terms of Tm values, the abilities of the oligonucleotide analog containing the guanidine-bridged artificial nucleic acid and the oligonucleotide containing the native nucleoside to hybridize to various target strands.

TABLE 5

| Oligonucleotide*1 | Tm (ΔTm/Unit modification) (° C.)*2 | |
|---|---|---|
| | RNA | DNA |
| SEQ ID No. 16:<br>5'-d(TTTTTTTTTT)-3'<br>(Compound 33) | 19 | 20 |

TABLE 5-continued

| Oligonucleotide*1 | Tm (ΔTm/Unit modification) (° C.)*2 | |
|---|---|---|
| | RNA | DNA |
| SEQ ID No. 12:<br>5'-d(TTTTtTTTTT)-3'<br>(Compound 29) | 24<br>(+5.0) | 24<br>(+4.0) |
| SEQ ID No. 13:<br>5'-d(TTTTtTtTTT)-3'<br>(Compound 30) | 30<br>(+5.5) | 36<br>(+8.0) |
| SEQ ID No. 14:<br>5'-d(TTtTtTtTTT)-3'<br>(Compound 31) | 40<br>(+7.0) | 50<br>(+10.0) |

*¹t: Guanidine-bridged Nucleic Acid
*²Target Strand Sequence: 5'-(AAAAAAAAAA)-3'
*²Conditions: 10 mM Sodium phosphate buffer (pH 7.2), 100 mM NaCl, 4 μM Oligonucleotide, 0.5° C./min. (260 nm)

TABLE 6

| Oligonucleotide*1 | Target Strand | Tm (° C.)*2 | |
|---|---|---|---|
| | | RNA | DNA |
| SEQ ID No. 12:<br>5'-d(TTTTtTTTTT)-3'<br>(Compound 29) | 5'-(AAAAAAAAAA)-3' | 24 | 24 |
| SEQ ID No. 12:<br>5'-d(TTTTtTTTTT)-3'<br>(Compound 29) | 5'-(AAAAAGAAAA)-3' | 17 | 10 |
| SEQ ID No. 12:<br>5'-d(TTTTtTTTTT)-3'<br>(Compound 29) | 5'-(AAAAACAAAA)-3' | 10 | 10 |
| SEQ ID No. 12:<br>5'-d(TTTTtTTTTT)-3'<br>(Compound 29) | 5'-(AAAAATAAAA)-3' | 12 | 10 |
| SEQ ID No. 16:<br>5'-d(TTTTTTTTTT)-3'<br>(Compound 33) | 5'-(AAAAAAAAAA)-3' | 19 | 20 |
| SEQ ID No. 16:<br>5'-d(TTTTTTTTTT)-3'<br>(Compound 33) | 5'-(AAAAAGAAAA)-3' | 13 | <10 |
| SEQ ID No. 16:<br>5'-d(TTTTTTTTTT)-3'<br>(Compound 33) | 5'-(AAAAACAAAA)-3' | <10 | <10 |
| SEQ ID No. 16:<br>5'-d(TTTTTTTTTT)-3'<br>(Compound 33) | 5'-(AAAAATAAAA)-3' | <10 | <10 |

*¹t: Guanidine-bridged Nucleic Acid
*²Conditions: 10 mM Sodium phosphate buffer (pH 7.2), 100 mM NaCl, 4 μM Oligonucleotide, 0.5° C./min. (260 nm)

As is clear from Table 5, the oligonucleotides containing the guanidine-bridged artificial nucleic acids had excellent complex-forming abilities not only with respect to RNA but also with respect to DNA. Also, it was seen that the Tm value increased as the ratio of artificial nucleic acids introduced into an oligonucleotide increased. Accordingly, it seems that the guanidine-bridged artificial nucleic acids of the present invention are useful in synthesis of the oligonucleotides suitable for the antisense therapies.

As is clear from Table 6, the oligonucleotide containing the guanidine-bridged artificial nucleic acid had mismatch recognition ability. The oligonucleotides containing the guanidine-bridged artificial nucleic acids had more excellent complex-forming abilities with respect to desirable target strands (i.e., poly A) than the oligonucleotide containing the native nucleoside. Accordingly, it was seen that the oligonucleotides containing the guanidine-bridged artificial nucleic acids have no risk of forming complexes in a sequence-non-specific manner.

Example 7: Evaluation of Double Strand-Forming Ability of Oligonucleotide Analogs Using Compound 28 obtained in Example 4, 9 mers of oligonucleotide analog containing various bases (Compound 34: shown in Table 7 below, SEQ ID No. 23) was synthesized and purified as in Example 5, except that, after the synthesized oligonucleotide was cut out of the CPG support using a 28% ammonia aqueous solution, the protecting group of the base moiety was removed at 55° C. over 12 hours. For the purpose of comparison, an oligonucleotide containing a native nucleoside (Compound 35: shown in Table 7 below, SEQ ID No. 22) was also synthesized and purified in a similar manner according to the standard phosphoramidite protocol.

After each of the oligonucleotides of Compounds 34 and 35 (SEQ ID Nos. 23 and 22) was annealed to a target strand SEQ ID No. 21: 5'-GTGATATGC-3' to form a duplex, its Tm value, a temperature at which 50% of duplexes are dissociated, was measured to determine ability of the oligonucleotide for hybridization. The annealing to the target strand and the measurement of the Tm values were performed as in Example 6. Table 7 shows the results of the Tm values.

TABLE 7

| Oligonucleotide[*1] | Tm (° C.)[*2] | |
|---|---|---|
| | RNA | DNA |
| SEQ ID No. 22:<br>5'-d(GCATATCAC)-3' (Compound 35) | 32 | 35 |
| SEQ ID No. 23:<br>5'-d(GCAtATCAC)-3' (Compound 34) | 40 | 44 |

[*1]t: Guanidine-bridged Nucleic Acid
[*2]Target Strand Sequence: 5'-(GTGATATGC)-3'
[*2]Conditions: 10 mM Sodium phosphate buffer (pH 7.2), 100 mM NaCl, 4 μM Oligonucleotide, 0.5° C./min. (260 nm)

As is clear from Table 7, also in the case of designing the sequence so as to contain various bases, the oligonucleotide containing the guanidine-bridged artificial nucleic acid (Compound 34, SEQ ID No. 23) had excellent duplex-forming abilities with respect to both RNA and DNA as in the case of the poly T sequence.

Example 8: Evaluation of Triplex-Forming Ability of Oligonucleotide Analog

[Chemical 18]

SEQ ID No. 24: 5'-TTTTTCTXTCTCTCT-3'
SEQ ID No. 25: 5'-GGCAAAAAGAYAGAGAGACGC─┐
SEQ ID No. 26:    3'-CCGTTTTTCTZTCTCTCTGCG─┘ [C18-Spacer]

Using Compound 28 obtained in Example 4, 15 mers of oligonucleotide analog (Compound 36, SEQ ID No. 24: where "X" is a guanidine-bridged artificial nucleic acid, and the underlined C is 2'-deoxy 5-methylcytidine, see Table 8 below) was synthesized and purified as in Example 5, except that, after the synthesized oligonucleotide was cut out of the CPG support using a 28% ammonia aqueous solution, the protecting group of the base moiety was removed at 55° C. over 12 hours. For the purpose of comparison, an oligonucleotide containing a native nucleoside (Compound 37, SEQ ID No. 27: where "X" is a native nucleoside, and the underlined C is 2'-deoxy 5-methylcytidine, see Table 8 below) was also synthesized and purified in a similar manner according to the standard phosphoramidite protocol.

A target DNA duplex containing a target strand SEQ ID No. 25: 5'-GGCAAAAAGAYAGAGAGACGC-3' and its complementary strand SEQ ID No. 26 5'-GCGTCTCTCTZ-TCTTTTTGCC-3' was prepared as follows. 5'-GGCAAAAAGAYAGAGAGACGC-[C18-spacer]-GCGTCTCTCTZTCTTTTTGCC-3' (strand obtained by linking the 3' end of the oligonucleotide strand of SEQ ID No. 25 and the 5' end of the oligonucleotide strand of SEQ ID No. 26 via a [C18-spacer] as a linker) was synthesized and purified according to the standard phosphoramidite protocol, except that 18-O-dimethoxytritylhexaethyleneglycol and 1-[(2-cyanoethyl)-(N/N-diisopropyl)]-phosphoramidite (manufactured by Glen Research) were used for the synthesis of the linker portions, so that a intended target DNA duplex was obtained. In the formula, Y and Z refer to a combination that may form a base pair, and are as follows: Y is A, and Z is T; Y is T, and Z is A; Y is G, and Z is C; or Y is C, and Z is G.

After each of the oligonucleotides of Compounds 36 and 37 (SEQ ID Nos. 24 and 27) was annealed to a target duplex to form a triplex, its Tm value, a temperature at which 50% of triplexes are dissociated, was measured to determine the ability of the oligonucleotide for hybridization.

Specifically, a sample solution (130 μL) containing 10 mM sodium cacodylate buffer (pH 6.8), 100 mM KCl, 50 mM MgCl$_2$, 1.89 μM oligonucleotides, and 1.89 μM target duplex was heated in a boiling water bath, and was then cooled down to room temperature over 10 hours. A nitrogen gas flow was passed through a cell chamber of a spectrophotometer (Shimadzu, UV-1650PC) in order to prevent dew condensation, and the sample solution was gradually cooled down to 5° C. and was kept at 5° C. for 20 minutes, after which the measurement was started. The temperature was gradually raised to 90° C. at a rate of 0.5° C./min, and ultraviolet absorption was measured at 260 nm at intervals of 0.1° C. Note that a cell with a lid was used in order to prevent the concentration from being changed by an increase in the temperature. Table 8 shows the results of the Tm values. A higher Tm value indicates a higher triplex-forming ability.

TABLE 8

| Oligonucleotide[*1] | Tm(° C.)[*2] Target YZ Combination | | | |
|---|---|---|---|---|
| | AT | TA | GC | CG |
| SEQ ID No. 27:<br>5'-d(TTTTTCTTTCTCTCT)-3' (Compound 37) | 44 | 20 | 23 | 29 |
| SEQ ID No. 28:<br>5'-d(TTTTTCTtTCTCTCT)-3' (Compound 36) | 54 | 17 | 38 | 20 |

[*1]t: Guanidine-bridged Nucleic Acid
[*1]C: 2'-deoxy-5-methylcytisine
[*2]Conditions: 10 mM Sodium cacodylate buffer (pH 6.8), 100 mM KCl, and 50 mM MgCl$_2$, 1.89 μM Oligonucleotide, 0.5° C./min. (260 nm)

As is clear from Table 8, the oligonucleotide containing the guanidine-bridged artificial nucleic acid (modified Compound 36, SEQ ID No. 28) had excellent triplex-forming abilities with respect to a desirable target duplex (Y is A, and Z is T).

Example 9: Evaluation of Nuclease Resistance of Oligonucleotide Analogs

In this example, 10 mers of various oligonucleotides were prepared where X of the sequence, SEQ ID No. 29: 5'-d (TTTTTTTTXT)-3', was as follows. That is to say, the following various oligonucleotides were prepared: an oligonucleotide analog produced using the nucleoside analog (Compound 8) of Example 1, where X was a guanidine-bridged artificial nucleic acid (i.e., "Compound 13", SEQ ID No. 5); an oligonucleotide analog produced using the nucleoside analog (Compound 28) of Example 4, where X was a guanidine-bridged artificial nucleic acid (i.e., "Compound 32", SEQ ID No. 15); an oligonucleotide where X was an LNA-T (thymine LNA) (Compound 38, manufactured by Gene Design Inc.); an oligonucleotide where X was a DNA-T (thymine DNA) (10 mers of oligo dT, i.e., "Compound 33"); and an oligonucleotide synthesized and purified according to the standard phosphoramidite protocol, where X was an S-oligo (synthesized and purified according to the standard phosphorothioate synthesis protocol, except that D-1,4-dithiothreitol (DDTT, manufactured by ChemGene) was used instead of an oxidizing agent as a sulfurizing agent (Compound 39: used as a positive control).

The nuclease resistance was evaluated as follows. That is to say, 0.175 μg of 3'-exonuclease (*Crotalus admanteus* venom phosphodiesterase: CAVP, manufactured by Pharmacia Biotech) was added to and mixed with 100 μL of buffer (50 mM Tris-HCl (pH 8.0), 10 mM $MgCl_2$) containing each of various oligonucleotides (750 pmol), after which the mixture was incubated at 37° C., and part of the reacted liquid was taken out at equal intervals after the start of the reaction. The taken out reacted liquid was heated at 90° C. for 2 minutes to deactivate the enzyme, and the remaining amount of oligonucleotides was determined by HPLC. The HPLC conditions were as follows: gradient 6-12% MeCN (15 min); flow rate 0.8 mL/min; and column temperature 50° C. The remaining amount of oligonucleotides was calculated as the percentage of unreacted oligonucleotides (%), and plotted against the reaction time. FIG. 1 shows the results.

FIG. 1 is a graph showing a change over time in the percentage of unreacted oligonucleotides when various oligonucleotides having the sequence, SEQ ID No. 29 5'-d (TTTTTTTTXT)-3', were treated with 3'-exonuclease. In FIG. 1, the vertical axis indicates the percentage of unreacted oligonucleotides (%) to the nuclease treatment, and the horizontal axis indicates the nuclease treatment time (min). The symbols in FIG. 1 are as follows: quadrangle represents an oligonucleotide containing a naturally occurring nucleoside (Compound 33, SEQ ID No. 16); circle represents an oligonucleotide containing an LNA (Compound 38); triangle represents an oligonucleotide containing a guanidine-bridged artificial nucleic acid (Compound 32, SEQ ID No. 15); x represents an oligonucleotide containing a guanidine-bridged artificial nucleic acid (Compound 13, SEQ ID No. 5); and inverted triangle represents an oligonucleotide containing an S-oligo (Compound 39).

As is clear from FIG. 1, 50% or more of Compound 13 (SEQ ID No. 5) was left unreacted even after the nuclease treatment for 20 minutes, that is, it was resistant to be degraded. Compound 32 (SEQ ID No. 15) had a lower percentage of oligonucleotides remaining unreacted than that of Compound 13 (SEQ ID No. 5). However, Compound 32 (SEQ ID No. 15) was resistant to be degraded compared with Compound 38 (oligonucleotide containing LNA) that was almost completely degraded after the nuclease treatment for 10 minutes.

Example 10: Evaluation of Nuclease Resistance of Oligonucleotide Analog

In this example, 9 mers of oligonucleotide (Compound 40) where X of the sequence, 5'-d(TTTTTTTTX)-3', was a guanidine-bridged artificial nucleic acid was prepared as follows.

That is to say, 3'-exonuclease (*Crotalus admanteus* venom phosphodiesterase: CAVP, manufactured by Pharmacia Biotech) (0.2 μg) was added to and mixed with 40 μL of buffer (50 mM Tris-HCl (pH 8.0), 10 mM $MgCl_2$) containing Compound 32 (3330 pmol), after which the mixture was incubated at 37° C. for 3 hours. Next, heating was performed at 90° C. for 2 minutes to deactivate the enzyme, and purification by HPLC was performed. It was seen that the intended oligonucleotide was obtained because the molecular weight measurement value (2743.07) of the obtained oligonucleotide by Time of Flight mass spectrometry (MALDI-TOF-MS) well matched the theoretical value (2743.83).

For the purpose of comparison, an oligonucleotide where X of the sequence, 5'-d(TTTTTTTTX)-3', was an LNA (manufactured by Gene Design Inc.: Compound 41) was used.

The nuclease resistance was evaluated as in Example 9, except that 0.08 μg of 3'-exonuclease was added to 100 μL of buffer containing each of various oligonucleotides (750 pmol). FIG. 2 shows the results.

FIG. 2 is a graph showing a change over time in the percentage of unreacted oligonucleotides when various oligonucleotides having the sequence, 5'-d(TTTTTTTTX)-3', were treated with 3'-exonuclease. In FIG. 2, the vertical axis indicates the percentage of unreacted oligonucleotides (%) to the nuclease treatment, and the horizontal axis indicates the nuclease treatment time (min). The symbols in FIG. 2 are as follows: circle represents an oligonucleotide containing an LNA (Compound 41); and triangle represents an oligonucleotide containing a guanidine-bridged artificial nucleic acid (Compound 40).

As is clear from FIG. 2, 80% of Compound 40 (oligonucleotide containing guanidine-bridged artificial nucleic acid) was left unreacted even after the nuclease treatment for 20 minutes. On the other hand, there was almost no unreacted oligonucleotide of Compound 41 (oligonucleotide containing LNA) after the nuclease treatment for 20 minutes. In this manner, an oligonucleotide containing a 5-membered ring guanidine-bridged artificial nucleic acid at the 3' end, as in the guanidine-bridged nucleoside analog (Compound 28) in Example 4, exhibited an extremely high nuclease resistance.

Example 11; Measurement of Melting Temperature (Tm) of Oligonucleotide Analogs After each of Compound 33 (native oligonucleotide containing 10 mers of oligo dT); Compound 29 to 31, 42 and 43 (oligonucleotide analogs containing guanidine-bridged nucleic acids of Compound 28); and Compounds 44 to 48 (oligonucleotides containing LNA-T) shown in Table 9 below was annealed to 10 mers of poly A to form a complex, its Tm value, a temperature at which 50% of complexes are dissociated, was measured to determine the ability of the oligonucleotide for hybridization.

Compounds 29 to 31, 42 and 43 were synthesized and purified as in Example 5, except that TFA 75% was used instead of TFA 50% in the TFA treatment after the purification using a reversed-phase short column. Compounds 44 to 48 were manufactured by Gene Design Inc.

The formation of the complexes and the measurement of the Tm values were performed as in Example 6, except that a sample solution (130 µL) containing 200 mM KCl, 20 mM potassium cacodylate buffer (pH 6.8), 4 µM oligonucleotides, and 4 µM target strands was used. Table 9 shows the results. Table 9 shows the comparison results between the native oligonucleotide and the various oligonucleotides containing a different number of LNAs, in terms of Tm values and differences in the Tm values per modification unit, the abilities of the various oligonucleotide analogs containing a different number of guanidine-bridged artificial nucleic acids for hybridization to poly A.

TABLE 9

| Oligonucleotide*1 | Tm (ΔTm/Unit modification) (° C.)*2 | |
|---|---|---|
| | RNA | DNA |
| SEQ ID No. 16: 5'-d(TTTTTTTTT)-3' (Compound 33) | 22 | 25 |
| SEQ ID No. 12: 5'-d(TTTTtTTTTT)-3' (Compound 29) | 27 (+5.0) | 30 (+5.0) |
| SEQ ID No. 13: 5'-d(TTTTtTtTTT)-3' (Compound 30) | 33 (+5.5) | 42 (+8.5) |
| SEQ ID No. 14: 5'-d(TTtTtTtTTT)-3' (Compound 31) | 44 (+7.3) | 57 (+10.7) |
| SEQ ID No. 31: 5'-d(TTTtttTTTT)-3' (Compound 42) | 44 (+7.3) | 55 (+10.0) |
| SEQ ID No. 32: 5'-d(tTtTtTtTtT)-3' (Compound 43) | 66 (+8.8) | 79 (+10.8) |
| SEQ ID No. 33: 5'-d(TTTTTTTTT)-3' (Compound 44) | 28 (+6.0) | 25 (+0.0) |
| SEQ ID No. 34: 5'-d(TTTTTTTTT)-3' (Compound 45) | 34 (+6.0) | 31 (+3.0) |
| SEQ ID No. 35: 5'-d(TTTTTTTTT)-3' (Compound 46) | 43 (+7.0) | 40 (+5.0) |
| SEQ ID No. 36: 5'-d(TTTTTTTTT)-3' (Compound 47) | 42 (+6.7) | 35 (+3.3) |
| SEQ ID No. 37: 5'-d(TTTTTTTTT)-3' (Compound 48) | 50 (+5.6) | 48 (+4.6) |

*1 t: Guanidine-bridged Nucleic Acid T:LNA
*2 Target Strand Sequence: 5'-(AAAAAAAAAA)-3'
*2 Conditions: 20 mM Sodium cacodylate buffer (pH 6.8), 200 mM KCl, 4 µM Oligonucleotide, 0.5° C./min. (260 nm)

As is clear from Table 9, when RNA was targeted, the oligonucleotide analogs containing the guanidine-bridged artificial nucleic acids had sufficiently high binding affinities compared with the native oligonucleotide. Furthermore, when the number of artificial nucleic acids introduced was 3 residues or less, the oligonucleotide analogs containing the guanidine-bridged artificial nucleic acids had the Tm values similar to those of the oligonucleotides containing the LNAs, but the oligonucleotide into which 5 residues of guanidine-bridged artificial nucleic acid were introduced exhibited higher binding affinities than that into which 5 residues of LNA were introduced. The comparison of increases in the Tm values per residue clearly showed that, when the LNA was introduced, an increase in the Tm values was 6 to 7° C. regardless of the number introduced, whereas, when the guanidine-bridged artificial nucleic acid was introduced, an increase in the Tm values per residue became larger as the number introduced was increased. Accordingly, it was indicated that the bridge structures additively affect the binding affinity, whereas the guanidine-derived cations synergistically affect the binding affinity. Also, it was seen that, when DNA was targeted, the oligonucleotides containing the guanidine-bridged artificial nucleic acids exhibited an extremely high binding affinity, and had an extremely higher binding affinity than those of the native oligonucleotide and the oligonucleotides containing the LNAs.

Example 12: Evaluation of Target Base Recognition Ability of Oligonucleotide Analogs The oligonucleotide analog into which 5 residues of guanidine-bridged artificial nucleic acid were introduced (Compound 43, SEQ ID No. 42) and the oligonucleotide into which 5 residues of LNA were introduced (Compound 48, SEQ ID No. 37), shown in Table 9, were evaluated for the binding affinities with respect to a DNA target strand having a fully complementary sequence (full-match) and a DNA target strand having a single-base mismatch (mismatch). The sequences of the target strands were as follows: full-match SEQ ID No. 17: 5'-(AAA)-3'; and mismatch SEQ ID No. 20: 5'-(AAAAATAAAA)-3'. The binding affinities were evaluated as in Example 11 by performing annealing treatment to form a complex, and then measuring its Tm value, a temperature at which 50% of complexes are dissociated.

FIG. 3 shows the results. FIG. 3 shows Tm curves of an oligonucleotide analog containing a guanidine-bridged artificial nucleic acid and an oligonucleotide containing an LNA, with respect to a DNA target strand having a fully complementary sequence (full-match) and a DNA target strand having a single-base mismatch (mismatch). In FIG. 3, the vertical axis indicates the absorbance at 260 nm, and the horizontal axis indicates the temperature (° C.). The graph shows the results of the oligonucleotide analog containing the guanidine-bridged artificial nucleic acid (Compound 43, SEQ ID No. 32) with respect to mismatch (thin single line) and full-match (thin single broken line), and of the oligonucleotide containing the LNA (Compound 48, SEQ ID No. 37) with respect to mismatch (thick single line) and full-match (thick single broken line).

As is clear from FIG. 3, the oligonucleotide analog containing the guanidine-bridged artificial nucleic acid (Compound 43, SEQ ID No. 32) had a sufficiently low Tm value with respect to the mismatch target strand compared with the Tm value with respect to the full-match target strand, and the decrease in the Tm value was similar to that of the oligonucleotide containing the LNA (Compound 48, SEQ ID No. 37). Accordingly, it was seen that the oligonucleotide containing the guanidine-bridged artificial nucleic acid had an extremely high binding affinity with a target strand, without impairing the target base recognition ability.

Example 13: Evaluation of Guanidine-Bridged Artificial Nucleic Acid (Hereinafter, it May be Referred to as GuNA) Regarding Kinetics in Cells (1) Synthesis and Identification of Fluorescent Labeled GuNA Modified Oligonucleotides (F-GuNA-ODN)

First, using Compound 28 obtained in Example 4, a native nucleoside, and an amidite for fluorescent modification described later, an oligonucleotide analog was synthesized by an automated DNA/RNA oligonucleotide synthesizer nS-8 (manufactured by Gene Design Inc.). The synthesized oligonucleotide analog is a compound for use as a precursor (Compound 49) of Compounds 53 to 57 shown in Table 10. The structure of this precursor (Compound 49) is shown below.

[Chemical 19]

[Compound 49]

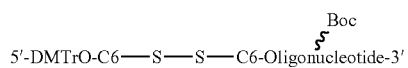

In the automated synthesis of the oligonucleotide, all of thymidine amidite (model number: T111081), thymidine CPG solid-phase support (model number: T361010), CapA (model number: L840020-06), CapB (model number: L850020-06), and an oxidizing agent (model number: L860020-06) were obtained from SAFC (registered trademark) Proligo (registered trademark) Reagents. Acetonitrile (model number: 018-14451) and deblocking solution (model number: 042-28921) were purchased from Wako Pure Chemical Industries, Ltd. The activator used was 0.25M 5-ethylthio-1H-tetrazole/dry acetonitrile (manufacturer code: 30-3140-52, manufactured by Glen Research). The coupling time of acetonitrile solution (0.1M) containing Compound 28 was set to 20 minutes, and, when Compound 28 was introduced into the oligonucleotide successively for three bases, double coupling was performed only at the third base. The other conditions were as those for synthesis of native DNA.

Regarding the fluorescent modification, when amidite was introduced as a fluorescent agent to the oligonucleotide, the fluorescent agent may be hydrolyzed during the subsequent treatment with 75% trifluoroacetic acid (TFA). Thus, amidite Thiol-Modifer C6 S-S (manufacturer code: 10-1936-90, Glen Research) represented by the structural formula below was added by a DNA automated synthesizer at the 5' end of the oligonucleotide, and the processing was ended without deprotecting the protecting group, i.e., the dimethoxytrityl group (DMTr group), so that a precursor (Compound 49) of fluorescent labeled modified oligonucleotide analogs (Compounds 53 to 57) was obtained. It is known that the disulfide bond of the amidite Thiol-Modifer C6 S-S is sufficiently resistant to 75% TFA.

[Chemical 20]

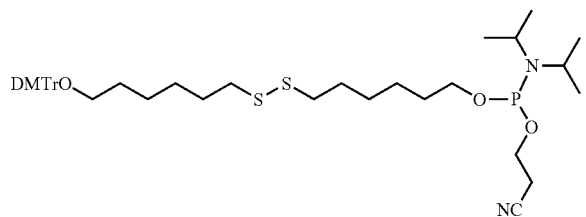

For the purpose of comparison, oligonucleotide analogs (Compounds 58 to 61: shown in Table 10 below) (manufactured by Gene Design Inc.) containing an urea-bridged artificial nucleic acid 2',4'-BNA/LNA (5-methyl-2'-O,4'-C-methyleneuridine) instead of Compound 28 were purchased and used. The structure of this precursor (Compound 50) of the oligonucleotide analogs is shown below.

[Chemical 21]

5'-HO—C6-S—S—C6-Oligonucleotide-3' (Compound 50)

The obtained precursor (Compound 49) was extracted from the CPG support using a 28% ammonia aqueous solution, ammonia was removed therefrom using a NAP-10 column (code number: 17-0854-01, GE Healthcare), and the resulting material was purified by RP-HPLC and lyophilized. RP-HPLC was performed using a Shimadzu LC-10AT$_{VP}$, a Shimadzu SPD-10A$_{VP}$, and a Shimadzu CTO-10$_{VP}$ following the conditions below.

Mobile Phase

Solution (A): 0.1M triethylammonium acetate buffer, pH 7.0

Solution (B): 80% acetonitrile/0.1M triethylammonium acetate buffer

Gradient: Solution (B) Concentration: 0-100% (80 min)

Columns Used:

Waters XBridge™ OST C18 2.5 μm (10×50 mm product number: 186003954)

Flow Rate: 3.0 mL/min

Column Temperature: 50° C.

Detection: UV (254 nm)

Next, 75% trifluoroacetic acid was added, the Boc group and the DMTr group were removed from the thus purified precursor (Compound 49) by performing treatment at room temperature for 6 hours, and a trifluoroacetic acid was removed using a NAP-10 column, so that a lyophilized and deprotected precursor (Compound 50) was obtained.

According to the protocol of the Thiol-Modifer C6 S-S, 100 mM DTT/TE buffer (pH 7.0) was added to the deprotected precursor (Compound 50) and the disulfide bond was reduced at room temperature for 2 hours, so that an SH group was produced. The obtained precursor after reduction (Compound 51) was purified by RP-HPLC (Solution (B): 50% acetonitrile/0.1M triethylammonium acetate buffer; Gradient: Solution (B) concentration 0-50%/25 min), and taken out. The structure of the obtained precursor after reduction (Compound 51) is shown below.

[Chemical 22]

5'-HS-C6-Oligonucleotide-3' (Compound 51)

The SH group was produced through the reduction as described above, and Alexa Fluor 488 C5 maleimide (product code: A-10254, manufactured by Life technologies) represented by the structural formula below was added to the purified precursor (Compound 51) in an amount of 10 equivalents with respect to the precursor (Compound 51), after which the mixture was reacted at room temperature overnight, so that the SH group was bound to the maleimide (Nucleic Acids Research, 36, 2764-2776, 2008).

[Chemical 23]

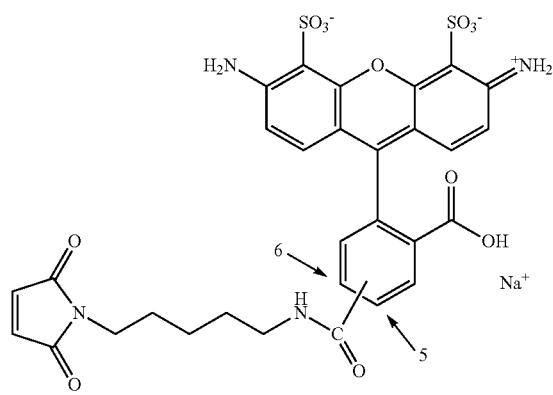

Subsequently, purification was performed by RP-HPLC (Solution (B): 50% acetonitrile/0.1M triethylammonium acetate buffer; Gradient: Solution (B) concentration 0-50%/25 min), so that fluorescent labeled modified oligonucleotide analogs (Compound 52: Compounds 53 to 61, SEQ ID Nos. 38 to 46) were obtained. Of these, Compounds 54 to 57 (SEQ ID Nos. 39 to 42) were fluorescent labeled GuNA modified oligonucleotides (F-GuNA-ODN). The structure of the obtained fluorescent labeled modified oligonucleotide analog (Compound 52) is shown below.

[Chemical 24]

(Compound 52)

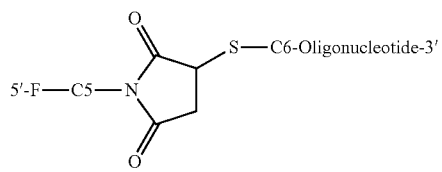

The synthesized fluorescent labeled modified oligonucleotide analogs (Compounds 53 to 61, SEQ ID Nos. 38 to 46) were purified and their purities were determined as in Example 2.

Mass spectrometry of the synthesized fluorescent labeled modified oligonucleotide analogs (Compounds 53 to 61, SEQ ID Nos. 38 to 46) was performed with a MALDI-TOF-MS (SpiralTOF JMS-S3000, JEOL). Table 10 shows the results.

TABLE 10

| Oligonucleotide[*1] | Yield (%) | Time of Flight Mass Spectrometry | |
|---|---|---|---|
| | | Cald. (M-H⁻) | Measured (M-H⁻) |
| SEQ ID No. 38: 5'-d(FSTTTTTTTTTT)-3' (Compound 53) | 16 | 3873.84 | 3874.55 |
| SEQ ID No. 39: 5'-d(FSTTTTTT<u>T</u>TTTT)-3' (Compound 54) | 11 | 3942.91 | 3943.78 |
| SEQ ID No. 40: 5'-d(FST<u>T</u>TTT<u>T</u>TTT<u>T</u>T)-3' (Compound 55) | 19 | 4081.04 | 4080.66 |
| SEQ ID No. 41: 5'-d(FSTTTTT<u>TTTTT</u>)-3' (Compound 56) | 16 | 4081.04 | 4080.90 |
| SEQ ID No. 42: 5'-d(FST<u>TTTTTTTTT</u>)-3' (Compound 57) | 8 | 4288.23 | 4287.31 |
| SEQ ID No. 43: 5'-d(FSTTTTTTTTTT)-3' (Compound 58) | *2 | 3901.85 | 3902.53 |
| SEQ ID No. 44: 5'-d(FSTTTTTTTTTT)-3' (Compound 59) | *2 | 3957.87 | 3955.85 |
| SEQ ID No. 45: 5'-d(FSTTTTTTTTTT)-3' (Compound 60) | *2 | 3957.87 | 3957.19 |
| SEQ ID No. 46: 5'-d(FSTTTTTTTTTT)-3' (Compound 61) | *2 | 4041.90 | 4040.82 |

[*1]<u>T</u>: GuNA
[*1]T: 2',4'-BNA/LNA  S: thiol  F: Alexa Fluor 488
*2 Not measured (2) Introduction of Fluorescent Labeled GuNA Modified Oligonucleotides F-GuNA-ODN into Human Hepatoma Cells (HuH-7) and Observation of Kinetics in the Cells First, as a preparation, the glass portion of a cell bottom dish (model code: 3970-035, Iwaki) for cell observation was coated by collagen by application of 1 mL of 100 μg/mL collagen/hydrochloric acid (pH 3.0) (Cellmatrix Type I-C, manufactured by Nitta Gelatin Inc.).

After the dish was allowed to stand at room temperature for 30 minutes, the collagen was removed therefrom, and the dish was washed once with phosphate buffered saline and then dried at room temperature for 1 hour. Next, $4.5 \times 10^5$ HuH-7 cells (purchased from JCRB Cell Bank (cell number: JCRB0403)) were plated, and were cultured overnight in a phenol red-free medium 10% FBS/DMEM (product number: 08490-05, manufactured by Nacalai Tesque, Inc.) (5% $CO_2$), and, then, each of the fluorescent labeled modified oligonucleotide analogs (Compounds 53 to 61, SEQ ID Nos. 38 to 46) obtained in (1) was added at a concentration of 500 nM.

After the fluorescent labeled modified oligonucleotide analogs (Compounds 53 to 61, SEQ ID Nos. 38 to 46) were added, the culture was continued for another 12 hours, after which the cultured HuH-7 cells were washed once with a Hanks' balanced salt solution (HBSS, product number: 14025-092, manufactured by Life technologies), and nuclei and lysosomes were stained using Hoechst 33342 (product number:113570, manufactured by Life technologies) and LysoTracker (registered trademark) Red DND-99 (catalog number: L-7528, manufactured by Life technologies) according to the protocol. Subsequently, 2 mL of Hanks' balanced salt solution was added, and fluorescence images were acquired using an incident-light fluorescence microscope (BZ-9000, manufactured by Keyence Corporation). An object lens used was a 40× phase-contrast lens (S Plan Fluor, manufactured by Nikon Corporation).

The detection filter set and the exposure time of each fluorescent agent are as follows.

Alexa Fluor 488: Ex 470/40 nm, DM 495 nm, BA 535/50 nm (GFP-B, manufactured by Keyence Corporation), 5 seconds Hoechst 33342: Ex 360/40 nm, DM 400 nm, BA 460/50 nm (DAPI-B, manufactured by Keyence Corporation), 2 seconds LysoTracker (registered trademark) Red DND-99: Ex 540/25 nm, DM 565 nm, BA 605/55 nm (TRITC, manufactured by Keyence Corporation), 1.2 seconds As a result of introduction of the fluorescent labeled modified oligonucleotide analogs (Compounds 53 to 61, SEQ ID Nos. 38 to 46) to the HuH-7 cells, particularly intense fluorescence emission was observed in the cells when two types of oligonucleotides, i.e., Compound 57 (SEQ ID No. 42) into which 6 residues of Compound 28 were introduced and Compound 61 (SEQ ID No. 46) into which 6 residues of 2',4'-BNA/LNA were introduced, were added. Compared with these, the other oligonucleotides had a lower level of fluorescence emission. FIG. 4 shows microphotographs of kinetics of Compound 57 (SEQ ID No. 42) (A to D) and Compound 61 (SEQ ID No. 46) (E to H) in HuH-7 cells: where A and E are phase-contrast images; B and F are fluorescence images using Alexa Fluor 488 (oligonucleotides); C and G are fluorescence images of Hoechst 33342 (nuclei); and D and H are fluorescence images using LysoTracker (lysosomes) (scale bar 50 μm). When the oligonucleotide of Compound 57 (SEQ ID No. 42) into which 6 residues of Compound 28 were introduced was used, intense fluorescence emission was observed (FIG. 4B). On the other hand, when the oligonucleotide of Compound 61 (SEQ ID No. 46) into which 6 residues of 2',4'-BNA/LNA were introduced was used, the fluorescence emission was observed to some extent, but its level was lower than that of Compound 57 (SEQ ID No. 42) using Compound 28 (FIG. 4F). The reason for this seems to be that, in the case of Compound 57 (SEQ ID No. 42), 6 residues of Compound 28 were introduced, and, thus, the introduction efficiency to the cells was improved, and the electric charge of the entire oligonucleotide was changed so that the adsorption efficiency to the cell surfaces was improved. On the other hand, it seems that, in the case of Compound 61 (SEQ ID No. 46), 6 residues of 2',4'-BNA/LNA were introduced, and, thus, the introduction efficiency to the cells was improved, but the electric charge was not changed and the adsorption efficiency to the cell surfaces was not improved, so that the fluorescence emission level was lower than that of Compound 57 (SEQ ID No. 42).

FIG. 5 shows microphotographs of kinetics of Compound 57 in HuH-7 cells, showing photographs (A to D) obtained by enlarging the region indicated by the arrow in FIG. 4B, in FIGS. 4A to 4D. A close observation of the localization of the obtained fluorescence emission in the cells showed that the added oligonucleotides were not present inside the nuclei, and a large amount thereof was accumulated in the vesicles of the cytoplasms and also was present in the lysosomes.

That is to say, it was proven that changing the electric charge of the entire oligonucleotide by providing the positively charged guanidino group to the negatively charged oligonucleotide is a useful approach for improving the introduction efficiency of the oligonucleotide into cells.

Note that it has been conventionally difficult to introduce oligonucleotides into cells without using a drug delivery system in view of the enzyme resistance or the cell permeability. In order to solve this problem, an approach is generally used in which phosphorothioate modification is performed on the phosphate backbones of the oligonucleotides. However, the phosphorothioate modification may lower the productivity, the safety, and the drug action, due to chirality problem on phosphorus atoms. This time, it was possible to improve the cell permeability without performing phosphorothioate modification, and, thus, it is seen that the guanidine-bridged artificial nucleosides and the oligonucleotides of the present invention overcome these disadvantages and can contribute to use of nucleic acids as pharmaceuticals.

INDUSTRIAL APPLICABILITY

The present invention can provide a nucleic acid molecule for an oligonucleotide having a high binding affinity and a high specificity to a target nucleic acid and exhibiting a high nuclease resistance. Such a nucleic acid molecule can make a great contribution as a material for a nucleic acid drug for use in antisense therapies, antigene therapies, aptamer-based therapies, siRNA-based therapies, and the like, which are expected as new methods for treating or preventing diseases.

The invention claimed is:

1. A compound represented by formula I or II below or a salt thereof:

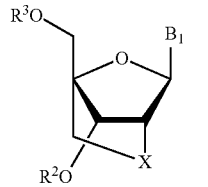

(I)

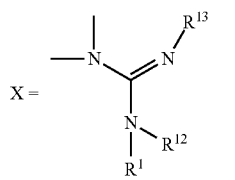

or

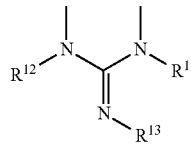

(II)

wherein $B_1$ represents:
- a purin-9-yl group;
- a 2-oxo-1,2-dihydropyrimidin-1-yl group;
- a purin-9-yl group that has any one or more substituents selected from the group consisting of a hydroxyl group, a hydroxyl group protected by a protecting group in nucleic acid synthesis, a $C_1$ to $C_6$ linear alkyl group, a $C_1$ to $C_6$ linear alkoxy group, a mercapto group, a mercapto group protected by a protecting group in nucleic acid synthesis, a $C_1$ to $C_6$ linear alkylthio group, an amino group, a $C_1$ to $C_6$ linear alkylamino group, an amino group protected by a protecting group in nucleic acid synthesis, and a halogen atom;
- a 2-oxo-1,2-dihydropyrimidin-1-yl group that has any one or more substituents selected from the group consisting of a hydroxyl group, a hydroxyl group protected by a protecting group in nucleic acid synthesis, a $C_1$ to $C_6$ linear alkyl group, a $C_1$ to $C_6$ linear alkoxy group, a mercapto group, a mercapto group protected by a protecting group in nucleic acid synthesis, a $C_1$ to $C_6$ linear alkylthio group, an amino group, a $C_1$ to $C_6$ linear alkylamino group, an amino group protected by a protecting group in nucleic acid synthesis, and a halogen atom;

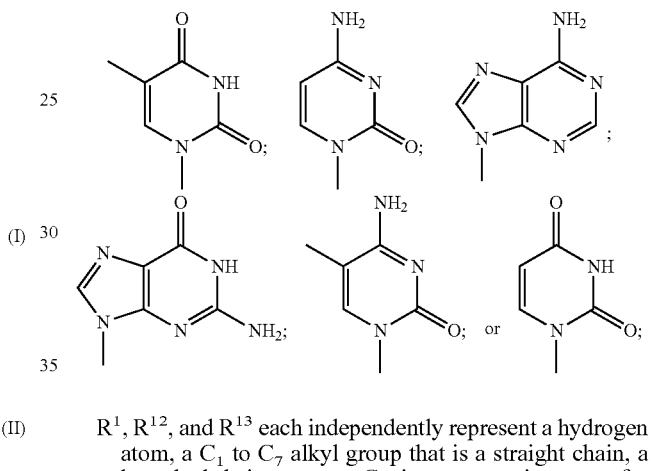

$R^1$, $R^{12}$, and $R^{13}$ each independently represent a hydrogen atom, a $C_1$ to $C_7$ alkyl group that is a straight chain, a branched chain or up to a $C_7$ ring, a protecting group for an amino group, or

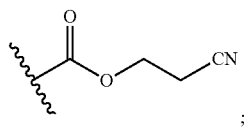 [SMILES: *C(=O)OCCC#N]

and $R^2$ and $R^3$ each independently represent
- a hydrogen atom,
- a protecting group for a hydroxyl group in nucleic acid synthesis,
- a $C_1$ to $C_7$ alkyl group that is a straight chain, a branched chain or up to a $C_7$ ring,
- a $C_2$ to $C_7$ alkenyl group that is a straight chain, a branched chain or up to a $C_7$ ring,
- a $C_6$ to $C_{12}$ aryl group,
- a $C_6$ to $C_{12}$ aryl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, an amino group protected by a protecting group in nucleic acid synthesis, and a halogen atom, a $C_6$ to $C_{12}$ aryl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom, an aralkyl group having a $C_6$ to $C_{12}$ aryl moiety, an aralkyl group having a $C_6$ to $C_{12}$ aryl moiety that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom, an aralkyl group having a $C_6$ to $C_{12}$ aryl moiety, an aralkyl group having a $C_6$ to $C_{12}$ aryl moiety that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom, an acyl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a $C_1$ to $C_6$ linear alkylthio group, a $C_1$ to $C_6$ linear alkylamino group, an amino group protected by a protecting group in nucleic acid synthesis, and a halogen atom, a silyl group that has three substituents selected from the group consisting of a hydroxyl group protected by a protecting group in nucleic acid synthesis, a $C_1$ to $C_6$ linear alkyl group, a $C_1$ to $C_6$ linear alkoxy group, and an amino group protected by a protecting group in nucleic acid synthesis, a phosphate group, a phosphate group that has any one or more substituents selected from the group consisting of a $C_1$ to $C_6$ linear alkyl group, and a $C_1$ to $C_6$ linear alkoxy group, a phosphate group protected by a protecting group in nucleic acid synthesis, or —P(R$^4$)R$^5$, wherein R$^4$ and R$^5$ each independently represent a hydroxyl group protected by a protecting group in nucleic acid synthesis, a $C_1$ to $C_5$ alkoxy group, a $C_1$ to $C_6$ cyanoalkoxy group, or a dialkylamino group substituted with a two $C_1$ to $C_6$ alkyl groups, wherein the protecting group in nucleic acid synthesis is a $C_1$ to $C_6$ alkyl group; a $C_1$ to $C_6$ alkenyl group; an acyl group; a tetrahydropyranyl group or a tetrahydrothiopyranyl group; a tetrahydrofuranyl group or a tetrahydrothiofuranyl group; a methyl group substituted with a $C_1$ to $C_6$ alkoxy group; a methyl group substituted with a $C_1$ to $C_6$ alkoxy group substituted with a $C_1$ to $C_6$ alkoxy group; a methyl group substituted with a $C_1$ to $C_6$ alkoxy group substituted with a halogen atom; an ethyl group substituted with a $C_1$ to $C_6$ alkoxy group; an ethyl group substituted with a halogen atom; a methyl group substituted with one to three aryl groups; a methyl group substituted with one to three aryl groups substituted with at least one substituent selected from the group consisting of a $C_1$ to $C_6$ alkyl group, a $C_1$ to $C_6$ alkoxy group, a halogen atom, and a cyano group; a carbonyl group substituted with a $C_1$ to $C_6$ alkoxy group; an aryl group substituted with at least one substituents selected from the group consisting of a halogen atom, a $C_1$ to $C_6$ alkoxy group, and a nitro group; a carbonyl group substituted with a $C_1$ to $C_6$ alkoxy group substituted with at least one substituent selected from the group consisting of a halogen atom and a silyl group substituted with three $C_1$ to $C_6$ alkyl groups; an alkenyloxycarbonyl group; or an aralkyloxycarbonyl group substituted with an aryl group substituted with at least one substituent selected from the group consisting of a $C_1$ to $C_6$ alkoxy group and a nitro group;

wherein the protecting group for a hydroxyl group in nucleic acid synthesis is an aliphatic acyl group; an aromatic acyl group; a methyl group substituted with one to three aryl groups; a methyl group substituted with one to three aryl groups substituted with at least one substituent selected from the group consisting of a $C_1$ to $C_6$ alkyl group, a $C_1$ to $C_6$ alkoxy group, a halogen atom, a cyano group and a trialkyl substituted silyl group; and wherein the protecting group for an amino group is an acyl group, a benzoyl group, a tert-butoxycarbonyl group, or a 9-fluorenylmethyloxycarbonyl group;

and with the proviso that substituents specified in all chemical structures by each of the terms —OH (hydroxyl group), mercapto group (—SH), a $C_1$ to $C_6$ linear alkylamino group, a phosphate group, and an amino group (—NH2) or substituted amino group in compounds intended to be phosphoramidites, must be modified before phosphoramidite group introduction with all necessary protecting groups.

2. The compound or a salt thereof of claim 1, wherein, in formula I or II, B$_1$ represents a 6-aminopurin-9-yl group, a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group, a 4-amino-2-oxo-5-fluoro-1,2-dihydropyrimidin-1-yl group, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group, a 2-oxo-4-hydroxy-5-methyl-1,2-dihydropyrimidin-1-yl group, or a 4-amino-5-methyl-2-oxo-1,2-dihydropyrimidin-1-yl group.

3. The compound or a salt thereof of claim 1, wherein, in formula I or II, B$_1$ represents a group represented by the formula:

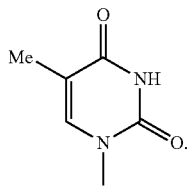

4. An oligonucleotide synthesized by a phosphoramidite protocol according to Caruthers' method with the substitution of a step of reacting a compound represented by formula I or II below or a salt thereof with a nucleic acid, followed by a step of oxidation to form a phosphate diester linkage therebetween, or a pharmacologically acceptable salt thereof, wherein the compound represented by formula I or II is:

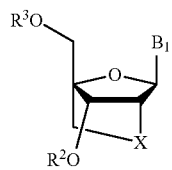

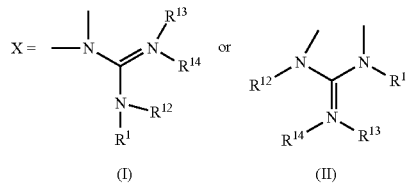

wherein (i) $B_1$ represents:
  a purin-9-yl group;
  a 2-oxo-1,2-dihydropyrimidin-1-yl group;
  a purin-9-yl group that has any one or more substituents selected from the group consisting of a hydroxyl group, a hydroxyl group protected by a protecting group in nucleic acid synthesis, a $C_1$ to $C_6$ linear alkyl group, a $C_1$ to $C_6$ linear alkoxy group, a mercapto group, a mercapto group protected by a protecting group in nucleic acid synthesis, a $C_1$ to $C_6$ linear alkylthio group, an amino group, a $C_1$ to $C_6$ linear alkylamino group, an amino group protected by a protecting group in nucleic acid synthesis, and a halogen atom;
  a 2-oxo-1,2-dihydropyrimidin-1-yl group that has any one or more substituents selected from the group consisting of a hydroxyl group, a hydroxyl group protected by a protecting group in nucleic acid synthesis, a $C_1$ to $C_6$ linear alkyl group, a $C_1$ to $C_6$ linear alkoxy group, a mercapto group, a mercapto group protected by a protecting group in nucleic acid synthesis, a $C_1$ to $C_6$ linear alkylthio group, an amino group, a $C_1$ to $C_6$ linear alkylamino group, an amino group protected by a protecting group in nucleic acid synthesis, and a halogen atom;

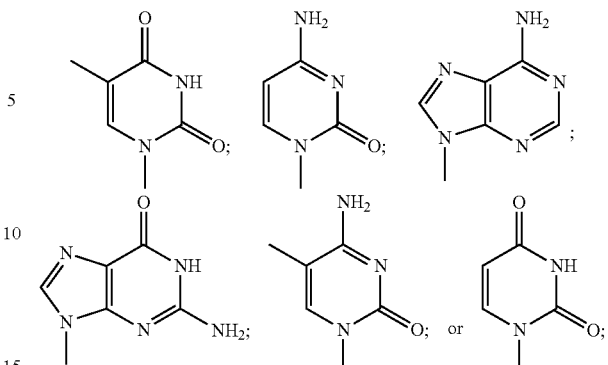

$R^1$, $R^{12}$, and $R^{13}$ each independently represent a hydrogen atom, a $C_1$ to $C_7$ alkyl group that is a straight chain, a branched chain or up to a $C_7$ ring, a protecting group for an amino group, or

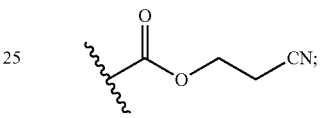

and (ii) one substituent of $R^2$ and $R^3$ represents —$P(R^4)R^5$, wherein $R^4$ represents a hydroxyl group protected by a protecting group in nucleic acid synthesis, a $C_1$ to $C_5$ alkoxy group, or a $C_1$ to $C_6$ cyanoalkoxy group, and $R^5$ represents a dialkylamino group substituted with two $C_1$ to $C_6$ alkyl groups, and (iii) the other substituent of $R^2$ and $R^3$ represents
  a hydrogen atom,
  a protecting group for a hydroxyl group in nucleic acid synthesis,
  a $C_1$ to $C_7$ alkyl group that is a straight chain, a branched chain or up to a $C_7$ ring,
  a $C_2$ to $C_7$ alkenyl group that is a straight chain, a branched chain or up to a $C_7$ ring,
  a $C_6$ to $C_{12}$ aryl group,
  a $C_6$ to $C_{12}$ aryl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, an amino group protected by a protecting group in nucleic acid synthesis, and a halogen atom,
  a $C_6$ to $C_{12}$ aryl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom,
  an aralkyl group having a $C_6$ to $C_{12}$ aryl moiety,
  an aralkyl group having a $C_6$ to $C_{12}$ aryl moiety that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom, an aralkyl group having a $C_6$ to $C_{12}$ aryl moiety, an aralkyl group having a $C_6$ to $C_{12}$ aryl moiety that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom, an acyl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a $C_1$ to $C_6$ linear alkylthio group, a $C_1$ to $C_6$ linear alkylamino group, an amino group protected by a protecting group in nucleic acid synthesis, and a halogen atom, a silyl group that has three substituents selected from the group consisting of a hydroxyl group protected by a protecting group in nucleic acid synthesis, a $C_1$ to $C_6$ linear alkyl group, a $C_1$ to $C_6$ linear alkoxy group, and an amino group protected by a protecting group in nucleic acid synthesis, a phosphate group, a phosphate group that has any one or more substituents selected from the group consisting of a $C_1$ to $C_6$ linear alkyl group, and a $C_1$ to $C_6$ linear alkoxy group, or a phosphate group protected by a protecting group in nucleic acid synthesis, and wherein the protecting group in nucleic acid synthesis is a $C_1$ to $C_6$ alkyl group; a $C_1$ to $C_6$ alkenyl group; an acyl group; a tetrahydropyranyl group or a tetrahydrothiopyranyl group; a tetrahydrofuranyl group or a tetrahydrothiofuranyl group; a silyl group; a methyl group substituted with a $C_1$ to $C_6$ alkoxy group; a methyl group substituted with a $C_1$ to $C_6$ alkoxy group substituted with a $C_1$ to $C_6$ alkoxy group; a methyl group substituted with a $C_1$ to $C_6$ alkoxy group substituted with a halogen atom; an ethyl group substituted with a $C_1$ to $C_6$ alkoxy group; an ethyl group substituted with a halogen atom; a methyl group substituted with one to three aryl groups; a methyl group substituted with one to three aryl groups substituted with at least one substituent selected from the group consisting of a $C_1$ to $C_6$ alkyl group, a $C_1$ to $C_6$ alkoxy group, a halogen atom, and a cyano group; a carbonyl group substituted with a $C_1$ to $C_6$ alkoxy group; an aryl group substituted with at least one substituents selected from the group consisting of a halogen atom, a $C_1$ to $C_6$ alkoxy group, and a nitro group; a carbonyl group substituted with a $C_1$ to $C_6$ alkoxy group substituted with at least one substituent selected from the group consisting of a halogen atom and a silyl group substituted with three $C_1$ to $C_6$ alkyl groups; an alkenyloxycarbonyl group; or an aralkyloxycarbonyl group substituted with an aryl group substituted with at least one substituent selected from the group consisting of a $C_1$ to $C_6$ alkoxy group and a nitro group;

wherein the protecting group for a hydroxyl group in nucleic acid synthesis is an aliphatic acyl group; an aromatic acyl group; a methyl group substituted with one to three aryl groups; a methyl group substituted with one to three aryl groups substituted with at least one substituent selected from the group consisting of a $C_1$ to $C_6$ alkyl group, a $C_1$ to $C_6$ alkoxy group, a halogen atom, and a cyano group and a trialkylsubstituted silyl group; and wherein the protecting group for an amino group is an acyl group, a benzoyl group, a tert-butoxycarbonyl group, or a 9-fluorenylmethyloxycarbonyl group;

and with the proviso that substituents specified in all chemical structures by each of the terms —OH (hydroxyl group), mercapto group (—SH), a $C_1$ to $C_6$ linear alkylamino group, a phosphate group, and an amino group (—NH2) or substituted amino group in compounds intended to be phosphoramidites, must be modified before phosphoramidite group introduction with all necessary protecting groups.

5. The oligonucleotide or a pharmacologically acceptable salt thereof of claim 4, wherein, in formula I or II, $B_1$ represents a group represented by the formula:

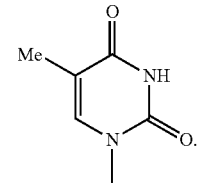

6. The oligonucleotide or a pharmacologically acceptable salt thereof of claim 4, wherein, in formula I or II, $B_1$ represents a 6-aminopurin-9-yl group, a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group, a 4-amino-2-oxo-5-fluoro-1,2-dihydropyrimidin-1-yl group, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group, a 2-oxo-4-hydroxy-5-methyl-1,2-dihydropyrimidin-1-yl group, or a 4-amino-5-methyl-2-oxo-1,2-dihydropyrimidin-1-yl group.

7. An oligonucleotide synthesized according to Caruthers' method with the substitution of a step of reacting of a compound represented by formula I or II below or a salt thereof and a nucleic acid followed by a step of treating with a sulfurizing agent to form a phosphorothioate linkage therebetween, or a pharmacologically acceptable salt thereof, wherein the compound represented by formula I or II is:

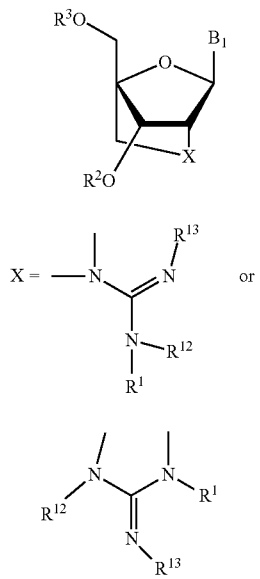

wherein
(i) $B_1$ represents:
a purin-9-yl group;
a 2-oxo-1,2-dihydropyrimidin-1-yl group;
a purin-9-yl group that has any one or more substituents selected from the group consisting of a hydroxyl group, a hydroxyl group protected by a protecting group in nucleic acid synthesis, a $C_1$ to $C_6$ linear alkyl group, a $C_1$ to $C_6$ linear alkoxy group, a mercapto group, a mercapto group protected by a protecting group in nucleic acid synthesis, a $C_1$ to $C_6$ linear alkylthio group, an amino group, a $C_1$ to $C_6$ linear alkylamino group, an amino group protected by a protecting group in nucleic acid synthesis, and a halogen atom;
a 2-oxo-1,2-dihydropyrimidin-1-yl group that has any one or more substituents selected from the group consisting of a hydroxyl group, a hydroxyl group protected by a protecting group in nucleic acid synthesis, a $C_1$ to $C_6$ linear alkyl group, a $C_1$ to $C_6$ linear alkoxy group, a mercapto group, a mercapto group protected by a protecting group in nucleic acid synthesis, a $C_1$ to $C_6$ linear alkylthio group, an amino group, a $C_1$ to $C_6$ linear alkylamino group, an amino group protected by a protecting group in nucleic acid synthesis, and a halogen atom;

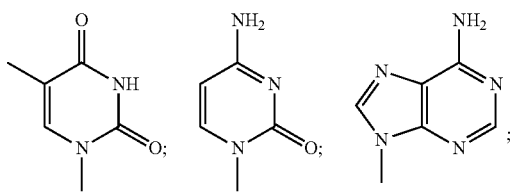

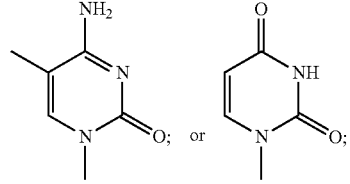

$R^1$, $R^{12}$, and $R^{13}$ each independently represent a hydrogen atom, a $C_1$ to $C_7$ alkyl group that is a straight chain, a branched chain or up to a $C_7$ ring, a protecting group for an amino group, or

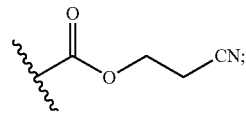 [SMILES: *C(=O)OCCC#N]

and
(ii) one substituent of $R^2$ and $R^3$ represents —P($R^4$)$R^5$, wherein $R^4$ represents a hydroxyl group protected by a protecting group in nucleic acid synthesis, a $C_1$ to $C_5$ alkoxy group, or a $C_1$ to $C_6$ cyanoalkoxy group, and $R^5$ represents a dialkylamino group substituted with two $C_1$ to $C_6$ alkyl groups, and
(iii) the other substituent of $R^2$ and $R^3$ represents
a hydrogen atom,
a protecting group for a hydroxyl group in nucleic acid synthesis,
a $C_1$ to $C_7$ alkyl group that is a straight chain, a branched chain or up to a $C_7$ ring,
a $C_2$ to $C_7$ alkenyl group that is a straight chain, a branched chain or up to a $C_7$ ring,
a $C_6$ to $C_{12}$ aryl group,
a $C_6$ to $C_{12}$ aryl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, an amino group protected by a protecting group in nucleic acid synthesis, and a halogen atom,
a $C_6$ to $C_{12}$ aryl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom,
an aralkyl group having a $C_6$ to $C_{12}$ aryl moiety,
an aralkyl group having a $C_6$ to $C_{12}$ aryl moiety that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom, an aralkyl group having a $C_6$ to $C_{12}$ aryl moiety, an aralkyl group having a $C_6$ to $C_{12}$ aryl moiety that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a mercapto group protected by a protecting group in nucleic acid synthesis, a $C_1$ to $C_6$ linear alkylthio group, a $C_1$ to $C_6$ linear alkylamino group, an amino group protected by a protecting group in nucleic acid synthesis, and a halogen atom, an acyl group that has any one or more substituents selected from the group consisting of a hydroxyl group protected by a protecting group in nucleic acid synthesis, a $C_1$ to $C_6$ linear alkyl group, a $C_1$ to $C_6$ linear alkoxy group, a $C_1$ to $C_6$ linear alkylthio group, a $C_1$ to $C_6$ linear alkylamino group, an amino group protected by a protecting group in nucleic acid synthesis, and a halogen atom, a silyl group that has three substituents selected from the group consisting of a hydroxyl group protected by a protecting group in nucleic acid synthesis, a $C_1$ to $C_6$ linear alkyl group, a $C_1$ to $C_6$ linear alkoxy group, and an amino group protected by a protecting group in nucleic acid synthesis, a phosphate group, a phosphate group that has any one or more substituents selected from the group consisting of a $C_1$ to $C_6$ linear alkyl group, and a $C_1$ to $C_6$ linear alkoxy group, or a phosphate group protected by a protecting group in nucleic acid synthesis, and wherein the protecting group in nucleic acid synthesis is a $C_1$ to $C_6$ alkyl group; a $C_1$ to $C_6$ alkenyl group; an acyl group; a tetrahydropyranyl group or a tetrahydrothiopyranyl group; a tetrahydrofuranyl group or a tetrahydrothiofuranyl group; a silyl group; a methyl group substituted with a $C_1$ to $C_6$ alkoxy group; a methyl group substituted with a $C_1$ to $C_6$ alkoxy group substituted with a $C_1$ to $C_6$ alkoxy group; a methyl group substituted with a $C_1$ to $C_6$ alkoxy group substituted with a halogen atom; an ethyl group substituted with a $C_1$ to $C_6$ alkoxy group; an ethyl group substituted with a halogen atom; a methyl group substituted with one to three aryl groups; a methyl group substituted with one to three aryl groups substituted with at least one substituent selected from the group consisting of a $C_1$ to $C_6$ alkyl group, a $C_1$ to $C_6$ alkoxy group, a halogen atom, and a cyano group; a carbonyl group substituted with a $C_1$ to $C_6$ alkoxy group; an aryl group substituted with at least one substituents selected from the group consisting of a halogen atom, a $C_1$ to $C_6$ alkoxy group, and a nitro group; a carbonyl group substituted with a $C_1$ to $C_6$ alkoxy group substituted with at least one substituent selected from the group consisting of a halogen atom and a silyl group substituted with three $C_1$ to $C_6$ alkyl groups; an alkenyloxycarbonyl group; or an aralkyloxycarbonyl group substituted with an aryl group substituted with at least one substituent selected from the group consisting of a $C_1$ to $C_6$ alkoxy group and a nitro group;

wherein the protecting group for a hydroxyl group in nucleic acid synthesis is an aliphatic acyl group; an aromatic acyl group; a methyl group substituted with one to three aryl groups; a methyl group substituted with one to three aryl groups substituted with at least one substituent selected from the group consisting of a $C_1$ to $C_6$ alkyl group, a $C_1$ to $C_6$ alkoxy group, a halogen atom, and a cyano group and a trialkylsubstituted silyl group; and wherein the protecting group for an amino group is an acyl group, a benzoyl group, a tert-butoxycarbonyl group, or a 9-fluorenylmethyloxycarbonyl group;

and with the proviso that substituents specified in all chemical structures by each of the terms —OH (hydroxyl group), mercapto group (—SH), a $C_1$ to $C_6$ linear alkylamino group, a phosphate group, and an amino group (—NH2) or substituted amino group in compounds intended to be phosphoramidites, must be modified before phosphoramidite group introduction with all necessary protecting groups.

* * * * *